(12) United States Patent
Cheng

(10) Patent No.: US 9,568,474 B2
(45) Date of Patent: *Feb. 14, 2017

(54) IN SITU DETECTION OF EARLY STAGES AND LATE STAGES HPV INFECTION

(71) Applicant: Shuling Cheng, Fremont, CA (US)

(72) Inventor: Shuling Cheng, Fremont, CA (US)

(73) Assignee: OncoHealth Corp., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/335,511

(22) Filed: Jul. 18, 2014

(65) Prior Publication Data

US 2015/0147748 A1  May 28, 2015

Related U.S. Application Data

(62) Division of application No. 12/456,054, filed on Jun. 10, 2009, now Pat. No. 8,859,218.

(60) Provisional application No. 61/131,991, filed on Jun. 13, 2008, provisional application No. 61/192,912, filed on Sep. 22, 2008.

(51) Int. Cl.
| | |
|---|---|
| *G01N 33/569* | (2006.01) |
| *C07K 16/08* | (2006.01) |
| *C12Q 1/70* | (2006.01) |
| *G01N 33/571* | (2006.01) |

(52) U.S. Cl.
CPC ....... *G01N 33/56983* (2013.01); *C07K 16/084* (2013.01); *C12Q 1/708* (2013.01); *G01N 33/571* (2013.01); *G01N 2333/025* (2013.01); *G01N 2469/10* (2013.01)

(58) Field of Classification Search
None
See application file for complete search history.

(56) References Cited

U.S. PATENT DOCUMENTS

| | | |
|---|---|---|
| 3,633,999 A | 1/1972 | Buckles |
| 4,511,220 A | 4/1985 | Scully |
| 4,619,508 A | 10/1986 | Shibuya et al. |
| 4,744,615 A | 5/1988 | Fan et al. |
| 4,851,978 A | 7/1989 | Ichihara |
| 5,045,447 A | 9/1991 | Minson |
| 5,057,411 A | 10/1991 | Lancaster et al. |
| 5,061,025 A | 10/1991 | Debesis |
| 5,109,465 A | 4/1992 | Klopotek |
| 5,183,755 A | 2/1993 | Ohmoto et al. |
| 5,224,200 A | 6/1993 | Rasmussen et al. |
| 5,233,460 A | 8/1993 | Partlo et al. |
| 5,307,207 A | 4/1994 | Ichihara |
| 5,315,427 A | 5/1994 | Rauch et al. |
| 5,328,785 A | 7/1994 | Smith et al. |
| 5,357,365 A | 10/1994 | Ipposhi et al. |
| 5,401,627 A | 3/1995 | Dillner et al. |
| 5,415,995 A | 5/1995 | Schoolnik et al. |
| 5,453,814 A | 9/1995 | Aiyer |
| 5,561,081 A | 10/1996 | Takenouchi et al. |
| 5,591,574 A | 1/1997 | Orth et al. |
| 5,610,733 A | 3/1997 | Feldman et al. |
| 5,621,529 A | 4/1997 | Gordon et al. |
| 5,629,161 A | 5/1997 | Muller et al. |
| 5,662,410 A | 9/1997 | Suganuma |
| 5,665,535 A | 9/1997 | Orth et al. |
| 5,679,509 A | 10/1997 | Wheeler et al. |
| 5,695,770 A | 12/1997 | Raychaudhuri et al. |
| 5,699,191 A | 12/1997 | Fork |
| 5,754,278 A | 5/1998 | Kurtz |
| 5,876,723 A | 3/1999 | Cole et al. |
| 5,888,888 A | 3/1999 | Talwar et al. |
| 5,914,389 A | 6/1999 | Huibregtse et al. |
| 6,013,262 A | 1/2000 | Frazer et al. |
| 6,228,578 B1 | 5/2001 | Impraim et al. |
| 6,329,167 B1 | 12/2001 | Patterson et al. |
| 6,355,424 B1 | 3/2002 | Lorinez et al. |
| 6,420,106 B1 | 7/2002 | Gyllensten et al. |
| 6,489,105 B1 | 12/2002 | Matlashewski et al. |
| 6,524,825 B1 | 2/2003 | Mizzen et al. |
| 6,528,278 B2 | 3/2003 | Patterson et al. |
| 6,709,832 B1 | 3/2004 | Von Knebel Doeberitz et al. |
| 6,743,593 B2 | 6/2004 | Hu |
| 6,827,933 B2 | 12/2004 | Orth et al. |

(Continued)

FOREIGN PATENT DOCUMENTS

| | | |
|---|---|---|
| CN | 03825051.9 | 11/2005 |
| EP | 00256321 | 2/1988 |

(Continued)

OTHER PUBLICATIONS

Advisory action for U.S. Appl. No. 12/456,055 dated Mar. 12, 2012.
Bosch, et al 1995. Prevalence of human papillomavirus in cervical cancer: a worldwide perspective. J Natl Cancer Inst 87:796-802.
Doeberitz, Magnus Von Knebel "New Molecular tools for efficient screening of cervical cancer", Disease Markers 17 (2001) 123-128.
Fisher, et al. "The Association of Human Papillomavirus Type 16 E6 and E7 Antibodies with stage of Cervical Cancer", Gynecologic Oncology 61,73-78 (1996) Article No. 0099.

(Continued)

*Primary Examiner* — Agnieszka Boesen

(74) *Attorney, Agent, or Firm* — Fenwick & West

(57) ABSTRACT

Embodiments of the invention provide methods, monoclonal antibodies, polyclonal antibodies, assays, and kits for detecting HPV infection and HPV related cancer diagnosis, including infection by various HPV genotypes, early and/or late stage HPV-associated or HPV-specific cancers. The anti-HPV antibodies are used in performing immunological assays on clinical samples. Various immunological assays and kits for detecting HPV infection, cervical cancer, other HPV related cancers, early stage precancerous lesions as well as late stage cancer progression are also provided.

15 Claims, 13 Drawing Sheets

(56) References Cited

U.S. PATENT DOCUMENTS

| | | |
|---|---|---|
| 6,884,786 B1 | 4/2005 | Kieny et al. |
| 6,890,514 B2 | 5/2005 | Mathur et al. |
| 6,900,035 B2 | 5/2005 | Mizzen et al. |
| 6,933,123 B2 | 8/2005 | Hu et al. |
| 6,939,687 B2 | 9/2005 | Patterson et al. |
| 7,001,995 B1 | 2/2006 | Neeper et al. |
| 7,078,061 B2 | 7/2006 | Debad et al. |
| 7,157,233 B2 | 1/2007 | Fischer et al. |
| 7,361,460 B2 | 4/2008 | Williams |
| 7,399,467 B2 * | 7/2008 | Lu .............. C07K 16/084 424/130.1 |
| 7,455,973 B2 | 11/2008 | Fischer et al. |
| 7,501,261 B2 | 3/2009 | Meijer et al. |
| 7,510,838 B2 | 3/2009 | Fischer et al. |
| 7,838,215 B2 | 11/2010 | Gombrich et al. |
| 7,888,032 B2 | 2/2011 | Patterson et al. |
| 2001/0034021 A1 | 10/2001 | Muller et al. |
| 2003/0044870 A1 | 3/2003 | Sehr et al. |
| 2003/0190602 A1 | 10/2003 | Pressman et al. |
| 2004/0018487 A1 | 1/2004 | Lu et al. |
| 2004/0170644 A1 | 9/2004 | Mailere et al. |
| 2004/0175695 A1 | 9/2004 | Debad et al. |
| 2004/0260157 A1 | 12/2004 | Montes et al |
| 2005/0037017 A1 | 2/2005 | Mizzen et al. |
| 2005/0037342 A1 | 2/2005 | Mathur et al. |
| 2005/0042600 A1 | 2/2005 | Hu et al. |
| 2005/0142541 A1 | 6/2005 | Lu et al. |
| 2005/0147621 A1 | 7/2005 | Higgins et al. |
| 2005/0159386 A1 | 7/2005 | Kieny et al. |
| 2005/0255460 A1 | 11/2005 | Lu et al. |
| 2005/0255468 A1 | 11/2005 | Ridder et al. |
| 2005/0260566 A1 | 11/2005 | Fischer et al. |
| 2006/0029943 A1 | 2/2006 | Hermonat et al. |
| 2006/0039919 A1 | 2/2006 | Chang et al. |
| 2006/0121516 A1 | 6/2006 | Norman et al. |
| 2006/0147906 A1 * | 7/2006 | Zwerschke .......... C07K 14/005 435/5 |
| 2006/0153864 A1 | 7/2006 | Gissmann et al. |
| 2006/0154238 A1 | 7/2006 | Hu et al. |
| 2006/0160069 A1 | 7/2006 | Chau et al. |
| 2006/0172285 A1 | 8/2006 | Patterson |
| 2006/0257849 A1 | 11/2006 | Zauderer |
| 2006/0269967 A1 | 11/2006 | Chen et al. |
| 2006/0286595 A1 | 12/2006 | Fischer et al. |
| 2007/0048833 A1 | 3/2007 | Sprecher et al. |
| 2007/0059319 A1 | 3/2007 | Carlson et al. |
| 2007/0065810 A1 | 3/2007 | Schlegel et al |
| 2007/0099199 A1 | 5/2007 | Lu et al. |
| 2007/0111266 A1 | 5/2007 | Sprencher et al. |
| 2007/0117167 A1 | 5/2007 | Malinowski et al. |
| 2007/0166699 A1 | 7/2007 | Zwerschke et al. |
| 2007/0190062 A1 | 8/2007 | Malinowski et al. |
| 2007/0190529 A1 | 8/2007 | Ridder et al. |
| 2008/0038738 A1 * | 2/2008 | Weigum .............. A61B 5/0059 435/6.12 |
| 2008/0267982 A1 | 10/2008 | Kiselev et al. |
| 2009/0047660 A1 | 2/2009 | Lu et al. |
| 2009/0075377 A1 | 3/2009 | Lu et al. |
| 2009/0104597 A1 | 4/2009 | Gombrich et al. |
| 2009/0148864 A1 | 6/2009 | Fischer et al. |

FOREIGN PATENT DOCUMENTS

| | | |
|---|---|---|
| GB | 2379220 | 5/2003 |
| JP | 2002296274 | 10/2002 |
| JP | 2007503208 | 2/2007 |
| JP | 2007537705 | 12/2007 |
| TW | 95142312 | 11/2006 |
| TW | 100100781 | 1/2010 |
| TW | 201012932 | 4/2010 |
| TW | 201043958 | 12/2010 |
| WO | WO9700888 | 1/1997 |
| WO | WO9910375 | 3/1999 |
| WO | WO02/08764 | 1/2002 |
| WO | WO0204007 A2 | 1/2002 |
| WO | WO2004/022006 | 3/2004 |
| WO | WO2004085683 | 10/2004 |
| WO | WO2005008248 | 1/2005 |
| WO | 2005063286 | 7/2005 |
| WO | 2004013632 | 9/2005 |
| WO | WO2005088311 | 9/2005 |
| WO | WO2006083984 | 8/2006 |
| WO | WO2007059492 | 5/2007 |
| WO | WO2007095320 | 8/2007 |
| WO | WO2009042488 | 4/2009 |
| WO | 2009079192 | 6/2009 |
| WO | WO2009151632 | 12/2009 |
| WO | WO2009151633 | 12/2009 |
| WO | WO2010129821 | 11/2010 |
| WO | WO2011084598 | 7/2011 |

OTHER PUBLICATIONS

Guimaraes, et al. 2005. "Immunohistochemical expression of p16INK4a and bcl-2 according to HPV type and to the progression of cervical squamous intraepitheliallesions". J Histochem Cytochem. 53: 509-16).

Hagensee, et al. "Detection of Cervical Antibodies to Human Papillomavirus Type 16 (HPV-16) Capsid Antigens in Relation to Detection of HPV-16 DNA and Cervcal Lesions", The Jourrnal of Infectious Diseases 2000; 181: 1234-9.

Kiviat, et al. 1993. Specific human papillomavirus types as the causal agents of most cervical intraepithelial neoplasia: implications for current views and treatment. J Natl Cancer Inst 85: 934-35.

Koutsky, et al. 1992. A cohort study of the risk of cervical intraepithelial neoplasia grade 2 or 3 in relation to papillomavirus infection. N Engl J med 327:1272-1278. Abstract Only.

Kuroda, et al. 2005. The human papillomavirus E6 and E7 inducible oncogene, hWAPL, exhibits potential as a therapeutic target. Br J Cancer 92:290-3.

Li, et al. 2005. Regulation of apoptosis by papillomavirus E6 oncogene. World J Gastroenterol 11:931-37.

Longworth, et al., 2004. Pathogenesis of human papillomavirus in differentiating epithelia. Microbiol Mol Bioi Rev 68: 362-72.

Madrigal, et al. 1997. In vitro antigene therapy targeting HPV-16 E6 and E7 in cervical carcinoma. Gynecol Oncol 64: 18-25.

Meschede, et al. "Antibodies agains Early Proteins of Human Papillomaviruses as Diagnostic Markers for Invasive Cervical Cancer" Journal of Clinical Microbiology Feb. 1998, pp. 475-480.

Munoz, et al. 2003. Epidemiologic classification of human papillomavirus types associated with cervical cancer. N Engl J Med 348:518-27.

Park, et al. 1995. Molecular biology of cervical cancer and its precursors. Cancer 76: 1902-13.

Park, et al. "HPV-16-Related Proteins as the Serolgic Markers in Cervical Neoplasia", Gynecologic Oncology 69,47-55 (1998).

Parkin, et al. 1993. Estimates of the worldwide incidence of eighteen major cancers in 1985. Int J Cancer 54:594-606.

Sehr, et al. "A generic capture ELISA for recombinant proteins fused to glutathione S-transferase: validation for HPV serology" Journal of ImmunoloQical Methods 253 (2001) 153-162.

Solomon, et al. 2002. The 2001 Bethesda Systems. Terminology for reportinQ results of cervical cytoloQY. JAMA 287:2114-19.

Studentsov, et al. "Polymer-Based Enzyme-Linked Immunosorbent Assay Using Human Papillomavirus Type 16 (HPV16) Virus-Like Particles Detects HPV16 Clade-Specific Serologic Responses", Journal of Clinical Microbiology Jul. 2003 pp. 2827-2834.

Sun, et al., "Comparison of Peptide Enzyme-Linked Immunosorbent Assay and Radioimmunoprecipitation Assay with In Vitro-Translated Proteins for Detection of Serum Antibodies to Human Papillomavirus Type 16 E6 and #7 Proteins" Journal of Clinical MicrobioloQY Sep. 1994 pp. 2216-2230.

Tjiong, et al. "Antibodies agains Human Papillomavirus Type 16 and 18 E6 and E7 Proteins in Cervicovaginal Washings and Serum of Patients with Cervical Neoplasia" Virallmjmunolgy vol. 14, No. 4, 2001 pp. 415-424.

(56) References Cited

OTHER PUBLICATIONS

Veress, et al. "Human Papillomavirus DNA and Anti-HPV Secretory IgA Antibodies in Cytologically Normal Cervical Specimens" Journal of Medical Virology 43:201-207-(1994).

Viscidi, et al. 1993. Serologic response in human papillomavirus-associated invasive cervical cancer. Int. J. Cancer 55:780-784.

Walboomers, et al. "Human Papillomavirus is a Necessary Cause of Invasive Cervical Cancer Worldwide", Jouranl of PatholoQv 189: 12-19 (1999).

Wang, et al. "Cervical Mucus Antibodies against Human Papillomavirus Type 16, 18, and 33 Capsids in Relation to Presence of Viral DNA" Journal of Clinical Microbiology Dec. 1996 pp. 3056-3062.

Zumbach, et al "Antibodies Against Oncoproteins E6 and E7 of Human Papillomavirus Types 16 and 18 in Cervical-Carcinoma Patents from Russia", Int. J. Cancer 85, 313-318 (2000) [Publication of the International Union Against Cancer].

Fitzgerald Industries International Inc., Product Data Sheet for Monoclonal Antibody to human Papillomavirus (Early Protein), Human, Clone BF7. 2006.

Wang et al., Am J. Surg Patholo. 2004, vol. 28. No. 7, pp. 901-908 Detection of Human Papillomavirus DNA and Expression of p16, Rb, p53 proteins in small cell carcinomas of the uterine cervix.

Gabriella et al., BMC Cancer. 2007, vol. 7, pp. 25. Characterization of antibodies in single-chain format against the E7 oncoprotein of the human papillomavirus type 16 and their improvement by mutagenesis.

Arbyn, M., P. Sasieni, C. J. L. M. Meijer, C. Clavel, G. Koliopoulos, and J. Dillner. 2006. Chapter 9: Clinical applications of HPV testing: A summary of meta-analyses. Vaccine 24:78-89.

Castle, P. E., J. Dockter, C. Giachetti, F. A. Garcia, M. K. McCormick, A. L. Mitchell, E. B. Holladay, and D. P. Kolk. 2007. A cross-sectional study of a prototype carcinogenic human papillomavirus E6/E7 messenger RNA assay for detection of cervical precancer and cancer. Clinical cancer research : an official journal of the American Association for Cancer Research 13:2599-2605.

Cuschieri, K., and N. Wentzensen. 2008. Human Papillomavirus mRNA and p16 Detection as Biomarkers for the Improved Diagnosis of Cervical Neoplasia. Cancer Edidemiol. Biomarkers Prev. 17:2536-2545.

Dehn, D., K. C. Torkko, and K. R. Shroyer. 2007. Human Papillomavirus Testing and Molecular Markers of Cervical Dysplasia and Carcinoma. Cancer Cytopathology 111:1-14.

O'Sullivan, J. P., R. P. A'Hern, P. A. Chapman, L. Jenkins, R. Smith, and A. a. Nafussi. 1998. A case-control study of truepositive versus false-negative cervical smears in women with cervical intraepithelial neoplasia (CIN) III. Cytopathology 9:155-161.

Yim, E.-K., and J.-S. Park. 2006. Biomarkers in Cervical Cancer. Biomarker Insights 1:215-225.

Schiffman, M., A. G. Glass, N. Wentzensen, B. B. Rush, P. E. Castle, D. R. Scott, J. Buckland, M. E. Sherman, G. Rydzak, P. Kirk, A. T. Lorincz, S. Wacholder, and R. D. Burk. 2011. A long-term prospective study of type-specific human papillomavirus infection and risk of cervical neoplasia among 20,000 women in the Portland Kaiser Cohort Study. Cancer epidemiology, biomarkers & prevention : a publication of the American Association for Cancer Research, cosponsored by the American Society of Preventive Oncology 20:1398-1409.

Schweizer, J., P. S. Lu, C. W. Mahoney, M. Berard-Bergery, M. Ho, V. Ramasamy, J. E. Silver, A. Bisht, Y. Labiad, R. B. Peck, J. Lim, J. Jeronimo, R. Howard, P. E. Gravitt, and P. E. Castle. 2010. Feasibility study of a human papillomavirus E6 oncoprotein test for diagnosis of cervical precancer and cancer. Journal of clinical microbiology 48:4646-4648.

Stoler, M. H., P. E. Castle, D. Solomon, and M. Schiffman. 2007. The Expanded Use of HPV Testing in Gynecologic Practice per ASCCP=Guided Manmagement Requires the Use of Well-Validated Assays. American Journal of Clinical Pathology 127:335-337.

Woodman, C. B. J., S. I. Collins, and L. S. Young. 2007. The natural history of cervical HPV infection: unresolved issues. Nature Reviews Cancer 7:11-22.

SJ Lee et al., J Immunol (2001); 167; 497-504. "Both E6 and E7 Oncoproteins of Human Papillomavirus 16 Inhibit IL-IS-Induced IFN-'Y Production in Human Peripheral Blood Mononuclear and NK Cells."

S Vazquez-Vega et al., BMC Cancer (2007). 7(Suppl 1), A21. "Expression of viral and cellular cycle proteins and proteinases in cervical carcinoma cell lines as possible immunocytochemical markers of malignant phenotype."

J Doorbar, (2006) Clinical Science 1, 10, 525-541. "Molecular biology of human papillomavirus infection and cervical cancer."

M Fiedler et al., (2004) The FASEB Journal vol. 18 pp. 1120-1122. "High level HPV-16 E7 oncoprotein expression correlates with reduced pRb-levels in cervical biopsies."

KH Kim et al., (1994) Yonsei Medical Journal vol. 35, No. 1, pp. 1-9. "Expression and Localization of Human Papillomavirus Type 16 E6 and E7 Open Reading Frame Proteins in Human Epidermal Keratinocyte."

M Fiedler et al., (2005) Journal of General Virology, 86, 3235-3241. "Expression of the high-risk human papillomavirus type 18 and 45 E7 oncoproteins in cervical carcinoma biopsies."

E Guccione et al., (2002) Virology 283, 20-25. "Comparative Analysis of the Intracellular Location of the High- and Low-Risk Human Papillomavirus Oncoproteins."

H Valdovinos-Torres et al., (2008) The Open Virology Journal vol. 2. 15-23. "Different Isoforms of HPV-16 E7 Protein are Present in Cytoplasm and Nucleus."

T Li et al., (2001) Carcinogenesis vol. 22. No. 6 pp. 929-934. "Human papillomavirus type 16 is an important infections factor in the high incidence of esophageal cancer in Anyang area of China."

Blevins et al., Applied and Environmental Microbiology 2007, pp. 1501-1513. "Adaptation of a Luciferase Gene Reporter Aand lac ExpressionSystem to Borrelia burgdorferi."

EA Mirecka et al., (2006) Protein Expression and Purification 48, 281-291. "Expression and purification of His-tagged HPV16 E7 protein active in pRb binding/".

MS Lechner et al., (1994) Journal of Virology, Jul. 1994, p. 4262-4273. "Inhibition of p53 DNA Binding by Human Papillomavirus E6 Proteins."

B Bjorndal et al., (2003) Protein Expression and Purification 31 (2003) 47-55. "Expression and purification of receptor for activated C-kinase 1 (RACKI)."

ND Christensen et al., (1996) Virology 223, 174-184. "Surface Conformational and Linear Epitopes on HPV-16 and HPV•18 L1 Virus-like Particles as Defined by Monoclonal Antibodies".

Y Nomine et al., (2001) Protein Engineering vol. 14 No. 4 pp. 297-305, "A strategy for optimizing the monodispersity of fusion proteins: application to purification of recombinant HPV E6 oncoprotein."

ND Christensen et al., (1994) Journal o/General Virology (1994), 75, 2271-2276. "Assembled baculovirus-expressed human papillomavirus type 11 LI capsid protein virus-like particles are recognized by neutralizing monoclonal antibodies and induce high titres of neutralizing antibodies."

T Oltersdorf et al., (1987) J. gen. Viral. (1987), 68, 2933-2938. "Identification of Human Papillomavirus Type 16 E7 Protein by Monoclonal Antibodies."

P Di Bonito et al., (2006) Infectious Agents and Cancer 2006, 1:6. "Serum antibody response to Human papillomavirus (HPV) infections detected by a novel ELISA technique based on denatured recombinant HPVI6 LI, L2, E4, E6 and E7 proteins."

JF Kearney et al., (1979) The Journal of Immunology, V 123 No. 4 p. 1548-1550. "A New Mouse Myeloma Cell Line That has Lost Immunoglobulin Expression but Permits the Construction of Antibody-Secreting Hybrid Cell Lines."

K Seedorf et al., The EMBO Journal 1987, vol. 6, pp. 139-144. Identification of Early Proteins of the Human Papilloma Viruses Type 16 (HPV 16) and Type 18 (HPV 18) in Cervical Carcinoma Cells.

(56) References Cited

OTHER PUBLICATIONS

D Patel et al., (1989) J. gen. Virol. (1989),70,69-77. "Reactivities of Polyclonal and Monoclonal Antibodies Raised to the Major Capsid Protein of Human Papillomavirus Type 16."
S-H Kee et al., (1997) J. Korean Soc. Microbiol., vol. 32, No. 3, "Generation of Monoclonal Antibodies Against Human Papillomavirus Type16 E7 Protein: Usefulness for Various E7 Detection Systems."
AK Graham et al., (1991) Clin Pathol 1991;44:96-101. "Simultaneous in situ genotyping and phenotyping of human papillomavirus cervical lesions: Comparative sensitivity and specificity."
HG Kochel et al., (1991) Inl. J. Cancer: 48, 682-688. "Occurrence of Antibodies to Lt, L2, E4 and E7 Gene Products of Human Papillomavirus Types 6b, 16 and 18 Among Cervical Cancer Patients and Controls."
AK Ghosh et al., (1993) Int. J. Cancer: 53. 591-596. "Serological Responses to HPV 16 in Cervical Dysplasia and Neoplasia: Correlation of Antibodies to E6 With Cervical Cancer."
SA Jenison et al., (1990) The Journal of Infectious Disease162:60-69. "Evidence of Prevalent Genital-Type Human Papillomavirus Infections in Adults and Children."
T Fule et al., (2006) Virology 348, 289-396. "The presence of human papillomavirus 16 in neural structures and vascular endothelial cells."
Tommasino et al., Oncogene 1993, vol. 8, pp. 195-202. HPV16 E7 Protein Associates with the Protein Kinase p22 CDK2 and Cyclin A.
De Villiers et at., Virology 2004, vol. 324, pp. 17-27. "Classification of Papillomaviruses".
Banks et al., J. gen. Virol. 1987, vol. 68, pp. 1351-1359, "Identification of human papillomavirus type 18 E6 polypeptide in cells derived from human cervical carcinomas".
Thermo Scientific, Product Data Sheet for Human Papilloma Virus type 16-E7 (HPV 16-e7) Ab-1 (TVG701Y) Mouse Monoclonal Antibody. Dec. 8, 2011.
BioDesign Internation, Product Data Sheet for MAb to HPV16 E7 protein 716-218. Feb. 1, 2006.
BioDesign Internation, Product Data Sheet for MAb to HPV16 E7 protein 716-325. Aug. 3, 2005.
Chemicon International, Product Data Sheet for Mouse anti-human Papilloma Virus 16,18 E6 (C1P5) Monoclonal Antibody. Nov. 10, 2000.
Dako, Product Data Sheet for Monoclonal Mouse anti-Human Papillomavirus Clone K1H8. 2010.
G Volgareva et al., BMC Cancer 2004, 4:58. "Protein p16 as a marker of dysplastic and neoplastic alterations in cervical epithelial cells."
Digene Corporation, "hc2 HPV DNA Test," Ref. 5198-1220, 2007, 56 pages.
Matlashewski G., et al. The expression of human papillomavirus type 18E6 proteins in bacteria and the production of anti-E6 antibodies J Gen Virol (1986) 67: 1909-1916.
Radhakrishna pillai et al 1998 High-risk human papillomavirus infection and E6 protein expression in lesions of the uterine cervix Pathobiology 66(5) 240-246.
Ressler et al 2007 High-risk human popillomavirus E7 oncoprotein detection in cervical squamous cell carcinoma Clin Cancer Res 13(23) 7067-7072.
Androphy et al 1987 Identification of the HPV-16 E6 protein from transformed mouse cells and human cervical carcinoma cell lines EMBO 6(4) 989-992.
Andersson et al 2006 Expression of E6/E7 mRNA from high rish human papillomavirus in relation to CIN grade, viral load and p16INK4a Int J oncology 29:70-711.
Keegan et al 2009 Comparison of HPV detection technologies: Hybrid capture 2, preTect HPV prooer and analysis of HPV DNA viral load in HPV 16, HPV 18 and HPV 33 E6/E7 mRNA.
Inoue et al 1990 A novel monoclonal antibody against squamous cell carcinoma Jpn J Cancer res 81:176-182.
La Selvey et al., 1992 Journal of Virological Methods, 37, 119-128. An ELISA capture assay for the E7 transforming proteins of HPV16 and HPV18.
H Griesser et al., 2004 Analyt Quant Cytol Histol 26, 241-245. "Correlation of Immunochemical Detection of HPV L1 capsid protein in Pap Smears with Regression of High-Risl HPV Positive Milk/Moderate Dysplasia."
TIPO Search Report and Communication for Taiwan Invention Patent Application No. 095142312, Mar. 24, 2012. English search report on p. 1.
TIPO Search Report and Communication for Taiwan Invention Patent Application No. 098119611, Mar. 22, 2012. English search report on p. 1.
TIPO Search Report and Communication for Taiwan Invention Patent Application No. 098119612, Mar. 13, 2012. English search report on p. 1.
Volgareva et al., Protein p16 as a marker of dysplastic and neoplastic alterations in cervical epithelial cells. BMC Cancer 2004, 4:58. pp.
Liu et al., Preparation of monoclonal antibodies against human papillomavirus 16 E6 protein. Journal of Monoclonal Antibody, vol. 11 No. 3-4, Dec. 1995. English abstract on p. 3.
Su et al., Expression of human papillomavirus type 16 E6 oncogene production of monoclonal antibodies against HPV 16 E6 protein. Journal of Chinese Microbiology and Immunology, vol. 13 No. 3, 1993. English abstract on p. 4.
Wang et al., Expression of human papillomavirus type 16 L1 and construction of hybridoma cell strain of human papillomavirus type 16 L1 monoclonal antibody. Chin J. Endemiol, Jan. 20, 2007, vol. 26, No. 1. English abstract on p. 1.
Arbyn et al., 2009. J Cell Mol Med. vol. 13 No. 4 648-659. "Triage of women with equivocal or low-grade cervical cytology results: a meta-analysis of the HPV test positivity rate".
Andersson et al., 2006. International Journal of Oncology 29: 705-711. "Expression of E6/E7 mRNA from 'high risk' human papillomavirus in relation to CIN grade, viral load and p16INK4a".
Balasubramanian et al., Cancer Epidemiol Biomarkers Prev 2009;18:3008-3017. "Evaluation of an ELISA for p16INK4a as a Screening Test for Cervical Cancer".
Cardenas-Turanzas et al., Gyn Oncology 107 (2007) S138-S146. "The clinical effectiveness of optical spectroscopy for the in vivo diagnosis of cervical intraepithelial neoplasia: Where are we?".
Castle et al., 2010. AACCP. Benefits and risks of HPV testing in cervical cancer screening See Online/Articles DOI:10.1016/S1470-2045(09)70360-2.
Castle et al., American Journal of Obstetrics & Gynecology Oct. 2007 "Risk assessment to guide the prevention of cervical cancer".
Choi et al., Biosensors and Bioelectronics 20 (2005) 2236-2243. "Adenoviral p53 effects and cell-specific E7 protein-protein interactions of human cervical cancer cells".
Cole et al., Journal of Virology, Jun. 1986, vol. 58. No. 3. p. 991-995. "Genome Organization and Nucleotide Sequence of Human Papillomavirus Type 33, Which Is Associated with Cervical Cancer".
Cole et al., J. Mol. Biol. (1987) 193,599-608. "Nucleotide Sequence and Comparative Analysis of the Human Papillomavirus Type 18 Genome Phylogeny of Papillomaviruses and Repeated Structure of the E6 and E7 Gene Products".
Sawaya 2008 Annals of Internal Medicine vol. 148 • No. 7 p. 557 "Adding Human Papillomavirus Testing to Cytology for Primary Cervical Cancer Screening: Shooting First and Asking Questions Later".
Fuchs et al., Journal of Virology, May 1986, p. 626-634. vol. 58, No. 2 "Epidermodysplasia Verruciformis-Associated Human Papillomavirus 8: Genomic Sequence and Comparative Analysis".
Garcia-Alai et al., Biochemistry 2007, 46, "High-Risk HPV E6 Oncoproteins Assemble into Large Oligomers that Allow Localization of Endogenous Species in Prototypic HPV-Transformed Cell Lines".
Gravitt et al., Vaccine 265 (1008) K42-K52. "New Technologies in Cervical Cancer Screening".

(56) References Cited

OTHER PUBLICATIONS

Kulasingam et al., Obstetrics & Gynecology vol. 107, No. 2, Part 1, Feb. 2006 Cost-effectiveness of Extending Cervical Cancer Screening Intervals Among Women With Prior Normal Pap Tests:.
Mao et al., Int. J. Cancer: 120,2435-2438 (2007) "Evaluation of a new p16INK4a ELISA test and a high-risk HPV DNA test for cervical cancer screening: Results from proof-of-concept study".
Molden et al., Int. J. Cancer: 114,973-976 (2005) "Predicting CIN2 when detecting HPV mRNA and DNA by PreTect HPV-Proofer and consensus PCR: a 2-year follow-up of women with ASCUS or LSIL Pap smear".
Marimatsu et al., Am J Clin Pathol 2005;123:716-723 "High-Throughput Cervical Cancer Screening Using Intracellular Human Papillomavirus E6 and E7 mRNA Quantification by Flow Cytometry".
NCCN Clinical Practice Guidelines in Oncology™ v.2. 2007 Cervical Cancer Screening.
Negri et al., Am J Surg Pathol 2008;32:1715-1720 "p16ink4a and HPV L1 Immunohistochemistry is Helpful for Estimating the Behavior of Low-grade Dysplastic Lesions of the Cervix Uteri".
Norchip et a;., 22nd. International Papillomavirus Conference, Vancouver, BC, Canada, Apr. 30-May 6, 2005 "Persistent transforming HPV infection may correlate with persistent histologically defined CIN II+ Summary of studies by Frank Karlsen and Hanne Skomedal".
Trope et al., Journal of Clinical Microbiology, Aug. 2009, p. 2458-2464. "Pe rformance of Human Papillomavirus DNA and mRNA Testing Strategies for Women with and without Cervical Neoplasia".
Schiffman et al., Arch Pathol Lab Med—vol. 127, Aug. 2003. "Findings to Date From the ASCUS-LSIL Triage Study (ALTS)." pp. 946-949.
Woodman et al., "The natural history of cervical HPV infection: unresolved issues." Nature Review Cancer, vol. 7 | Jan. 2007 | 11.
Ronco et al., BMC Women's Health 2008, 8:23. "New paradigms in cervical cancer prevention: opportunities and risks">.
Talora et al., Genes Dev. 2002 16: 2252-2263. Specific downmodulation of Notch1 signaling in cervical cancer cells is required for sustained HPV-E6/E7 expression and late steps of malignant transformation.
Tungteakkhun wr al., Arch Virol (2008) 153:397-408. "Cellular binding partners of the human papillomavirus E6 protein".
Sellor et al., Journal of Lower Genital Tract Disease, vol. 15, No. 2, 2011, 169-176. Association of Elevated E6 Oncoprotein With Grade of Cervical Neoplasia Using PDZ InteractionYMediated Precipitation of E6.
Ronco et al., "Effi cacy of human papillomavirus testing for the detection of invasive cervical cancers and cervical intraepithelial neoplasia: a randomised controlled trial:." Published Online Jan. 19, 2010.
Schneider-Gadicke et al., The EMBO Journal vol. 5 No. 9 pp. 2285-2292, 1986. "Different human cervical carcinoma cell lines show similar transcription patterns of human papillomavirus type 18 early genes."
Wentzensen et al., Disease Markers 23 (2007) 315-330. "Biomarkers in cervical cancer screening."
Molder et a;., Cancer Epidemiology Biomarkers and Prevention. 2005, 14, p. 367. Comparison of Human Papillomavirus Messeger DNA and DNA detection: a crodd sectional study of 4136 wk e > 30 years of age with a 2, year fikkiw-up of high=grade squamous intraepitehlial Lesion.
Sawaya et al., 2005. www.nejm.org May 10, 2007. "HPV Vaccination—More Answers, More Questions."
Perez et al., 2009. 25th International Papillomavirus Conference, Sweden. "Detection of HPV E6/E7 Oncoporteins in Cervical Cancer."
Parkin et al., Int. J. Cancer: 80, 827-841 (1999). "Estimates of the Worldwide Incidence of 25 Major Cancers in 1990."
Schneider et al., 1991 Int. j. Gynecol Pathol. 10:1-14 "Prevalence of Human Papillomavirus Genomes in Tissue from the Lower Genital Tract as Detected by Molecular in situ hybridization."
Segnan et al., 1994 European Journal of Cancer vol. 30, 873-875. "Cervical cancer screening. Human benefits and human costs in the evaluation of screening programmes."
Partridge et al., 2008 J. National Compr. Cancer Network 6: 58-82. Abstract only.
Heck et al., 1992 Proc. Natl. Acad. Sci. USA vol. 89, pp. 4442-4446, May 1992. "Efficiency of binding the retinoblastoma protein correlates with the transforming capacity of the E7 oncoproteins of the human papillomaviruses."
Chellappan et al., 1992 Proc. Natl. Acad. Sci. USA vol. 89, pp. 4549-4553, May 1992. "Adenovirus EIA, simian virus 40 tumor antigen, and human papillomavirus E7 protein share the capacity to disrupt the interaction between transcription factor E2F and the retinoblastoma gene product.".
Dyson et al., Science 1989. 243: 934-937. "The Human Papilloma Virus-16 E7 Oncoprotein Is Able to Bind to the Retinoblastoma Gene Product."
Zerfass et al., J. Virol. 1995, 69(10):6389. "Sequential activation of cyclin E and cyclin A gene expression by human papillomavirus type 16 E7 through sequences necessary for transformation."
Zerfass-Thome et al., 1996 Oncogene 13:2323-2330. "Inactivation of the cdk inhibitor p27KIP1 by the human papillomavirus type 16 E7 oncoprotein."
Saint, M., G. Gildengorin, and G. F. Sawaya. 2005. Current Cervical Neoplasia Screening Practices of Obstetriciaqn/Gynecologists in the US. Am. J. Obstet. Gynecol. 192:414-421.
Non-final Office Action for U.S. Appl. No. 12/456,054 dated Sep. 25, 2012.
Final Office Action for U.S. Appl. No. 12/456,053 dated Sep. 24, 2012.
JH Joen et al., "Immunocytochemical detection of HPV16E7 in cervical smear." 2007. Experimental and Molecular Medicine, vol. 39, No. 5, 621-628.
C Liang et al., "Biomarkers of HPV in Head and Neck Squamous Cell Carcinoma." 2012, Cancer Research. Published online Sep. 18, 2012.
D Holzinger et al., "Viral RNA Patterns and High Viral Load Realiably Define Oropharynx Carcinomas wit hActive HPV16 Involvement." 2012, Cancer Research. Published online Sep. 18, 2012.
AG Ostor et al., "Natural History of Cervical Intraepithelial Neoplasia: A Critical Review." 1993 International Journal of Gyncological Pathology . 12:186-192.
Non-final Office Action for U.S. Appl. No. 12/590,747 dated Aug. 15, 2012.
Kashmiri et al., Methods. 2005; 36:25-34.
Tamura et al., Journal of Immunology. 2000; 164:1432-1441.
Greenspan et al., Nature Biotechnology. 1999; 7:936-937.
Gillison et al., Journal of National Cancer Institute. 2008; 100:407-420.
Wu et al., Journal of General Virology. 2006; 87, 1181-1188.
http://www.biology-online.org/dictionary/Native_protein; Mar. 16, 2010.
Notice of Allowance for U.S. Appl. No. 12/456,076 dated Aug. 1, 2012.
Examiner-Initiated Interview Summary and Amendment after Final initiated by the Examiner for U.S. Appl. No. 12/456,076 dated Aug. 1, 2012.
Advisory Action for U.S. Appl. No. 12/456,054 dated Jun. 13, 2012.
Dorland's Pocket Medical Dictionary, P420, 25th Edition, 1995, W,B, Saunders Company. Philadelphia, Pennsylvania, 19106.
Final Office action for U.S. Appl. No. 12/456,076 dated May 24, 2012.
Tindle RW et al., 1990 Journal of General Virology. 71, 1347-1354. "Identification of B epitopes in human papillomavirus type 16 E7 open reading frame protein."
Santa Cruz Biotechnology, Inc. Product Data Sheet for sc-18114 E6-AP (C-19). 2006.
China Patent Office Communication dated Apr. 1, 2013 for Application No. 200980131078.4.

(56) References Cited

OTHER PUBLICATIONS

China Patent Office Communication dated Mar. 13, 2013 for Application No. 200980131077.X.
Non-final Office action for U.S. Appl. No. 12/456,053 dated Apr. 6, 2012.
Final Office action for U.S. Appl. No. 12/456,054 dated Apr. 16, 2012.
EPO Communcation for Application No. 12164498.3 dated on Sep. 28, 2012.
MA Romanos et al., 1995. Production of a phosphorylated GST::HPV-6 E7 Fusion Protein Using a Yeast Expression Vector and Glutathione S-transferase Fusions. Gene. 152, 137-138.
Partial European Search Report for Application No. 12164498, dated Sep. 19, 2012.
T. Ristriani et al., 2001. "Specific Recognition of Four-way DNA Junctions by the C-terminal Zinc-binding Domain of HPV Oncoprotein E6." J. Mol. Biol. 305, 729-739.
KLMC Franken et al., 2000. "Purificaiton of His-Tagged PRoteins by Immobilized Chelate Affinity Chromatography: The Benefits from the Use of Organic Solvent." Protein Expression and Purification 18, 95-99.
Y. Nomine et al., 2001. "A strategy for optimizing the monodispersity of fusion proteins: application to purification of recombinant HPV E6 oncoprotein." Protein Engineering. 14, No. 4 pp. 297-305.
JA DeVoti et al., 2004. "Failure of Gamma Interferon but Not Interleukin-10 Expression in Response to Human Papillomavirus Type 11 E6 PRotein in Respiratory Papillomatosis." Clinical and Vaccine Immunology 11(3) 538-547.
TIPO Search Report and Communication for Taiwan Invention Patent Application No. 098119612, Oct. 5, 2012. Search Report Brief is on p. 1.
J Melnikow et al., 1998. "Natural history of Cervical Squamous Intraepithelial Lesions: A meta-Analysis." 1998 vol. 92, No. 4, pp. 727-735.
European Patent Office Communication dated Oct. 23, 2012 for Application No. 09762928.1, PCT/US2009003537.
Non-final Office Action for U.S. Appl. No. 13/029,131 dated Nov. 9, 2012.
European Patent Office Communication dated Jan. 30, 2013 for Application No. 12164498.3-2402/2522756.
Non-final Office Action for U.S. Appl. No. 13/585,509 dated Jan. 15, 2013.
Qiao et al., 2008. "A New HPV-DNA Test for Cervical-Cancer Screening in Developing Regions: a Cross-Sectional Study of Clinical Accuracy in Rural China." Lancet Oncology 9: 929-936.
Zhao et al., 2010. "Performance of High-Risk Human Papillomavirus DNA Testing as a Primary Screening for Cervical Cancer: a Pooled Analysis of Individual Patient Data from 17 Population-Based Studies from China." Lancet Oncology 11: 1160-1171.
Zhao et al., 2011. "Pooled Analysis of a Self-Sampling HPV DNA Test as a Cervical Cancer Primary Screening Method." JNCO 104: 1-11.
Arbyn et al., 2010. "HPV-Based Cervical-Cancer Screening in China." World Health Organization GLOBOCAN 2008. Published online Nov. 12, 2010. http://globocan.iarcfr/.
Wong et al., 2011. "Efficacy of Abbott Real Time High Risk HPV Test in Evaluation of Atypical Squamous Cells of Undetermined Significance from an Asian Screening Population." Journal of Clinical Virology 51, 136-138.
Petignat et al., 2012. "Is It Time to Introduce HPV Seld-Sampling for Primary Cervical Cancer Screening?" Editorial, JNCI. 104 (3): pp. 1-2.
Japan Patent Office Communication dated Apr. 2, 2013 for Application No. 2011-513504.
Final Office Action for U.S. Appl. No. 12/456,054 dated May 14, 2013.
Taiwan Patent Office Communication dated Apr. 8, 2013 for Application No. 100100781.
Taiwan Patent Office Communication dated Apr. 3, 2013 for Application No. 095142312.
Li et al. 2001. Carcinogenesis vol. 22 pp. 929-934. "Human Papillomavirus Type 16 is an Important Infectious Factor in the High Incidence of Esophageal Cancer in Anyang Area of China."
Guccione et al. 2002. Virology vol. 293 pp. 20-25. "Comprative Analysis of the Intracellular Location of the High- and Low-Risk Human Papillomavirus Oncoproteins."
Mar. 6, 2016 European Patent Office Communication for App. No. 15187228.0.
Jun. 5, 2015 USPTO Notice of Allowance for U.S. Appl. No. 13/520,021.
Feb. 8, 2016 USPTO Non-final Office Action for U.S. Appl. No. 12/456,055.
Jan. 6, 2016 USPTO Non-final Office Action for U.S. Appl. No. 14/335,531.
May 13, 2015 Japan Patent Office Communication for App. No. 2012-548021.
May 8, 2015 European Patent Office Communication for App. No. 10722861.0.
Jun. 5, 2015 China Patent Office Communication for App. No. 201080020175.9.
Jan. 26, 2016 China Patent Office Communication for App. No. 200980131077.x.
May 7, 2015 China Patent Office Communication for App. No. 200980131077.x.
Oct. 2, 2015 China Office Communication for App. No. 201080060962.6.
Dec. 18, 2014 Japan Office Communication for App. No. 2012-509989.
Notice of Allowance, U.S. Appl. No. 12/590,747. Sep. 30, 2014.
Notice of Allowance, U.S. Appl. No. 13/319,312. Oct. 1, 2014.
European Patent Office Communication, EP App. No. 09762929.9, Oct. 13, 2014.
China Patent Office Communication, CN App. No. 201080060962.6, Oct. 17, 2014.
China Patent Office Communication, CN App. No. 200980131078.4, Oct. 30, 2014.
China patent Office COmmunication, CN App. No. 201080020175.9, Nov. 15, 2014.
Non-Final Office Action, U.S. Appl. No. 13/520,021, Nov. 26, 2014.
Zhou et el., 1997. "Differential Diagnosis of Infections with Swine Transmissible Gastroenteritis virus and Procine Respiratory coronavirus using fixed-cell blocking ELISA." China Journal of Veterinarian 23 (12) 5-7.
Erdile et al., 2001. "Whole cell ELISA for detection of tumor antigen expression in tumor samples." Journal of Immunological Methods 258, 47-53.
China Patent Office Communication, CN App. No. 200980131077.X, Oct. 11, 2014.
Final Office action for U.S. Appl. No. 13/319,312 dated Jul. 24, 2014.
Final Office action for U.S. Appl. No. 12/590,747 dated Jul. 23, 2014.
Final Office action for U.S. Appl. No. 12/456,055 dated Sep. 9, 2014.
European Patent Office Communication for EPO Patent App. No. 09762929910842601.6 dated Jul. 14, 2014.
European Patent Office Communication for EPO Patent App. No. 12164498.3 dated Jun. 26, 2014.
European Patent Office Communication for EPO Patent App. No. 09762928.1 dated Aug. 26, 2014.
Japan Patent Office Communication for JP Patent App. No. 2011-513504 dated May 2, 2014.
Japan Patent Office Communication for JP Patent App. No. 2012-548021 dated Jul. 15, 2014.
China patent Office Communication for CN Patent App. No. 201080020175.9 dated May 28, 2014.
Notice of Allowance for U.S. Appl. No. 12/456,053 dated Jun. 13, 2014.
Notice of Allowance for U.S. Appl. No. 12/456,054 dated Jun. 13, 2014.

(56) References Cited

OTHER PUBLICATIONS

Non-final Office action for U.S. Appl. No. 12/456,055 dated Mar. 21, 2014.
Non-final Office action for U.S. Appl. No. 12/590,747 dated Mar. 26, 2014.
Final Office action for U.S. Appl. No. 13/520,021 dated Apr. 14, 2014.
Apgar et al., "The Bethesda System Terminology." Am Fam Physician 2003; 68: 1992-1998.
Kovanda et al., "Characterization of a Novel Cutaneous Human Papillomavirus Genotype HPV-125." PLosOne 2011; vol. 6 e22414Vol.
Narechania et al., "Phylogenetic incongruence among Oncogenic Genital Alpha Human Papillomaviruses." J. Virol. 2005, 79(24): 15503.
Rudikoff et al., "Single amino acid substitution altering antigen-binding specificity." Proc. Natl. Acad. Sci 1982 vol. 79 1979-1982.
European Patent Office Communication for EPO Patent App. No. 097629299 dated Feb. 27, 2014.
Liu et al., "Fixed-cell immunoperoxidase Technology." China Academic Journal, Production Technology. 1993 vol. 23 No. 2 pp. 37-38.
US Patent Office non-final Office action for U.S. Appl. No. 13/319,312, Feb. 28, 2014.
Pavai et al., Romanian Journal of Morphology and Embryology 2006, 47(3): 229-234. "Comparative detection of high-risk HPV (16, 18, 33) in ervical bioptic material of County Hospital of Tg. Mures."
Pillai et al., Cancer Epidemiology Biomarkers & Prevention 1996; 5: 329-335. The presence of human papillomavirus-16/-18 E6, p53, and Bcl-2 protein in cervicovaginal smears from patients with invasive cervical caner.
Dec. 20, 2013 USPTO Non-Final Office Action dated Dec. 20, 2013 for U.S. Appl. No. 13/520,021.
Caceres-Cortes et al.,Implication of Tyrosine Kinase Receptor and Steel Factor in Cell Density-dependent Growth in Cervical Cancers and Leukemias. Cancer Research. 2001;61:6281-6289.
European Patent Office Communication dated Oct. 28, 2013 for Application No. 12164498.3-1404.
Sep. 18, 2013 USPTO Non-Final Office Action for U.S. Appl. No. 12/456,053.
Sep. 30, 2013 USPTO Non-Final Office Action for U.S. Appl. No. 12/456,054.
Sep. 30, 2013 USPTO Final Office Action for U.S. Appl. No. 12/590,747.
Aug. 30, 2013 EPO Office communication for EPA No. 09762928.1.
Sep. 9, 2013 USPTO Communication for U.S. Appl. No. 13/520,021.
Fiedler et. al., 2004 FASEB Journal express article. High Level HPV-16 E7 oncoprotein expression correlates with reduced pRb-levels in cervical biopsies.
European Patent Office Communication dated Jun. 6, 2013 for Application No. 10842601.6.
European Patent Office Communication dated Jul. 18, 2013 for Application No. 10772861.0.
Non-final Office action dated Jul. 3, 2013 for U.S. Appl. No. 12/456,055.
Santer et el., 2007 Carcinogenesis, vol. 28 No. 12 pp. 2511-2520. "Human papillomavirus type 16 E7 oncoprotein inhibits apoptosis mediated by nuclear insulin-like growth factor-binding protein-3 by enhancing its ubiquitin/proteasome-dependent degradation."
Non-final Office action dated Jul. 11, 2013 for U.S. Appl. No. 13/585,509.
Lie et al., 1999 Int J Gynecol Pathol 18(1): 5-11."Expression of p53, MDM2, and p21 proteins in high-grade cervical intraepithelial neoplasia and relationship to human papillomavirus infection."
Park et al., 1998 "HPV-16-releated proteins as the serologic markers in cervical neoplasis." Gynecologic oncology 69, 47-55.

Zhao et al., 2013 Cancer Prevention Research. Published OnlineFirst Jul. 22, 2013. "An Evaluation of Novel, Lower-Cost Molecular Screening Test for Human Papillomavirus in Rural China."
Shi et al., 2009 American Journal of Epidemiology vol. 170 No. 6. 708-716. "Human papillomavirus testing for cervical cancer screening: results from a 6-year prospective study in rural China."
Belinson et al., Am J. Clin Pathol 2011; 135:790-795. "A population-based clinical trial comparing endocervical high-risk HPV testing using hybrid capture 2 and Cervista from the SHENCCAST II study."
Dockter et al., 2009 Journal of Clinical Viroogy 45, 51: 539-547. "Analytical characterization of the APTIMA HPV assay."
Wong et al., 2011 Journal of Clinical Virology 51 (2011) 136-138. "Efficacy of Abbott real time high risk HPV test in evaluation of atypical squamous cells of undetermined significance from and Asian screening population."
Branca et al., 2005 Am J Clin Pathol 124: 113-121. "Survivin as a marker of cervical intraepithelial neoplasia and high-risk human papillomavirus and a predictor of virus clearance and prognosis in cervical cancer."
Branca et al., 2006 J Clin Pathol 59: 40-47. "Aberrant expression of VEFG-C is related to grade of cervical intraepithelial neoplasia (CIN) and high risk HPV but does not predict virus clearance after treatment of CIN or prognosis of cervical cancer."
Lambert et al., 2006 Experimental and Molecular Pathology 80: 192-196. "p16INK4A expression in cervical premalignant and malignant lesion."
Giannoudis et al., 2000 British J. Cancer 81:424-7. "Differential expression of p53 and p21 in low grade cervical squamous intraepithelial lesions infected with low, intermediate, and high risk human papillomaviruses."
Saqi et al., 2002 "Overexpression of p16INK4A in liquid-based specimens (SurePath) as marker of cervical dysplasia and neoplasia." 27: 365-370.
Non-final Office action for U.S. Appl. No. 11/559,366 dated Dec. 5, 2008.
Final Office action for U.S. Appl. No. 11/559,366 dated May 5, 2009.
Notice of Allowance for U.S. Appl. No. 11/559,366 dated Jan. 4, 2010.
Non-final Office action for U.S. Appl. No. 12/082,740 dated Jun. 12, 2009.
Final Office action for U.S. Appl. No. 12/082,740 dated Aug. 20, 2010.
Notice of Allowance for U.S. Appl. No. 12/082,740 dated Mar. 8, 2011.
Non-final Office action for U.S. Appl. No. 12/456,053 dated May 31, 2011.
Non-final Office action for U.S. Appl. No. 12/456,054 dated Aug. 17, 2011.
Non-final Office action for U.S. Appl. No. 12/456,055 dated Jul. 22, 2011.
EPO Communication for App. No. 09762928.1-1223/2300824, dated Aug. 15, 2011.
Extended European Search Report for App. No. 09762928.1-1223/2300824, dated Jul. 22, 2011.
EPO Communication for App. No. 06846299.3-2402/1951915, dated Apr. 7, 2010.
Extended European Search Report for App. No. 06846299.3-2402/1951915, dated Jan 8, 2010.
International Search Report for Int'l App. No. PCT/US2009/003537, dated Oct. 8, 2009.
International Search Report for Int'l App. No. PCT/US2009/003538, dated Oct. 15, 2009.
International Search Report for Int'l App. No. PCT/US2010/033944, dated Jul. 2, 2010.
International Preliminary Report on Patentability for Int'l App. No. PCT/US2009/003538, dated Dec. 14, 2010.
International Preliminary Report on Patentability for Int'l App. No. PCT/US2009/003537, dated Dec. 14, 2010.
Written Opinion of the International Searching Authorigy for Int'l App. No. PCT/US2009/003538, dated Oct. 15, 2009.

(56) References Cited

OTHER PUBLICATIONS

Written Opinion of the International Searching Authorigy for Int'l App. No. PCT/US2009/003537, dated Oct. 8, 2009.
Written Opinion of the International Searching Authorigy for Int'l App. No. PCT/US2010/033944, dated Jul. 2, 2010.
International Search Report for Int'l App. No. PCT/US2010/060765, dated Mar. 25, 2011.
Written Opinion of the International Searching Authorigy for Int'l App. No. PCT/US2010/0060765, dated Mar. 25, 2011.
International Search Report for Int'l App. No. PCT/US2006/60883, dated Jul. 18, 2007.
International Preliminary Report on Patentability for Int'l App. No. PCT/US2006/60883, dated Jul. 18, 2007.
Written Opinion of the International Searching Authority for Int'l App. No. PCT/US2006/60883, dated Jul. 18, 2007.
EPO Communication for App. No. 06846299.3-2401, dated Oct. 21, 2011.
Final Office action for U.S. Appl. No. 12/456,055 dated Jan. 6, 2012.
Final Office action for U.S. Appl. No. 12/456,053 dated Nov. 17, 2011.
Non-final Office action for U.S. Appl. No. 12/589,692 dated Feb. 7, 2012.
Non-final Office action for U.S. Appl. No. 12/589,641 dated Feb. 6, 2012.
Non-final Office action for U.S. Appl. No. 12/456,076 dated Feb. 9, 2012.
Advisory action for U.S. Appl. No. 12/456,053 dated Jan 26. 2012.
Advisory action for U.S. Appl. No. 12/082,740 dated Nov. 11, 2010.
Berumen et al., 2001 Asian-American Variants of Human Papillomavirus 16 and Risk for Cervical Cancer: a Case Control Study. Journal of the National Cancer Institute, vol. 93, No. 17.
Bleul et al., 1991 Human Papillomavirus Type 18 E6 and E7 Antibodies in Human Sera: Increased Anti-E7 Prevalence in Cervical Cancer Patients. Journal of Clinical Microbiology, Aug. 1991, pp. 1579-1588.
Bosch et al, 2002 Te Causal Relation between Human Papillomavirus and Cervical Cancer. J. Clinical Pathology, vol. 55, pp. 244-265.
De Villiers 1997. Papillomavirus and HPV typing. Clin. Dermatol 15:199-206.
Zur Hausen 2002. Papillomavirus and cancer: from basic studies to clinical pplication. Nat. rev. Cancer 2: 342-350.
Kreimer, et al. 2005. HPV 16 semiquantitative viral load and serological biomarkers in oral and oropharyngeal squamous cell carcinomas. Int J Cancer 115: 329-32.
Nair, Pillai 2005 Human papillomavirus and disease mechanisms: relevance to oral and cervical cancers Oral Diseases 11, 350-359.
Nindl, et al. 1994. Antibodies against linear and conformational epitopes of the human papillomavirus (HPV) type 16 E6 and E7 oncoproteins in sera of cervical cancer patients. Arch. Virol. 137:341-353.
Sasagawa, et al. 2003. Mucosal immunoglobulin-A and -G responses to oncogenic human papilloma virus capsids. Int J Cancer. Apr. 10, 2003; 104(3): 328-35.
Snijders, et al. 2006 HPV-mediated cervical carcinogenesis: concepts and clinical implications J Pathol 2006; 208: 152-164.
Stacey, et al. 1992. "Expression of human papillomavirus type 16 E6 protein by recombinant baculovirus and use for detection of anti-E6 antibodies in human sera", Journal of General Virology vol. 73, pp. 2337-2345.
Stoppler, et al. 1996 Natural Variants of the Human Papillomavirus Type 16 E6 Protein Differ in Their Abilities to Alter Keratinocyte Differentiation and to Induce p53 Degradation. Journal of Virology, p. 6987-6993 vol. 70, No. 10.
Tornesello, et al. 2004 Analysis of human papillomavirus type-16 variants in Italian women with cervical intraepithelial neoplasia and cervical cancer J Med Virol.; 74(1): 117-26.
Lehtinen, et al.2001. Human papillomavirus infection, risk for subsequent development of cervical neoplasia and associated population attributable fraction. J Clin Virolo 22:117-124.
Mougin, et al. 2001. Epidemiology of cervical papillomavirus infections. Recent knowledge. Press Med 30: 1017-23.
EPO Communication for App. No. 06846299.3, dated May 9, 2012.
Rocha-Zavaleta et al., 1997. British Journal of Cancer 75(8), 1144-1150. Differences in serological IgA responses to recombinant baculovirus-derived human papillomavirus E2 protein in the natural history of cervical neoplasia.

\* cited by examiner

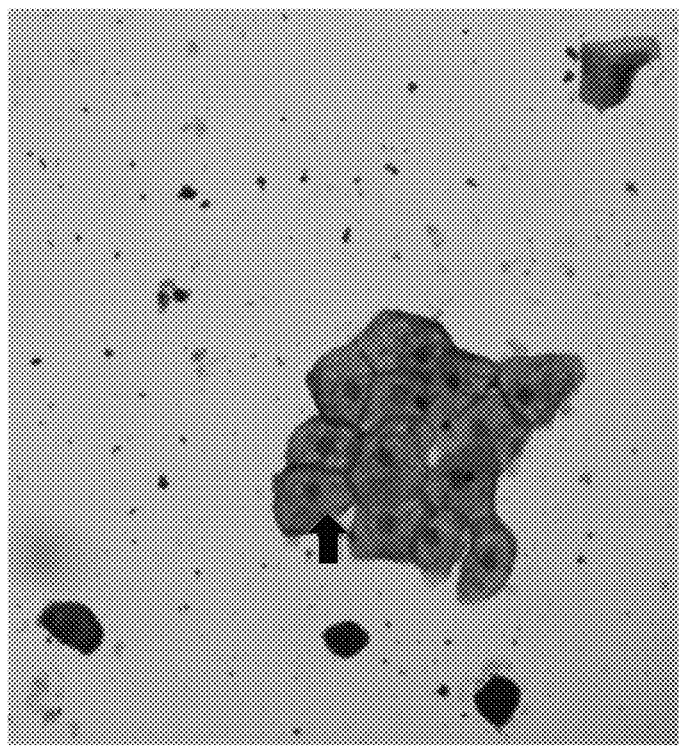
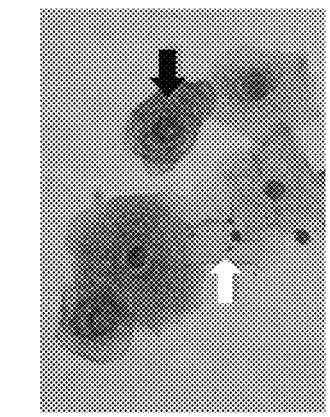
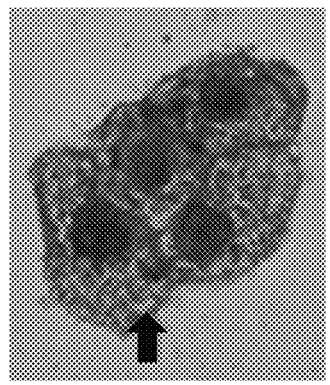
Figure 13A
Figure 13B
Figure 13C

SEQUENCE LISTING

<160> NUMBER OF SEQ ID NOS: 27

<210> SEQ ID NO 1
<211> LENGTH: 474
<212> TYPE: DNA
<213> ORGANISM: pappilomavirus

<400> SEQUENCE: 1

```
caccaaaaga gaactgcaat gtttcaggac ccacaggagc gacccagaaa gttaccacag      60
ttatgcacag agctgcaaac aactatacat gatataatat tagaatgtgt gtactgcaag     120
caacagttac tgcgacgtga ggtatatgac tttgcttttc gggatttatg catagtatat     180
agagatggga atccatatgc tgtatgtgat aaatgtttaa agtttattc taaaattagt      240 gagtatagac attattgtta tagtttgtat ggaacaacat tagaacagca atacaacaaa     300
ccgttgtgtg atttgttaat taggtgtatt aactgtcaaa agccactgtg tcctgaagaa     360
aagcaaagac atctggacaa aaagcaaaga ttccataata taagggggtcg gtggaccggt     420 cgatgtatgt cttgttgcag atcatcaaga acacgtagag aaacccagct gtaa           474
```

<210> SEQ ID NO 2
<211> LENGTH: 157
<212> TYPE: PRT
<213> ORGANISM: pappilomavirus

<400> SEQUENCE: 2

```
His Gln Lys Arg Thr Ala Met Phe Gln Asp Pro Gln Glu Arg Pro Arg
1               5                   10                  15

Lys Leu Pro Gln Leu Cys Thr Glu Leu Gln Thr Thr Ile His Asp Ile
            20                  25                  30

Ile Leu Glu Cys Val Tyr Cys Lys Gln Gln Leu Leu Arg Arg Glu Val
        35                  40                  45

Tyr Asp Phe Ala Phe Arg Asp Leu Cys Ile Val Tyr Arg Asp Gly Asn
    50                  55                  60

Pro Tyr Ala Val Cys Asp Lys Cys Leu Lys Phe Tyr Ser Lys Ile Ser
65                  70                  75                  80

Glu Tyr Arg His Tyr Cys Tyr Ser Leu Tyr Gly Thr Thr Leu Glu Gln
```

```
            85                  90                  95
Gln Tyr Asn Lys Pro Leu Cys Asp Leu Leu Ile Arg Cys Ile Asn Cys
            100                 105                 110

Gln Lys Pro Leu Cys Pro Glu Glu Lys Gln Arg His Leu Asp Lys Lys
            115                 120                 125

Gln Arg Phe His Asn Ile Arg Gly Arg Trp Thr Gly Arg Cys Met Ser
            130                 135                 140

Cys Cys Arg Ser Ser Arg Thr Arg Arg Glu Thr Gln Leu
145                 150                 155

<210> SEQ ID NO 3
<211> LENGTH: 34
<212> TYPE: DNA
<213> ORGANISM: pappilomavirus

<400> SEQUENCE: 3
cgcggatccc accaaaagag aactgcaatg tttc                                34

<210> SEQ ID NO 4
<211> LENGTH: 32
<212> TYPE: DNA
<213> ORGANISM: pappilomavirus

<400> SEQUENCE: 4
cccaagcttt tacagctggg tttctctacg tg                                  32

<210> SEQ ID NO 5
<211> LENGTH: 510
<212> TYPE: DNA
<213> ORGANISM: pappilomavirus

<400> SEQUENCE: 5
atgagaggat cgcatcacca tcaccatcac ggatcccacc aaaagagaac tgcaatgttt    60
caggacccac aggagcgacc cagaaagtta ccacagttat gcacagagct gcaacaact   120 atacatgata taatattaga atgtgtgtac tgcaagcaac agttactgcg acgtgaggta   180
tatgactttg cttttcggga tttatgcata gtatatagag atgggaatcc atatgctgta   240
tgtgataaat gtttaaagtt ttattctaaa attagtgagt atagacatta ttgttatagt   300
ttgtatggaa caacattaga acagcaatac aacaaaccgt tgtgtgattt gttaattagg   360
tgtattaact gtcaaaagcc actgtgtcct gaagaaaagc aaagacatct ggacaaaaag   420
caaagattcc ataatataag gggtcggtgg accggtcgat gtatgtcttg ttgcagatca   480
tcaagaacac gtagagaaac ccagctgtaa                                    510

<210> SEQ ID NO 6
<211> LENGTH: 169
<212> TYPE: PRT
<213> ORGANISM: pappilomavirus

<400> SEQUENCE: 6

Met Arg Gly Ser His His His His His His Gly Ser His Gln Lys Arg
1               5                   10                  15

Thr Ala Met Phe Gln Asp Pro Gln Glu Arg Pro Arg Lys Leu Pro Gln
            20                  25                  30

Leu Cys Thr Glu Leu Gln Thr Thr Ile His Asp Ile Ile Leu Glu Cys
        35                  40                  45

Val Tyr Cys Lys Gln Gln Leu Leu Arg Arg Glu Val Tyr Asp Phe Ala
    50                  55                  60
```

```
Phe Arg Asp Leu Cys Ile Val Tyr Arg Asp Gly Asn Pro Tyr Ala Val
 65                  70                  75                  80

Cys Asp Lys Cys Leu Lys Phe Tyr Ser Lys Ile Ser Glu Tyr Arg His
                 85                  90                  95

Tyr Cys Tyr Ser Leu Tyr Gly Thr Thr Leu Glu Gln Gln Tyr Asn Lys
            100                 105                 110

Pro Leu Cys Asp Leu Leu Ile Arg Cys Ile Asn Cys Gln Lys Pro Leu
        115                 120                 125

Cys Pro Glu Glu Lys Gln Arg His Leu Asp Lys Lys Gln Arg Phe His
130                 135                 140

Asn Ile Arg Gly Arg Trp Thr Gly Arg Cys Met Ser Cys Cys Arg Ser
145                 150                 155                 160

Ser Arg Thr Arg Arg Glu Thr Gln Leu
                165
```

<210> SEQ ID NO 7
<211> LENGTH: 300
<212> TYPE: DNA
<213> ORGANISM: Papillomavirus sylvilagi

<400> SEQUENCE: 7

```
gatcccatgg agatacacct acattgcatg aatatatgtt agatttgcaa ccagagacaa      60
ctgatctcta ctgttatgag caattaaatg acagctcaga ggaggaggat gaaatagatg     120
gtccagctgg acaagcagaa ccggacagag cccattacaa tattgtaacc ttttgttgca     180
agtgtgactc tacgcttcgg ttgtgcgtac aaagcacaca cgtagacatt cgtactttgg     240
aagacctgtt aatgggcaca ctaggaattg tgtgccccat ctgttctcag aaaccataag     300
```

<210> SEQ ID NO 8
<211> LENGTH: 97
<212> TYPE: PRT
<213> ORGANISM: pappilomavirus

<400> SEQUENCE: 8

```
His Gly Asp Thr Pro Thr Leu His Glu Tyr Met Leu Asp Leu Gln Pro
 1               5                  10                  15

Glu Thr Thr Asp Leu Tyr Cys Tyr Glu Gln Leu Asn Asp Ser Ser Glu
                20                  25                  30

Glu Glu Asp Glu Ile Asp Gly Pro Ala Gly Gln Ala Glu Pro Asp Arg
            35                  40                  45

Ala His Tyr Asn Ile Val Thr Phe Cys Cys Lys Cys Asp Ser Thr Leu
        50                  55                  60

Arg Leu Cys Val Gln Ser Thr His Val Asp Ile Arg Thr Leu Glu Asp
65                  70                  75                  80

Leu Leu Met Gly Thr Leu Gly Ile Val Cys Pro Ile Cys Ser Gln Lys
                85                  90                  95

Pro
```

<210> SEQ ID NO 9
<211> LENGTH: 31
<212> TYPE: DNA
<213> ORGANISM: pappilomavirus

<400> SEQUENCE: 9

```
cgcggatccc atggagatac acctacattg c                                     31
```

<210> SEQ ID NO 10
<211> LENGTH: 32
<212> TYPE: DNA
<213> ORGANISM: pappilomavirus

<400> SEQUENCE: 10
ccggaattct tatggtttct gagaacagat gg       32

<210> SEQ ID NO 11
<211> LENGTH: 972
<212> TYPE: DNA
<213> ORGANISM: pappilomavirus

<400> SEQUENCE: 11

```
atgtccccta ctaggttta ttggaaaatt aagggccttg tgcaacccac tcgacttctt       60
ttggaatatc ttgaagaaaa atatgaagag catttgtatg agcgcgatga aggtgataaa      120
tggcgaaaca aaaagtttga attgggtttg gagtttccca atcttcctta ttatattgat      180
ggtgatgtta aattaacaca gtctatggcc atcatacgtt atatagctga caagcacaac      240
atgttgggtg gttgtccaaa agagcgtgca gagatttcaa tgcttgaagg agcggttttg      300
gatattagat acggtgtttc gagaattgca tatagtaaag actttgaaac tctcaaagtt      360
gattttctta gcaagctacc tgaaatgctg aaaatgttcg aagatcgttt atgtcataaa      420
acatatttaa atggtgatca tgtaacccat cctgacttca tgttgtatga cgctcttgat      480
gttgttttat acatggaccc aatgtgcctg gatgcgttcc caaaattagt ttgtttttaaa      540
aaacgtattg aagctatccc acaaattgat aagtacttga atccagcaa gtatatagca      600
tggcctttgc agggctggca agccacgttt ggtggtggcg accatcctcc aaaatcggat      660
ctggttccgc gtggatccca tggagataca cctacattgc atgaatatat gttagatttg      720
caaccagaga caactgatct ctactgttat gagcaattaa atgacagctc agaggaggag      780
gatgaaatag atggtccagc tggacaagca gaaccggaca gagcccatta caatattgta      840
acctttttgtt gcaagtgtga ctctacgctt cggttgtgcg tacaaagcac acacgtagac      900
attcgtactt tggaagacct gttaatgggc acactaggaa ttgtgtgccc catctgttct      960
cagaaaccat aa                                                          972
```

<210> SEQ ID NO 12
<211> LENGTH: 323
<212> TYPE: PRT
<213> ORGANISM: pappilomavirus

<400> SEQUENCE: 12

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110
```

```
Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser His Gly Asp Thr Pro Thr Leu His Glu Tyr Met Leu Asp Leu
225                 230                 235                 240

Gln Pro Glu Thr Thr Asp Leu Tyr Cys Tyr Glu Gln Leu Asn Asp Ser
                245                 250                 255

Ser Glu Glu Glu Asp Glu Ile Asp Gly Pro Ala Gly Gln Ala Glu Pro
            260                 265                 270

Asp Arg Ala His Tyr Asn Ile Val Thr Phe Cys Cys Lys Cys Asp Ser
        275                 280                 285

Thr Leu Arg Leu Cys Val Gln Ser Thr His Val Asp Ile Arg Thr Leu
    290                 295                 300

Glu Asp Leu Leu Met Gly Thr Leu Gly Ile Val Cys Pro Ile Cys Ser
305                 310                 315                 320

Gln Lys Pro

<210> SEQ ID NO 13
<211> LENGTH: 1602
<212> TYPE: DNA
<213> ORGANISM: pappilomavirus

<400> SEQUENCE: 13
tcgagatgca ggtgactttt atttacatcc tagttattac atgttacgaa acgacgtaa      60 acgtttacca tattttttt cagatgtctc tttggctgcc tagtgaggcc actgtctact     120
tgcctcctgt cccagtatct aaggttgtaa gcacggatga atatgttgca cgcacaaaca    180
tatattatca tgcaggaaca tccagactac ttgcagttgg acatccctat tttcctatta    240
aaaaacctaa caataacaaa atattagttc ctaaagtatc aggattacaa tacagggtat    300
ttagaataca tttacctgac cccaataagt ttggttttcc tgacacctca tttataatc     360 cagatacaca gcggctggtt tgggcctgtg taggtgttga ggtaggtcgt ggtcagccat    420
taggtgtggg cattagtggc catcctttat taaataaatt ggatgacaca gaaaatgcta    480
gtgcttatgc agcaaatgca ggtgtggata atagagaatg tatatctatg gattacaaac    540
aaacacaatt gtgtttaatt ggttgcaaac cacctatagg ggaacactgg gcaaaggat     600 ccccatgtac caatgttgca gtaaatccag gtgattgtcc accattagag ttaataaaca    660
cagttattca ggatggtgat atggttcata ctggctttgg tgctatggac tttactacat    720
tacaggctaa caaagtgaa gttccactgg atatttgtac atctatttgc aaatatccag     780
attatattaa aatggtgtca gaaccatatg gcgacagctt attttttat ttacgaaggg     840 aacaaatgtt tgttagacat ttatttaata gggctggtac tgttggtgaa aatgtaccag    900
```

-continued

```
acgatttata cattaaaggc tctgggtcta ctgcaaattt agccagttca aattattttc      960
ctacacctag tggttctatg gttacctctg atgcccaaat attcaataaa ccttattggt     1020
tacaacgagc acagggccac aataatggca tttgttgggg taaccaacta tttgttactg     1080
ttgttgatac tacacgcagt acaaatatgt cattatgtgc tgccatatct acttcagaaa     1140
ctacatataa aaatactaac tttaaggagt acctacgaca tggggaggaa tatgatttac     1200
agtttatttt tcaactgtgc aaaataacct taactgcaga cgttatgaca tacatacatt     1260
ctatgaattc cactattttg gaggactgga attttggtct acaacctccc ccaggaggca     1320
cactagaaga tacttatagg tttgtaaccc aggcaattgc ttgtcaaaaa catacacctc     1380
cagcacctaa agaagatgat ccccttaaaa aatacacttt ttgggaagta aatttaaagg     1440
aaaagttttc tgcagaccta gatcagtttc ctttaggacg caaatttta ctacaagcag     1500 gattgaaggc caaaccaaaa tttacattag gaaaacgaaa agctacaccc accacctcat     1560
ctacctctac aactgctaaa cgcaaaaaac gtaagctgta aa                        1602
```

<210> SEQ ID NO 14
<211> LENGTH: 531
<212> TYPE: PRT
<213> ORGANISM: pappilomavirus

<400> SEQUENCE: 14

```
Met Gln Val Thr Phe Ile Tyr Ile Leu Val Ile Thr Cys Tyr Glu Asn
1               5                   10                  15

Asp Val Asn Val Tyr His Ile Phe Phe Gln Met Ser Leu Trp Leu Pro
            20                  25                  30

Ser Glu Ala Thr Val Tyr Leu Pro Pro Val Pro Val Ser Lys Val Val
        35                  40                  45

Ser Thr Asp Glu Tyr Val Ala Arg Thr Asn Ile Tyr Tyr His Ala Gly
    50                  55                  60

Thr Ser Arg Leu Leu Ala Val Gly His Pro Tyr Phe Pro Ile Lys Lys
65                  70                  75                  80

Pro Asn Asn Asn Lys Ile Leu Val Pro Lys Val Ser Gly Leu Gln Tyr
                85                  90                  95

Arg Val Phe Arg Ile His Leu Pro Asp Pro Asn Lys Phe Gly Phe Pro
            100                 105                 110

Asp Thr Ser Phe Tyr Asn Pro Asp Thr Gln Arg Leu Val Trp Ala Cys
        115                 120                 125

Val Gly Val Glu Val Gly Arg Gly Gln Pro Leu Gly Val Gly Ile Ser
    130                 135                 140

Gly His Pro Leu Leu Asn Lys Leu Asp Asp Thr Glu Asn Ala Ser Ala
145                 150                 155                 160

Tyr Ala Ala Asn Ala Gly Val Asp Asn Arg Glu Cys Ile Ser Met Asp
                165                 170                 175

Tyr Lys Gln Thr Gln Leu Cys Leu Ile Gly Cys Lys Pro Pro Ile Gly
            180                 185                 190

Glu His Trp Gly Lys Gly Ser Pro Cys Thr Asn Val Ala Val Asn Pro
        195                 200                 205

Gly Asp Cys Pro Pro Leu Glu Leu Ile Asn Thr Val Ile Gln Asp Gly
    210                 215                 220

Asp Met Val His Thr Gly Phe Gly Ala Met Asp Phe Thr Thr Leu Gln
225                 230                 235                 240

Ala Asn Lys Ser Glu Val Pro Leu Asp Ile Cys Thr Ser Ile Cys Lys
```

```
                        245                 250                 255
Tyr Pro Asp Tyr Ile Lys Met Val Ser Glu Pro Tyr Gly Asp Ser Leu
            260                 265                 270

Phe Phe Tyr Leu Arg Arg Glu Gln Met Phe Val Arg His Leu Phe Asn
        275                 280                 285

Arg Ala Gly Thr Val Gly Glu Asn Val Pro Asp Asp Leu Tyr Ile Lys
    290                 295                 300

Gly Ser Gly Ser Thr Ala Asn Leu Ala Ser Ser Asn Tyr Phe Pro Thr
305                 310                 315                 320

Pro Ser Gly Ser Met Val Thr Ser Asp Ala Gln Ile Phe Asn Lys Pro
                325                 330                 335

Tyr Trp Leu Gln Arg Ala Gln Gly His Asn Asn Gly Ile Cys Trp Gly
            340                 345                 350

Asn Gln Leu Phe Val Thr Val Val Asp Thr Thr Arg Ser Thr Asn Met
        355                 360                 365

Ser Leu Cys Ala Ala Ile Ser Thr Ser Glu Thr Thr Tyr Lys Asn Thr
    370                 375                 380

Asn Phe Lys Glu Tyr Leu Arg His Gly Glu Glu Tyr Asp Leu Gln Phe
385                 390                 395                 400

Ile Phe Gln Leu Cys Lys Ile Thr Leu Thr Ala Asp Val Met Thr Tyr
                405                 410                 415

Ile His Ser Met Asn Ser Thr Ile Leu Glu Asp Trp Asn Phe Gly Leu
            420                 425                 430

Gln Pro Pro Pro Gly Gly Thr Leu Glu Asp Thr Tyr Arg Phe Val Thr
        435                 440                 445

Gln Ala Ile Ala Cys Gln Lys His Thr Pro Ala Pro Lys Glu Asp
    450                 455                 460

Asp Pro Leu Lys Lys Tyr Thr Phe Trp Glu Val Asn Leu Lys Glu Lys
465                 470                 475                 480

Phe Ser Ala Asp Leu Asp Gln Phe Pro Leu Gly Arg Lys Phe Leu Leu
                485                 490                 495

Gln Ala Gly Leu Lys Ala Lys Pro Lys Phe Thr Leu Gly Lys Arg Lys
            500                 505                 510

Ala Thr Pro Thr Thr Ser Ser Thr Ser Thr Thr Ala Lys Arg Lys Lys
        515                 520                 525

Arg Lys Leu
    530

<210> SEQ ID NO 15
<211> LENGTH: 34
<212> TYPE: DNA
<213> ORGANISM: pappilomavirus

<400> SEQUENCE: 15
ccgctcgaga tgcaggtgac ttttatttac atcc                              34

<210> SEQ ID NO 16
<211> LENGTH: 34
<212> TYPE: DNA
<213> ORGANISM: pappilomavirus

<400> SEQUENCE: 16
cccaagcttt tacagcttac gttttttgcg ttta                              34

<210> SEQ ID NO 17
<211> LENGTH: 1716
```

```
<212> TYPE: DNA
<213> ORGANISM: pappilomavirus

<400> SEQUENCE: 17
atgccgcggg gttctcatca tcatcatcat catggtatgg ctagcatgac tggtggacag      60
caaatgggtc gggatctgta cgacgatgac gataaggatc gatggggatc cgagctcgag     120
atgcaggtga cttttattta catcctagtt attacatgtt acgaaaacga cgtaaacgtt     180
taccatattt ttttcagat gtctctttgg ctgcctagtg aggccactgt ctacttgcct      240
cctgtcccag tatctaaggt tgtaagcacg gatgaatatg ttgcacgcac aaacatatat     300
tatcatgcag gaacatccag actacttgca gttggacatc cctatttttcc tattaaaaaa    360
cctaacaata caaaatatt agttcctaaa gtatcaggat tacaatacag ggtatttaga      420
atacatttac ctgaccccaa taagtttggt tttcctgaca cctcatttta taatccagat     480
acacagcggc tggtttgggc ctgtgtaggt gttgaggtag gtcgtggtca gccattaggt     540
gtgggcatta gtggccatcc tttattaaat aaattggatg acacagaaaa tgctagtgct     600
tatgcagcaa atgcaggtgt ggataataga gaatgtatat ctatggatta caaacaaaca     660
caattgtgtt taattggttg caaaccacct ataggggaac actggggcaa aggatcccca     720
tgtaccaatg ttgcagtaaa tccaggtgat tgtccaccat tagagttaat aaacacagtt     780
attcaggatg tgatatggt tcatactggc tttggtgcta tggactttac tacattacag      840
gctaacaaaa gtgaagttcc actggatatt tgtacatcta tttgcaaata tccagattat     900
attaaaatgg tgtcagaacc atatggcgac agcttatttt tttatttacg aagggaacaa     960
atgtttgtta gacattttat taatagggct ggtactgttg gtgaaaatgt accagacgat    1020
ttatacatta aaggctctgg gtctactgca aatttagcca gttcaaatta ttttcctaca    1080
cctagtggtt ctatggttac ctctgatgcc caaatattca ataaaccttta ttggttacaa   1140
cgagcacagg ccacaataa tggcatttgt tggggtaacc aactatttgt tactgttgtt    1200
gatactacac gcagtacaaa tatgtcatta tgtgctgcca tatctacttc agaaactaca    1260
tataaaaata ctaactttaa ggagtaccta cgacatgggg aggaatatga tttacagttt    1320
atttttcaac tgtgcaaaat aaccttaact gcagacgtta tgcatacat acattctatg     1380
aattccacta ttttggagga ctggaatttt ggtctacaac ctccccccagg aggcacacta   1440
gaagatactt ataggtttgt aacccaggca attgcttgtc aaaaacatac acctccagca    1500
cctaaagaag atgatcccct taaaaaatac acttttttggg aagtaaattt aaaggaaaag   1560
ttttctgcag acctagatca gtttccttta ggacgcaaat ttttactaca agcaggattg    1620
aaggccaaac caaaatttac attaggaaaa cgaaaagcta cacccaccac ctcatctacc    1680
tctacaactg ctaaacgcaa aaaacgtaag ctgtaa                               1716

<210> SEQ ID NO 18
<211> LENGTH: 571
<212> TYPE: PRT
<213> ORGANISM: pappilomavirus

<400> SEQUENCE: 18

Met Pro Arg Gly Ser His His His His His Gly Met Ala Ser Met
1               5                   10                  15

Thr Gly Gly Gln Gln Met Gly Arg Asp Leu Tyr Asp Asp Asp Lys
                20                  25                  30

Asp Arg Trp Gly Ser Glu Leu Glu Met Gln Val Thr Phe Ile Tyr Ile
            35                  40                  45
```

```
Leu Val Ile Thr Cys Tyr Glu Asn Asp Val Asn Val Tyr His Ile Phe
    50              55                  60
Phe Gln Met Ser Leu Trp Leu Pro Ser Glu Ala Thr Val Tyr Leu Pro
65              70                  75                  80
Pro Val Pro Val Ser Lys Val Val Ser Thr Asp Glu Tyr Val Ala Arg
                85                  90                  95
Thr Asn Ile Tyr Tyr His Ala Gly Thr Ser Arg Leu Leu Ala Val Gly
            100                 105                 110
His Pro Tyr Phe Pro Ile Lys Lys Pro Asn Asn Lys Ile Leu Val
        115                 120                 125
Pro Lys Val Ser Gly Leu Gln Tyr Arg Val Phe Arg Ile His Leu Pro
    130                 135                 140
Asp Pro Asn Lys Phe Gly Phe Pro Asp Thr Ser Phe Tyr Asn Pro Asp
145                 150                 155                 160
Thr Gln Arg Leu Val Trp Ala Cys Val Gly Val Glu Val Gly Arg Gly
                165                 170                 175
Gln Pro Leu Gly Val Gly Ile Ser Gly His Pro Leu Leu Asn Lys Leu
            180                 185                 190
Asp Asp Thr Glu Asn Ala Ser Ala Tyr Ala Ala Asn Ala Gly Val Asp
        195                 200                 205
Asn Arg Glu Cys Ile Ser Met Asp Tyr Lys Gln Thr Gln Leu Cys Leu
    210                 215                 220
Ile Gly Cys Lys Pro Pro Ile Gly Glu His Trp Gly Lys Gly Ser Pro
225                 230                 235                 240
Cys Thr Asn Val Ala Val Asn Pro Gly Asp Cys Pro Pro Leu Glu Leu
                245                 250                 255
Ile Asn Thr Val Ile Gln Asp Gly Asp Met Val His Thr Gly Phe Gly
            260                 265                 270
Ala Met Asp Phe Thr Thr Leu Gln Ala Asn Lys Ser Glu Val Pro Leu
        275                 280                 285
Asp Ile Cys Thr Ser Ile Cys Lys Tyr Pro Asp Tyr Ile Lys Met Val
    290                 295                 300
Ser Glu Pro Tyr Gly Asp Ser Leu Phe Phe Tyr Leu Arg Arg Glu Gln
305                 310                 315                 320
Met Phe Val Arg His Leu Phe Asn Arg Ala Gly Thr Val Gly Glu Asn
                325                 330                 335
Val Pro Asp Asp Leu Tyr Ile Lys Gly Ser Gly Ser Thr Ala Asn Leu
            340                 345                 350
Ala Ser Ser Asn Tyr Phe Pro Thr Pro Ser Gly Ser Met Val Thr Ser
        355                 360                 365
Asp Ala Gln Ile Phe Asn Lys Pro Tyr Trp Leu Gln Arg Ala Gln Gly
    370                 375                 380
His Asn Asn Gly Ile Cys Trp Gly Asn Gln Leu Phe Val Thr Val Val
385                 390                 395                 400
Asp Thr Thr Arg Ser Thr Asn Met Ser Leu Cys Ala Ala Ile Ser Thr
                405                 410                 415
Ser Glu Thr Thr Tyr Lys Asn Thr Asn Phe Lys Glu Tyr Leu Arg His
            420                 425                 430
Gly Glu Glu Tyr Asp Leu Gln Phe Ile Phe Gln Leu Cys Lys Ile Thr
        435                 440                 445
Leu Thr Ala Asp Val Met Thr Tyr Ile His Ser Met Asn Ser Thr Ile
    450                 455                 460
```

```
Leu Glu Asp Trp Asn Phe Gly Leu Gln Pro Pro Gly Gly Thr Leu
465                 470                 475                 480

Glu Asp Thr Tyr Arg Phe Val Thr Gln Ala Ile Ala Cys Gln Lys His
            485                 490                 495

Thr Pro Pro Ala Pro Lys Glu Asp Asp Pro Leu Lys Lys Tyr Thr Phe
            500                 505                 510

Trp Glu Val Asn Leu Lys Glu Lys Phe Ser Ala Asp Leu Asp Gln Phe
            515                 520                 525

Pro Leu Gly Arg Lys Phe Leu Leu Gln Ala Gly Leu Lys Ala Lys Pro
            530                 535                 540

Lys Phe Thr Leu Gly Lys Arg Lys Ala Thr Pro Thr Thr Ser Ser Thr
545                 550                 555                 560

Ser Thr Thr Ala Lys Arg Lys Lys Arg Lys Leu
                565                 570

<210> SEQ ID NO 19
<211> LENGTH: 322
<212> TYPE: PRT
<213> ORGANISM: pappilomavirus

<400> SEQUENCE: 19

Met Ala Ser Met Thr Gly Gly Gln Gln Met Gly Arg Gly Ser Gln Val
1               5                   10                  15

Thr Phe Ile Tyr Ile Leu Val Ile Thr Cys Tyr Glu Asn Asp Val Asn
            20                  25                  30

Val Tyr His Ile Phe Phe Gln Met Ser Leu Trp Leu Pro Ser Glu Ala
            35                  40                  45

Thr Val Tyr Leu Pro Pro Val Pro Val Ser Lys Val Val Ser Thr Asp
        50                  55                  60

Glu Tyr Val Ala Arg Thr Asn Ile Tyr Tyr His Ala Gly Thr Ser Arg
65                  70                  75                  80

Leu Leu Ala Val Gly His Pro Tyr Phe Pro Ile Lys Lys Pro Asn Asn
                85                  90                  95

Asn Lys Ile Leu Val Pro Lys Val Ser Gly Leu Gln Tyr Arg Val Phe
            100                 105                 110

Arg Ile His Leu Pro Asp Pro Asn Lys Phe Gly Phe Pro Asp Thr Ser
            115                 120                 125

Phe Tyr Asn Pro Asp Thr Gln Arg Leu Val Trp Ala Cys Val Gly Val
        130                 135                 140

Glu Val Gly Arg Gly Gln Pro Leu Gly Val Gly Ile Ser Gly His Pro
145                 150                 155                 160

Leu Leu Asn Lys Leu Asp Asp Thr Glu Asn Ala Ser Ala Tyr Ala Ala
                165                 170                 175

Asn Ala Gly Val Asp Asn Arg Glu Cys Ile Ser Met Asp Tyr Lys Gln
            180                 185                 190

Thr Gln Leu Cys Leu Ile Gly Cys Lys Pro Pro Ile Gly Glu His Trp
            195                 200                 205

Gly Lys Gly Ser Pro Cys Thr Asn Val Ala Val Asn Pro Gly Asp Cys
        210                 215                 220

Pro Pro Leu Glu Leu Ile Asn Thr Val Ile Gln Asp Gly Asp Met Val
225                 230                 235                 240

His Thr Gly Phe Gly Ala Met Asp Phe Thr Thr Leu Gln Ala Asn Lys
                245                 250                 255

Ser Glu Val Pro Leu Asp Ile Cys Thr Ser Ile Cys Lys Tyr Pro Asp
            260                 265                 270
```

```
Tyr Ile Lys Met Val Ser Glu Pro Tyr Gly Asp Ser Leu Phe Phe Tyr
        275                 280                 285

Leu Arg Arg Glu Gln Met Phe Val Arg His Leu Phe Asn Arg Ala Gly
    290                 295                 300

Thr Val Gly Glu Asn Val Pro Asp Asp Leu Val Glu His His His His
305                 310                 315                 320

His His

<210> SEQ ID NO 20
<211> LENGTH: 20
<212> TYPE: DNA
<213> ORGANISM: pappilomavirus
<220> FEATURE:
<221> NAME/KEY: misc_feature
<222> LOCATION: (3)..(3)
<223> OTHER INFORMATION: n is a, c, g, or t

<400> SEQUENCE: 20 gncargghc ayaayaatgg                                            20

<210> SEQ ID NO 21
<211> LENGTH: 23
<212> TYPE: DNA
<213> ORGANISM: pappilomavirus

<400> SEQUENCE: 21
gtdgtatcha cmhcagtaac aaa                                       23

<210> SEQ ID NO 22
<211> LENGTH: 64
<212> TYPE: DNA
<213> ORGANISM: pappilomavirus

<400> SEQUENCE: 22
cvcaggghca yaayaatggc atttgttggg gtaaccaact atttgttact gttgtdgaya    60 cyac                                                                64

<210> SEQ ID NO 23
<211> LENGTH: 20
<212> TYPE: DNA
<213> ORGANISM: pappilomavirus

<400> SEQUENCE: 23
gttactgcga cgtgaggtat                                           20

<210> SEQ ID NO 24
<211> LENGTH: 20
<212> TYPE: DNA
<213> ORGANISM: pappilomavirus

<400> SEQUENCE: 24
gtttcaggac ccacaggagc                                           20

<210> SEQ ID NO 25
<211> LENGTH: 20
<212> TYPE: DNA
<213> ORGANISM: pappilomavirus

<400> SEQUENCE: 25
caacggtttg ttgtattgct                                           20
```

```
<210> SEQ ID NO 26
<211> LENGTH: 181
<212> TYPE: DNA
<213> ORGANISM: pappilomavirus

<400> SEQUENCE: 26
gttactgcga cgtgaggtat atgactttgc ttttcgggat ttatgcatag tatatagaga      60
tgggaatcca tatgctgtat gtgataaatg tttaaagttt tattctaaaa ttagtgagta     120
tagacattat tgttatagtt tgtatggaac aacattagaa cagcaataca acaaaccgtt     180
g                                                                    181

<210> SEQ ID NO 27
<211> LENGTH: 286
<212> TYPE: DNA
<213> ORGANISM: pappilomavirus

<400> SEQUENCE: 27
gtttcaggac ccacaggagc gacccagaaa gttaccacag ttatgcacag agctgcaaac      60
aactatacat gatataatat tagaatgtgt gtactgcaag caacagttac tgcgacgtga     120
ggtatatgac tttgctttc gggatttatg catagtatat agagatggga atccatatgc     180
tgtatgtgat aaatgtttaa agttttattc taaaattagt gagtatagac attattgtta     240
tagtttgtat ggaacaacat tagaacagca atacaacaaa ccgttg                   286
```

IN SITU DETECTION OF EARLY STAGES AND LATE STAGES HPV INFECTION

CROSS-REFERENCE TO RELATED APPLICATIONS

This instant application is a continuation of issued U.S. Pat. No. 8,859,218 that claims the benefit of U.S. provisional patent application Ser. No. 61/131,991, filed Jun. 13, 2008, and U.S. provisional patent application Ser. No. 61/192,912, filed Sep. 22, 2008. Each of the aforementioned related patent applications is herein incorporated by reference.

BACKGROUND OF THE INVENTION

Infection by human papillomaviruses (HPV) at specific epithelium cells to induce epithelial proliferations plays an important role for cervical carcinogenesis. About 99 percent of confirmed cervical cancer cases are found to be associated with HPV infection with biopsy-confirmed squamous intra-epithelial lesions (SIL) or cervical intraepithelial neoplasia (CIN). The incidence of HPV infection, primarily transmitted through sexual contact, is highest among young women and about 20 millions of sexually active men and women worldwide are currently infected. Approximately 1% of the population has genital warts and 4% of women have cervical precancerous lesions, such as low grade of squamous intra-epithelial lesion (LSIL), high grade of squamous intraepithelial lesion (HSIL) or atypical squamous cells of undetermined significance (ASCUS).

These lesions are preferentially observed in women aged 35-40 yrs and have a high risk of progressing towards invasive cervical cancer. It is generally thought that persistent infection of human papillomavirus (HPV) is essential for developing precancerous epithelial lesions. Infections of high-risk types of HPV in women with LSIL may or may not progress to HSIL. In fact, remission occurs in the majority of LSIL human subjects while some progress to HSIL. Although 99.7% of cervical cancers are HPV positive, the integration of viral genome into the host genome is required to facilitate the necessary genetic expression for developing into HSIL or cancer. In fact, only one in every 10 women with persistent HPV infection may develop higher grades of CIN lesions, such as cervical intraepithelial neoplasia (CIN) grade 2 and grade 3 (CIN2, and CIN3, respectively), and a portion of these epithelival lesion cases may ultimately progress into cervical cancer.

In the past, screening for cervical cancer has been based on conventional cytology screening tests, e.g., obtaining papanicolaou (Pap) smears for cytological staining tests, and suspicious smears are followed up with colposcopy, and/or histological biopsy. The use of these cytological screening tests contributes to a reduction in the mortality of cervical cancer. However, due to subjective test criteria, there are various drawbacks for pap smear tests: difficulty in obtaining samples, poor inter- and intra-observer agreement, high rates of false negatives and false positives, requiring specialized labs staffed with highly trained personnel, and inability to identify the majority of HPV-infected human subjects. More reproducible assays are needed to improve the current screening tests and to avoid unnecessary medical intervention and psychological distress in affected women. The current conventional cervical cytology screening tests have sensitivity varied from about 30% to about 87%.

Detecting HPV infection by nucleic acid tests, such as "DNA Hybrid Capture", has been developed with high assay sensitivity, but is still not ideal, due to not only its high cost, assay operation procedures, the requirements for facility, equipment, and highly trained personnel, but also its very low positive predictive value (PPV) in cervical intraepithelial neoplasia (CIN) testing samples. Assays like PreTect HPV-Proofer® provide the detection of E6/E7 mRNA with sensitivity equivalent to HPV Hybrid Capture tests with higher positive predictive value but cannot directly detect E6/E7 oncoprtoeins in situ. In addition, DNA testing could not differentiate disease stages after HPV infection nor the diagnosis of different cell lesions (e.g., cannot diffrentiate LSIL from HSIL, nor CIN lesions from non-transforming latent or remissive viral infection). What is needed is a low cost, simple, sensitive and specific assay that can be routinely performed in a clinical lab or doctor's office and is capable of detecting early stages of epithelial lesions, distinguishing LSIL from HSIL, and/or predicting the risk of progression into cervical cancer.

Known protocols for producing monoclonal antibodies are generally unsuitable for the production of anti-HPV monoclonal antibodies and cannot be used in immunocytochemical diagnostic tests performed on human subjects of the general population. This is because antibodies produced by these protocols will not necessarily react with the naturally occurring HPV viral proteins in infected human cells. It is thought that the epitopes recognized by antibodies if generated by conventional protocols will not necessarily be those epitopes which are resistant to the harsh procedures involved in standard sampling, fixing and storing of clinical specimens. In addition, three problems exist in clinical HPV detection. One is that HPV proteins in clinical samples are present in very small quantities. Secondly, there are too many HPV types and most HPV types present in clinical samples are not known or systemically identified due to the lack of available antibodies. Third, HPV virus can not be cultured in labs by standard tissue culture techniques. Thus, there are no available HPV proteins purified in large quantities as immunogens for generating anti-HPV antibodies, and there are no available HPV proteins or purified anti-HPV antibodies to recognize anti-viral antibodies or viral proteins present in clinical samples for clinical HPV detection.

Only about 15 HPV types out of more than 100 HPV types are at high risk of developing into cervical intraepithelial neoplasia (CIN) or cervical cancer. Among them, around 70% of reported cervical cancer cases and 50% of reported CIN 2 and CIN 3 cases are caused by two high risk HPV types, i.e., HPV type-16 and HPV type-18. However, some progressive cervical cancer cases are reported to be associated with low risk HPV types, and infection of some high risk HPV types will never progress into cervical cancer. Infections by these two prevailing high risk HPV types do not correlate with tumor development or cancer progression. For this reason, it seems important to identify those HPV-infected human subjects that express particular oncogenic proteins rather than just identify HPV infection by high risk types.

Thus, there is a need for detecting the expression of HPV-related oncoproteins in clinical samples as these oncoproteins may serve as cervical cancer biomarkers to better predict the risk of developing high grade of cell lesions or cervical cancer-related diseases. There is also a need to develop anti-HPV antibodies and appropriate HPV immunoassays to detect the presence of invasive cervical cancer and/or HPV-related oncoproteins as cervical cancer biomarkers and predict the risk for malignant transformation of epithelial lesions into cervical cancer.

SUMMARY OF THE INVENTION

Embodiments of the invention provide various immunoassays for in situ detection of HPV proteins using various monoclonal antibodies against recombinant HPV proteins such that infection by high risk and/or low risk HPV types can be detected by a single specific monoclonal antibody and/or a general pan antibody. The invention also provides HPV immunocytochemistry (ICC) assay, HPV flow cytometry assay, HPV immunohistochemistry (IHC) assay to detect the presence of HPV proteins in cervical cells or cervical tissues. In addition, monoclonal antibodies highly specific for HPV viral proteins are also provided to be used in the HPV ICC or HPV flow cytometry assays.

In one embodiment, a method of detecting papillomavirus infection in a human subject is conducted by an immunocytological assay to detect in situ one or more papillomavirus proteins from one or more papillomavirus types present in a biological sample on a slide containing a thin layer of human cells, using one or more antibodies to stain the thin layer of human cells. The method includes providing a clinical sample from the human subject, processing the sample into a mixture of morphologically abnormal and normal human cells, applying the mixture in a thin layer of cells on a slide, and conducting an immunocytochemistry assay using one or more antibodies generated against one or more purified recombinant papillomavirus proteins, such that one or more papillomavirus viral proteins from one or more papillomavirus types present in the clinical sample on the slide containing the mixture of morphologically abnormal and normal human cells is stained in situ.

In another embodiment, a method of detecting papillomavirus infection in a human subject includes providing a clinical sample from the human subject and tagging one or more antibodies with an agent, wherein the clinical sample is processed into a liquid-based solution containing a mixture of morphologically abnormal and normal human cells. The mixture of the morphologically abnormal and normal human cells is stained using the one or more antibodies generated against one or more purified recombinant papillomavirus proteins. The method further includes conducting one or more flow cytometry assays to detect individual cells by separating each cell from the mixture of the morphologically abnormal and normal human cells, and detecting the presence of one or more human papillomavirus viral proteins from one or more papillomavirus types in the mixture of the morphologically abnormal and normal human cells contained in the liquid-based solution from the clinical sample.

In one embodiment, the one or more antibodies are generated against one or more purified recombinant papillomavirus proteins, wherein at least one antibody is capable of recognizing a papillomavirus early protein. In another embodiment, the one or more antibodies are tagged with an agent, and one or more human cells from a biological sample of the human subject are prepared into a liquid-based solution, such that the binding of the one or more antibodies with the one or more papillomavirus proteins from one or more papillomavirus types present in the one or more human cells of the biological sample can be detected by the presence of the agent reacting with the one or more tagged antibodies. In another embodiment, the agents include a colormetric agent, a fluorescent chromogen, and another agent for the later separation and identification of the one or more human cells in one or more flow cytometry assays.

In addition, a kit for performing an immunocytological assay is provided. The kit may include an pre-antibody blocking solution, post-antibody blocking solution, an anti-HPV antibody as the primary antibody, an anti-mouse or anti-rabbit immunoglobulin conjugated with HRP or biotin, or other agents as secondary antibody, and a solution containing appropriate agents used as substrate for the secondary antibody to be detected.

In still another embodiment, a kit is provided for detecting papillomavirus infection in a human subject and includes an anti-HPV monoclonal antibody capable of binding to a papillomavirus early protein for conducting an immunocytochemistry assay on a clinical sample from the human subject processed into a solution containing a mixture of morphologically abnormal and normal human cells and applied in a thin layer of cells on a slide for staining in situ one or more papillomavirus viral proteins from one or more papillomavirus types present in the clinical sample on the slide containing the mixture of morphologically abnormal and normal human cells.

Figure 5A:

FIG. 5A shows the staining results of a clinical sample diagnosed as squamous cell carcinoma (SCC) stained with an anti-HPV E6 mouse monoclonal antibody in an ICC assay according to another embodiment of the invention.

Figure 5B:

FIG. 5B shows the staining results of the same SCC sample as used in FIG. 5A with an anti-HPV E7 mouse monoclonal antibody in an ICC assay according to another embodiment of the invention.

Figure 5C:

FIG. 5C shows the staining results of the same SCC sample as shown in FIG. 5A using an anti-p16 mouse monoclonal antibody in an ICC assay according to another embodiment of the invention.

Figure 6B:
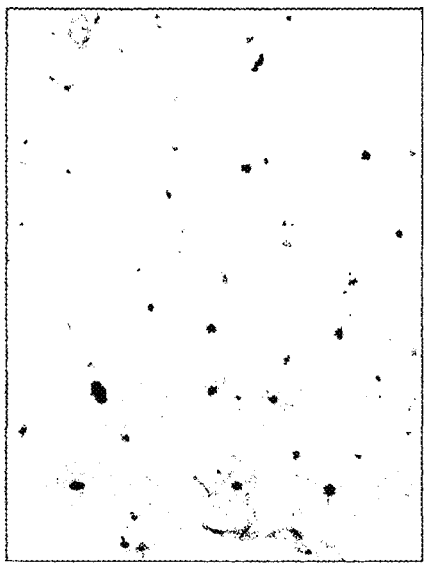
Figure 6A:
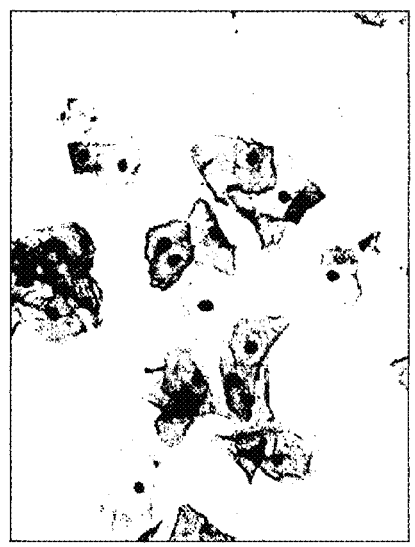

FIG. 6A shows the staining results of a clinical sample diagnosed as normal stained with an anti-HPV E6 mouse monoclonal antibody in an ICC assay according to another embodiment of the invention.

FIG. 6B shows the staining results of the same clinical sample as shown in FIG. 6A stained with an anti-HPV E7 mouse monoclonal antibody in an ICC assay according to another embodiment of the invention.

Figure 7C:
Figure 7B:
Figure 7A:

FIG. 7A shows staining of the cytoplasmic portions of another cervical scrape sample with an anti-HPV E6 mouse monoclonal antibody in an ICC assay according to another embodiment of the invention.

FIG. 7B shows staining of the nuclear portions of the same sample as used in FIG. 7A with an anti-HPV E7 mouse monoclonal antibody.

FIG. 7C shows staining of the cytoplasmic portions of another cervical scrape sample with an anti-HPV E6 mouse monoclonal antibody.

Figure 8A:

FIG. 8A shows the staining results of a clinical sample diagnosed as CIN1 and stained with an anti-HPV E6 mouse monoclonal antibody in an ICC assay according to another embodiment of the invention.

Figure 8C:
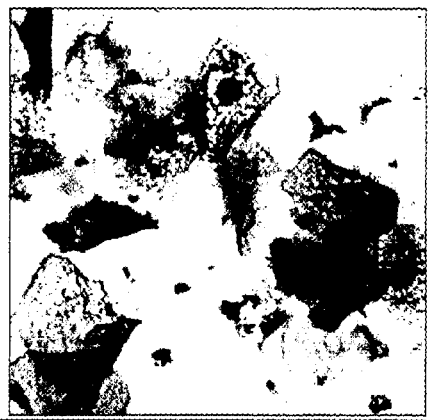
Figure 8B:

FIG. 8B shows another ICC staining image of the same CNI1 sample as shown in FIG. 8A using the same anti-HPV E6 mouse monoclonal antibody.

FIG. 8C shows another ICC staining image of the same CIN1 sample as shown in FIG. 8A using the same anti-HPV E6 mouse monoclonal antibody.

Figure 8E:
Figure 8D:

FIG. 8D shows the staining results of the same CIN1 sample as shown in FIG. 8A but stained with an anti-HPV E7 mouse monoclonal antibody in an ICC assay according to another embodiment of the invention.

FIG. 8E shows another ICC staining image of the same CIN1 sample as shown in FIG. 8D stained with the same anti-HPV E7 mouse monoclonal antibody.

Figure 8F:

FIG. 8F shows the staining results of the same CIN1 sample as shown in FIG. 8A using an anti-p16 mouse monoclonal antibody in an ICC assay according to another embodiment of the invention.

Figure 9:
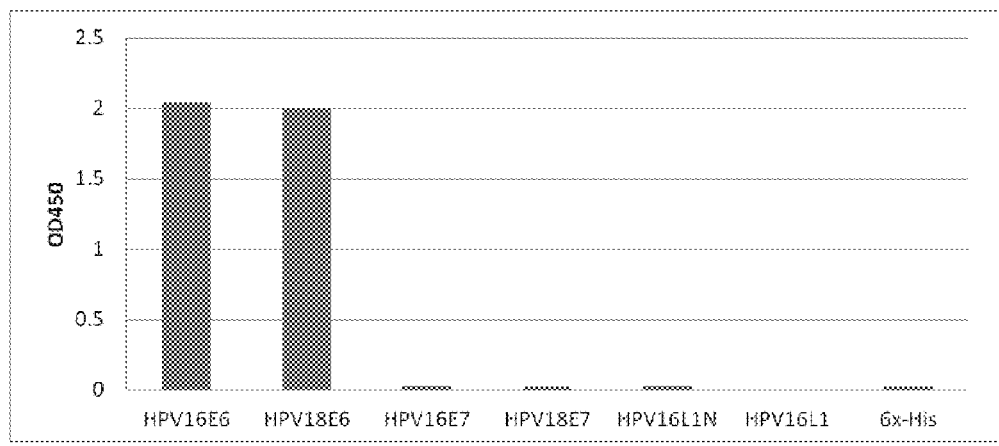

FIG. 9 shows the specificity of a monoclonal antibody capable of binding to two E6 recombinant proteins (HPV16 E6 and HPV18 E6, E6 proteins from different HPV types) and recognizing a common epitope on the two E6 proteins from different HPV types as assayed on EIA according to another embodiment of the invention.

Figure 10:
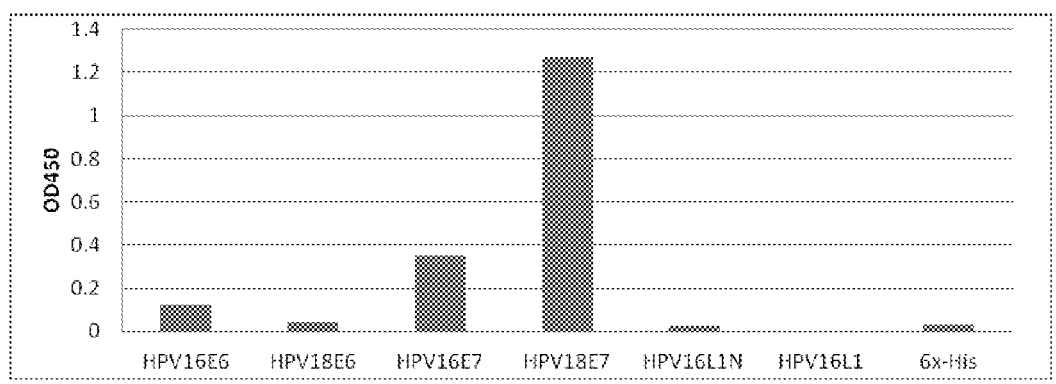

FIG. 10 shows the specificity of a monoclonal antibody capable of reacting with two recombinant HPV16 E7 and HPV18 E7 proteins (E7 proteins from different HPV types) and recognizing a common epitope on the two E7 proteins from different HPV types as assayed on EIA.

Figure 11B:
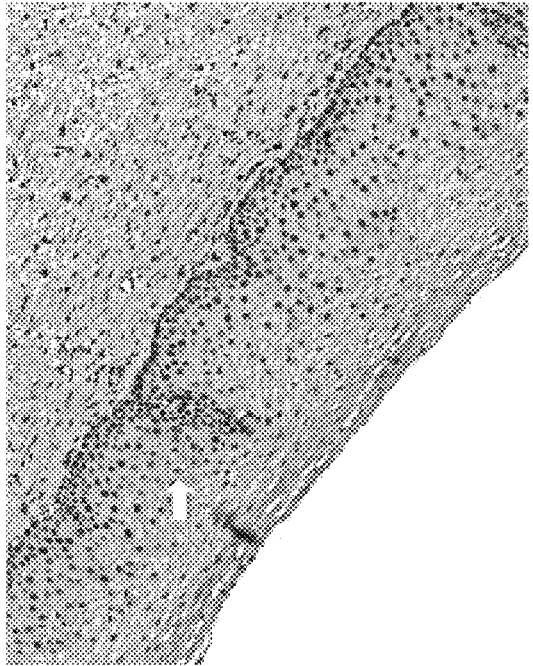
Figure 11D:
Figure 11A:
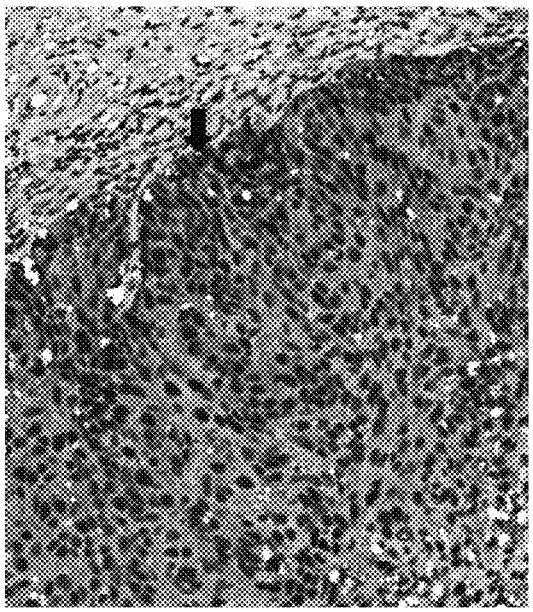

FIG. 11A shows the representative staining image of the dysplasia cells of CIN2 tissues using an anti-E6 monolonal antibody in an immunohistocytostaining (IHC) assay.

FIG. 11B shows the representative staining image of the normal epithelium adjacent to the dysplasia tissue of the CIN2 sample in FIG. 11A.

Figure 11C:
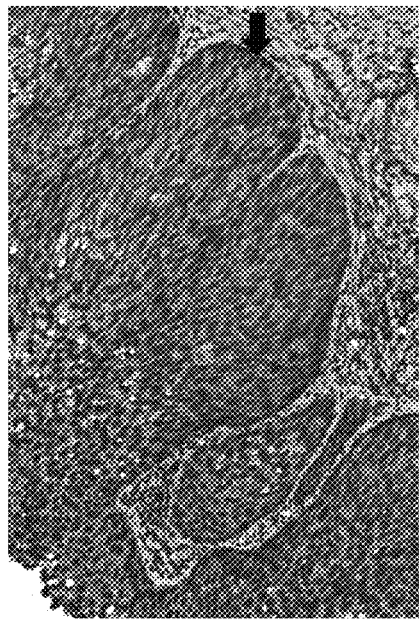

FIG. 11C shows the representative staining image of the dysplasia epithelium of a CIN3 sample stained by the same anti-E6 monolonal antibody as used in FIG. 11A in an IHC assay, demonstrating specific IHC staining in the nuclear and cytoplasm of dysplasia cells by the anti-E6 monoclonal antibody.

FIG. 11D shows the representative staining image of the dysplasia epithelium of another CIN3 sample stained by the same anti-E6 monolonal antibody as used in FIG. 11A in an IHC assay.

Figure 12B:
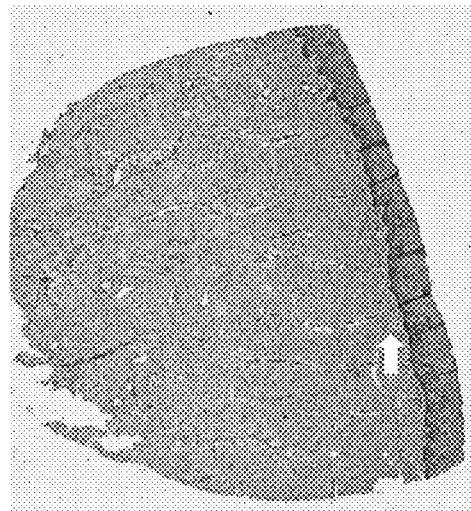
Figure 12D:
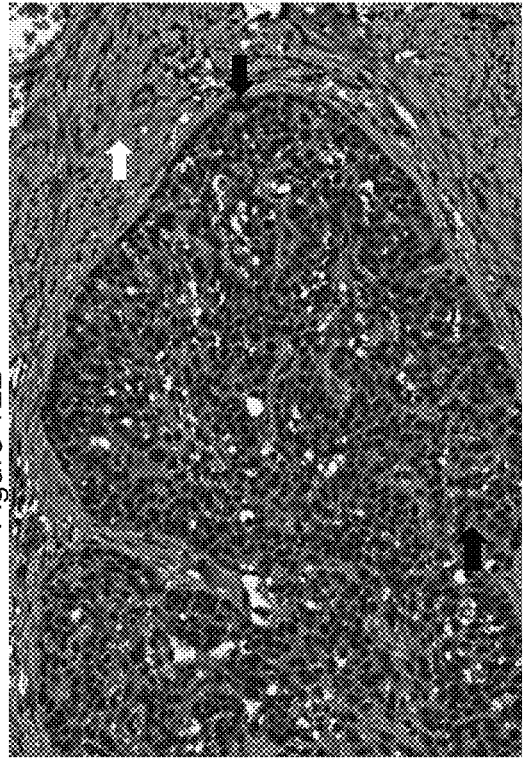
Figure 12A:

FIG. 12A shows the representative staining image of the squamocarcinoma (SCC) tissue from tissue microarray using an anti-E7 monolonal antibody in an immunohistocytostaining (IHC) assay.

FIG. 12B shows the representative staining image of the normal epithelium (about 15 mm away from the tumor tissue) adjacent the SCC tissue of FIG. 12A.

Figure 12C:
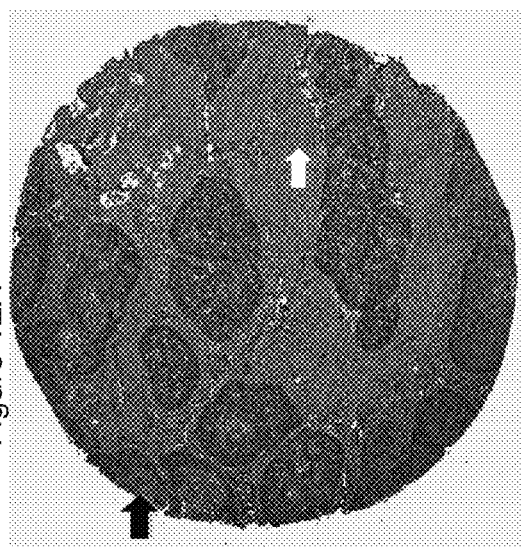

FIG. 12C shows the representative staining image of another SCC sample stained by the same anti-E7 monolonal antibody as used in FIG. 12A in an IHC assay, demonstrating specific IHC staining in the tumor cells by the anti-E7 monoclonal antibody.

FIG. 12D shows the magnified representative image of the tumor cells from FIG. 12C to view the staining of the cytoplasm of the tumor cells.

FIG. 13A shows the representative staining image of cervical cells from a CIN2 cervical scrape sample prepared by thin prep and stained by a mouse monoclonal anti-HPV E7 antibody in an immunocytochemistry (ICC) assay.

FIG. 13B shows the representative staining image of cervical cells from a CIN3 cervical scrape sample prepared by thin prep and stained by a mouse monoclonal anti-E6 antibody in an ICC assay.

FIG. 13C shows the representative image of cervical cells from an adenocarcinoma (ADC) cervical scrape sample prepared by thin prep and stained by the same anti-E6 antibody shown in FIG. 13B in an ICC assay.

DETAILED DESCRIPTION

Embodiments of the invention provide various immunoassays and monoclonal antibodies against HPV viral proteins such that infection by high risk and low risk HPV types can be detected by a single monoclonal antibody and/or a general pan antibody. The invention also provides HPV immunocytochemistry (ICC) assay, HPV flow cytometry assay, and HPV immunohistochemistry (IHC) assay to detect the presence of HPV proteins in situ.

A method for detecting papillomavirus infection in a human subject includes conducting one or more immunological assays, such as an immunocytological assay or a flow cytometry assay on a clinical sample from the human subject and processed into a mixture of morphologically abnormal and normal human cells. In one embodiment, an immunocytological assay is conducted by processing the mixture of human cells into a thin layer of human cells on a slide. The thin layer of human cells can be, for example, a monolayer of cervical cells. The mixture of human cells can be applied to the slide by direct smear or from a liquid based solution. The one or more papillomavirus proteins from one or more papillomavirus types present in the clinical sample is then detected in situ by staining the thin layer of human cells with one or more tagged antibodies generated against one or more purified recombinant papillomavirus proteins. The one or more antibodies can be tagged with different agents suitable in the art for visualization, such as staining agents or detection agents. In one embodiment, at least one antibody of the one or more antibodies is capable of recognizing a papillomavirus early protein. The papillomavirus early protein may be, for example, HPV-16 E6 protein, HPV-16 E7 protein, HPV-18 E6 protein, HPV-18 E7 protein, and combinations thereof.

Another method of detecting papillomavirus infection in a human subject includes conducting a flow cytometry assay on human cells from biological samples obtained from a human subject and provided in a liquid-based solution to detect one or more papillomavirus proteins from one or more papillomavirus types present in the samples. The flow cytometry assay can be conducted to detect each individual cell by separating the one or more human cells in accordance with, e.g., cell size, staining with agents tagged on one or more antibodies, or other criteria. In addition, the presence of one or more proteins from one or more papillomavirus types in the human cells contained in the liquid-based solution of the biological sample is detected by one or more tagged antibodies. The one or more flow cytometry assays are conducted by a group of flow cytometry instruments with a capability to separate and detect each cell individually in a flow format using an appropriate light source for detection.

In another embodiment, one or more immunohistochemical assays on the slide containing the thin section of the clinical tissue sample are conducted to stain the human cells using one or more antibodies generated against one or more purified recombinant papillomavirus proteins, wherein at least one antibody is capable of recognizing a papillomavirus early protein; and detecting in situ one or more proteins from one or more papillomavirus types present in the thin section of the clinical tissue sample on the slide.

In another embodiment, cytological papanicolaou smear assay on the clinical sample was also performed to compare the results of the cytological papanicolaou smear assay with the results of the one or more immunohistological assays. Nucleic acid hybridization assay on the clinical sample was also performed to detect the presence of a papillomavirus genome in the clinical sample from the human subject Embodiments of the invention generally relate to various methods, detection assays, kits, polyclonal and monoclonal antibodies, polypeptides, recombinant proteins, and nucleic acids useful for detecting HPV infection, including general HPV infection as well as infection by various HPV genotypes, high risk HPVs and low risk HPVs. Various novel monoclonal antibodies against HPV proteins, useful as biomarkers and useful tools for detecting HPV viral proteins, HPV oncoproteins, early screening of cervical cancer, and diagnosing CIN and/or invasive cervical and other cancers, are provided. The tools of the inventions can also be used in early clinical screening for HPV infection and general diagnosis for cervical cancer and other cancers, specific detection of invasive cervical cancer, detection of other HPV related cancers, early stage precancerous lesions as well as late stage cancer progression.

In another embodiment, the one or more purified recombinant papillomavirus proteins include recombinant E6 proteins, recombinant E7 proteins, and recombinant L1 proteins from various HPV types. The recombinant papillomavirus proteins include, but are not limited to, recombinant HPV-16 E6 proteins, recombinant HPV-16 E7 proteins, recombinant HPV-18 E6 proteins, recombinant HPV-18 E7 proteins, recombinant HPV-16 L1 proteins, recombinant HPV-18 L1 proteins, and combinations thereof. One embodiment provides various monoclonal antibodies against HPV viral proteins such that infection by high risk and low risk HPV types can be detected by a single monoclonal antibody. The invention also provides HPV type specific monoclonal antibodies for detecting only the high risk HPV types. The one or more papillomavirus types includes high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, and combinations thereof.

In one embodiment, one antibody among the one or more antibodies is capable of recognizing a common epitope present on two or more papillomavirus proteins. The two or more papillomavirus proteins may include a papillomavirus early protein and a late papillomavirus protein and the one antibody is capable of recognizing both the papillomavirus early protein and the late papillomavirus protein. In another embodiment, the one or more antibodies may include antibodies recognizing HPV E6 proteins, antibodies recognizing HPV E7 proteins, antibodies recognizing both HPV E6 and E7 proteins, antibodies recognizing HPV L1 proteins, antibodies recognizing HPV E6 proteins from different HPV types, antibodies recognizing HPV E7 proteins from different HPV types, antibodies recognizing HPV L1 proteins from different HPV types, antibodies recognizing HPV E6 and E7 proteins of the same HPV types, antibodies recognizing HPV E6 and E7 proteins of different HPV types, antibodies recognizing HPV E6, E7, and L1 proteins, and combinations thereof.

The binding of the antibody with the one or more HPV viral proteins from one or more papillomavirus types present in the biological sample are examined under a microscope to detect the presence of an agent reacting with the tagged one or more antibodies, wherein the agent consists of a colormetric agent, a fluorescent chromogen, and combinations thereof. The biological samples consist of cervical cells, cervical tissues, cervical swabs, body fluids, serum, blood, tumors, cell cultures, biopsies, and combination thereof. The biological samples can be obtained from the general population for routine screening of cervical cancer.

As an example, a mouse anti-HPV E6 or anti-HPV E7 monoclonal antibody can be used in an ICC assay in a liquid based solution to detect the presence of HPV E6 or HPV E7 protein in situ on one or more cells fixed on a slide. The liquid based solution can be various liquid based solutions useful for the ICC assay. Using the methods, antibodies, and assays of the invention, HPV E6 or HPV E7 proteins can be detected in situ on cervical scrape samples of a general population with HPV infection at various disease stages. In one embodiment, the immunocytological assay is used to detect a diseased stage caused by HPV infection. The disease stage may be early stage HPV infection, late stage HPV infection, early stage cervical cell lesion, late stage cervical cell lesion, low grade of squamous intraepithelial lesion (LSIL), high grade of squamous intraepithelial lesion (HSIL). atypical squamous cells of undetermined significance (ASCUS), cervical intraneoplasm stages 1, 2, 3 (CIN1, CIN2, CIN3, respectively), developed cervical cancer, adenocarcinoma, or squamous cell carcinoma (SCC). In addition, the same cervical scrape samples can also be processed by standard cytological papanicolaou smear assays to compare the results of the cytological papanicolaou smear assay with the results of the immunocytological assays. Further, the staining pattern and intensities of the mixture of the morphologically abnormal and normal human cells as performed in accordance with the methods and assays of the invention can be compared with the morphology of these human cells.

As another example, immunological assays are performed on cervical scrape samples diagnosed as normal, ASCUS, ASC-H, CIN1, CIN2/3, and HPV E6 viral proteins are detected to be present in these samples with increasing positivity rate, respectively, using an anti-HPV E6 antibody. There is about 92% positive rate for samples diagnosed with pap smear CIN2/3, while only 15% of samples diagnosed as pap smear normal are stained positively in an ICC assay using the anti-HPVE6 antibody. For ASCUS or ASC-H samples, about 33% to 38% of these samples are stained positively by the same anti-HPV E6 antibody as used for the CIN2/3 samples, indicating HPV infection and the expression of oncogenic proteins in these ASCUS or ASC-H samples. Thus, the results from the immunological assays of the invention help to identify the need for these ASCUS or ASC-H human subjects to come back to a medical clinic for follow-up testing of potential cancer development and disease progression. For the ASCUS and ICC clinical samples that are tested negative by the anti-HPV E6 antibody in ICC assay, it can be predicted that there is less risk to develop progressive HPV-related cervical lesions. Accordingly, the results of the ICC staining assay using the anti-HPV E6 antibody give a sensitivity of 83% for CIN2+ with specificity of 85%. These data suggest this assay can be useful to detect HPV proteins for screening of cervical cancer from the general population along with routine pap smear staining. Similar ICC results were also found in the same samples using anti-HPV E7 antibodies.

In a further embodiment, a nucleic acid hybridization assay can also be performed on the clinical sample to detect the presence of a papillomavirus genome in the clinical sample from the human subject. The nucleic acid hybridization assays consist of polymerase chain reactions, nucleic acid hybridization assays, DNA chip assays, radioactive nucleic acid hybridization and detection assays, and non-radioactive nucleic acid hybridization and detection assays.

In another embodiment, one or more flow cytometry assays was conducted to detect individual cells by separating the one or more human cells with or without staining, and detecting the presence of one or more proteins from one or more papillomavirus types in the one or more human cells contained in the liquid-based solution of the biological sample. The one or more flow cytometry assays are conducted by a group of flow cytometry instruments with a capability to separate and detect each cell individually in a flow format using an appropriate light source for detection.

As an example, cells from cervical scrapes were collected, centrifuged, washed, and immunostained followed by the ICC procedure described herein. The HPV E6, E7, or L1 protein can be detected by the specific antibody followed by the $2^{nd}$ antibody labeled with fluorescent dye (FITC, PE, Cy5, etc. conjugated). The cells analyzed by flow cytometry can be gated by size or other parameters to look at the cell population with or without staining. The stain intensity from cell population with smaller cell size can be compared to the cell population with bigger cell size as a control of normal cells in the assay. This assay provides specific staining for individual cells. The number of cells stained or unstained can be counted, and the intensity of staining can also be quantitated by analysis. This assay can be high throughput, requires no microscope, nor cytologist to score the staining results. The powerful computer software from the flow cytometry provides all data for analysis with no bias nor trained personnel in cytology required. This assay should apply well in the clinical setting as screening test or accompanion test for detection of HPV associated proteins.

In another embodiment, one or more immunohistochemical assays on the slide containing the thin section of the clinical tissue sample was conducted to stain the thin layer of human cells using one or more antibodies generated against one or more purified recombinant papillomavirus proteins, wherein at least one antibody is capable of recognizing a papillomavirus early protein; and detecting in situ one or more proteins from one or more papillomavirus types present in the thin section of the clinical tissue sample on the slide. Results of a cytological papanicolaou smear assay on the clinical sample were compared with the results of the one or more immunohistological assays.

For example, a number of cervical biopsy samples are tested in an immunohistochemistry (IHC) assay concurrently as a tissue microarray format using a monoclonal antibody to detect HPV proteins from a variety of HPV types (as confirmed by HPV DNA genotyping). Using a monoclonal antibody against HPV oncoprotein E7, the invention provides detection of the presence of HPV E7 protein in clinical samples having either single HPV infection or multiple HPV infections. A single anti-E7 monoclonal antibody as described herein can detect single HPV infection by at least HPV-6, HPV-16, HPV-18, HPV-31, HPV-33, HPV-52, etc, which are cancer-related HPV types (either high risk HPV types or low risk HPV types). A single anti-E7 monoclonal antibody can detect HPV infection by two or more HPV types, such as the combination of HPV-16, HPV-18, HPV-52, HPV-58, HPV-44, HPV-51, HPV-39, HPV-59, etc., which include high risk, low risk, and non-oncogenic α-papillomaviruses.

Two problems exist such that there is no antibody available to do clinical HPV diagnostics. One is that HPV proteins in clinical sample are present in very small quantities. Secondly, the HPV types in the clinical sample are generally unknown. Therefore, people skilled in the art failed and were not able to produce HPV antibodies that recognize various clinical HPV types in significant quantity, despite this long felt need. For an antibody in a diagnostic test to be successfully useful, the antibody must recognize an epitope which is present on the immunogen and the epitope can be exposed in the test sample being prepared for analysis (i.e., exposed after any pre-treatment of tissues such as cryopreservation, sectioning and fixing). Therefore, the method chosen for screening large numbers of hybridoma culture supernatants must be such that it aids selection of diagnostically useful antibodies. There has been failure in purifying and obtaining recombinant HPV proteins and in producing antibodies from purified recombinant proteins for screening HPV infection and the need has not been met.

Accordingly, one embodiment of the invention provides a monoclonal antibody capable of recognizing a common epitope on E6 protein from two different HPV types, both HPV16 and HPV18 by screening antibody-producing hybridoma cells with a purified HPV16 E6 recombinant protein and a purified HPV18 E6 recombinant protein. Another embodiment of the invention provides a monoclonal antibody that recognizes a common epitope on HPV16 E7 and HPV18 E7 proteins. Still another embodiment of the invention provides a monoclonal antibody that recognizes a common epitope on HPV16 E6, HPV16 E7, HPV16 L1, HPV18 E6, and HPV18 E7 proteins.

In still another embodiment, a monoclonal antibody capable of recognizing a specific epitope on only one HPV viral protein, but not another HPV viral protein is obtained by screening antibody-producing hybridoma cells with a first purified recombinant papillomavirus protein from a first HPV type and a second purified recombinant papillomavirus protein from a second HPV type, wherein the one and another viral proteins correspond to the first and the second purified recombinant papillomavirus proteins of the first and second HPV types.

In another embodiment, various monoclonal antibodies against HPV proteins, E6, E7 or L1 (anti-HPV E6, anti HPV E7, anti-HPV-L1) are provided including those monoclonal antibodies specific for detecting HPV types correlated with the immunogens with which the antibodies were raised, and other non-HPV type-specific monoclonal antibodies. The antibodies of the invention include, but are not limited to, anti-E6, anti-E7, and anti-L1 antibodies, etc., and are used in one or more immunological assays. For example, the monoclonal antibodies can be used to test various biological samples, cell lines, and/or clinical samples of various grades of epithelial lesions (CIN2, CIN3, LSIL, HSIL, ASCUS) as well as different cervical cancers, squamascarcinoma (SCC, a type of common cancer) and adenocarcinoma (ADC, a type of gland cancer).

In one embodiment, a method of screening a human subject of papillomavirus infection includes obtaining a clinical sample from the human subject, and conducting one or more immunological assays on the clinical sample from the human subject using various HPV recombinant proteins and lab-generated antibodies specific for HPV oncoproteins in order to detect and screen for the presence of HPV infection from the presence of HPV proteins and HPV antibodies in the human subject. In another embodiment, the HPV proteins in the human subject are detected using antibodies raised against HPV recombinant proteins including, but not limited to, various polyclonal and monoclonal antibodies against various HPV early and late proteins.

The antibodies as developed herein lend themselves to the high quality and properly purified recombinant proteins encoded by HPV early and late genes, useful in immunological assays to generate very high sensitivity and specificity for screening HPV infection and cervical cancer detection. The monoclonal antibody can be used for one or more immunological assays selected from the group consisting of ELISA (enzyme linked imunoabsorbant assays), antigen assays for papillomavirus proteins, antibody assays for antibodies against papillomavirus proteins, assays for papillomavirus immunocomplexes, protein chip assays, radioimmunoprecipitation assays, rapid membrane immunochromatographic assays, rapid stick immunochromatographic assays, immunohistochemistry for tissues and/or cervical cells, and immunocytological assays followed by flow cytometry, among others. In one embodiment, the one or more immunological assays may be non-invasive with minimal or no additional instruments required.

The basic techniques for conducting the immunological assays can be found in "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals known in the art. The related immunological assays, immunohistochemistry for tissues and/or cervical cells, and/or immunocytological assays followed by flow cytometry can also be found in issued U.S. Pat. No. 7,732,166 filed on Nov. 13, 2006, titled "Detection method for human papilloma virus (HPV) and its application in cervical cancer"; issued U.S. Pat. No. 7,972,776 filed Apr. 14, 2008, titled "Protein chips for HPV detection"; Ser. No. 61/131,991, filed Jun. 13, 2008 titled "Antibodies and assays for HPV detection"; Ser. No. 61/192,912 filed on Sep. 22, 2008, titled "Novel monoclonal antibodies against HPV proteins"; issued U.S. Pat. No. 8,865,162 titled "Novel monoclonal antibodies against HPV proteins" filed Jun. 10, 2009"; issued U.S. Pat. No. 8,278,056 titled "Detection of early stages and late stages HPV infection" filed on Jun. 10, 2009. All of the above referenced applications are herein incorporated by reference.

In one embodiment, the invention also provides various methods, detection assays, and kits, polyclonal and monoclonal antibodies, polypeptides, recombinant proteins, and nucleic acids useful for detecting general HPV infection as well as infection by various HPV genotypes, high risk HPVs and low risk HPVs. In addition, the assays or sample formats in detecting the presence of HPV proteins are not limited and can be used for cervical tissues, cervical cells, cervical scrapes, serum, body fluids, etc. The useful screening or diagnosing assay can be IHC, ICC, flow cytometry, antibodies coupled to beads, rapid tests, protein chips, dot blots, slots, as well a conventional ELISA assay. HPV proteins can be detected by the antibodies of the invention to be present in epithelium tissue as evidenced by IHC staining after scoring by a pathologist.

The antibodies described in this invention provide a tool to detect HPV proteins present in various sources of biological samples. As an example, the antibodies described herein can be used as a capture antibody to coat on microtiter plate and/or used as a detection antibody as a sandwich format of ELISA (Enzyme Linked Immuno Sandwich Assay). Depending on the target HPV proteins and/or HPV types, antibodies can be selected to use based on the specificity described herein of monoclonal antibody to particular HPV proteins or HPV types, or in combinations thereof. The detection antibody from selected specificity of monoclonal antibodies described herein can be directly conjugated with a label like biotin, alkalin phosphatase, HRP, flourecent, etc., followed by color metric, chemiluminescent or fluorescent substrate for readout. The detection antibody can also be selected from the polyclonal antibodies described herein and followed by a secondary antibody conjugated with a label like biotin, alkalin phosphatase, HRP, flourecent, etc. Combination of using polyclonal and monoclonal antibodies for the sandwich ELISA as capture and detection antibodies or vice versa, increases assay sensitivity by incorporating a secondary antibody to amplify the signal for detection. For direct EIA (Enzyme Immuno Assay), cells, samples or cultured cells to be tested were collected and lysed to generate cell lysate as analyte. The protein in the cell lysate was quantitated and coated to microtiter plate using the same amount of protein for coating in each well followed by the detection antibody with specificity described in this invention.

Detection of HPV DNAs, genomes, early viral proteins, late viral proteins, oncoproteins, and/or capsid proteins from various HPV genotypes can be performed by various in vitro and in vivo method and detection assays according to "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals and can be very useful in general clinical screening for HPV infection.

Detection of HPV antibodies and/or oncoproteins by immunological assays can be used in early clinical screening for HPV infection and general diagnosis for cervical cancer and can be performed in a single rapid test or in multiplexed test. Comparative detection of altered levels of HPV proteins and host proteins can be performed in the same or different assays. It can also be used in diagnosing HPV-associated carcinomas of the uterine cervix, as well as those cases associated with epithelial cell abnormalities induced by HPV infection, pre-malignant and malignant HPV-associated epithelial cell lesions, and those at risk of developing HPV-associated cervical carcinoma and adenocarcinoma. The methods as described herein can be used independently or as an adjunct screening tool to convention cytological papanicolaou smear tests or histological tests and the results thereof can be compared for follow-up patient management.

EXAMPLES

1. Expression, Purification, and Preparation of HPV Recombinant Proteins to be Used as Immunogens for Generating Antiserum and Anti-HPV Antibodies, and Screening Hybridoma Cell Lines for Monoclonal Antibodies HPV recombinant proteins can be any kinds of HPV proteins, HPV proteins of early genes and/or late genes, including, but not limited to, E2, E6, E7, L1, L2 and can be from various HPV types. Full-length E6, E7, and/or L1 polypeptide sequence, which have been found very difficult to obtain and purify due to undesirable aggregation during protein purification, protein instability, low levels of expression, low immunogenic responses of purified proteins. For example, many early E6 oncoproteins contain many cysteine amino acids and thus the correct topography of the E6 oncoproteins requires formation of many disulfide bonds properly. In addition, it was known that certain immunological assays using small peptides of early E6 and E7 proteins results in extremely low assay specificity and sensitivity and are thus unsuitable as tools for clinical in vitro diagnostics. Thus, the invention provides recombinant proteins, such as recombinant hybrid proteins containing a partial sequence or a full length sequence of HPV oncogenic proteins.

1). Cloning and production of various recombinant proteins encoded by HPV16 E6 and HPV18 E6 gene. An exemplary oncogenic E6 early gene from an exemplary HPV type, HPV-16, was cloned. The HPV 16 E6 gene cloned herein is a 474 base pair (b.p.) DNA fragment containing the 157 amino acid coding region of the whole HPV-16 E6 gene and was obtained by polymerase chain reaction (PCR) amplification. The DNA sequence of the isolated DNA fragment was confirmed by comparing with the sequence from Gene Bank database. Recombinant HPV-18 E6 protein was also obtained. All cloning procedures are carried out according to the protocols described in "Molecular Cloning", A Laboratory Manual, eds. Sambrook, Fritsch and Maniatis, Cold Spring Harbor Laboratory Press, 1989. In addition, HPV18 E6 gene was also cloned and the DNA sequence was confirmed.

2). Cloning and production of various recombinant proteins encoded by HPV16 E7 and HPV18 E7 gene. An exemplary oncogenic E7 early gene from an exemplary HPV type, HPV-16, was cloned. A 294 base pair (b.p.) DNA fragment containing the 99 amino acid coding region of the entire HPV-16 E7 gene was obtained by polymerase chain reaction (PCR) amplification. The DNA sequence of the isolated DNA fragment was confirmed by comparing with the sequence from Gene Bank database. Recombinant HPV-18 E7 protein was also obtained In addition, E7 DNA fragments from different HPV types can also be cloned from different clinical samples or sources.

3). Cloning and production of various recombinant proteins encoded by HPV16 L1 and HPV18 L1 gene. An exemplary late gene from an exemplary HPV type, HPV-16, was cloned. A 1596 base pair (b.p.) DNA fragment containing the 531 amino acid coding region of the HPV-16 L1 gene was obtained by polymerase chain reaction (PCR) amplification. The DNA sequence of the isolated DNA fragment was confirmed by comparing with the sequence from Gene Bank database. In addition, L1 DNA fragments from different HPV types can also be cloned from different clinical samples or sources.

A recombinant N-terminal fragment of HPV 16 L1 protein was also obtained from a His-tagged expression system. The molecular weight of the HPV-16 L1 N-terminal recombinant protein is about 34 KD. L1 C-terminal fragments can also be obtained. Recombinant HPV-18 L1 protein was also obtained and used as immunogens for generating antiserum, polyclonal and monoclonal antibodies.

The one or more recombinant proteins described herein can be expressed in various suitable systems, such as bacterial expression systems, viral expression systems, yeast expression systems, mammalian expression systems, e.g., in $E\ coli$, yeast, baculovirus, and/or mammalian cell cultures, generally known in the field. Although the polypeptides could be obtained by other means, embodiments of the invention provide one or more recombinant proteins mostly in (or close to) their native forms, which may be a much desirable conformation for binding with antibodies from tissues of human subjects with HPV infection in an immunological assay. For example, GST, MBP, or His tagged-HPV16-E6, HPV18 E6, HPV16 E7, HPV18 E7, HPV16 L1, and HPV18 L1 recombinant proteins were expressed in $E.\ coli$ BL21(DE3) using IPTG driven induction. After induction of protein expression, tagged-HPV recombinant proteins were obtained from soluble fraction after lysis of the cultured cells and purified to a final concentration of about 0.1 to 1 mg/ml or higher. The purity of the recombinant HPV proteins was estimated to be >90% based on PAGE analysis. Recombinant HPV proteins were used to detect the presence of HPV antibody on clinical samples and were also used as immunogens for producing polyclonal antiserum and monoclonal antibodies.

The cell culture containing various recombinant papillomavirus proteins in various expression vectors as described herein are then scaled up to 1 liter or 10 liter, or 100 liters or higher to obtain high quantity of soluble recombinant protein for purification. After cell lysis the soluble fraction was passed through various chromatography columns with appropriate expression systems to bind to the tag expressed along with the HPV recombinant proteins. The tag-HPV recombinant proteins were then eluted from the column and concentrated down to 100 ml or 10 ml to 1 ml. The purified soluble recombinant HPV proteins were further concentrated and dialyzed with buffers at neutral pH or PBS buffers to be used as immunogen to generate antiserum against the HPV proteins. The soluble recombinant HPV proteins were thus purified from soluble fractions and folded close to their native folding states as in vivo natural conditions.

Obtaining high quality purified recombinant HPV proteins is critical in generating various types of monoclonal antibodies that recognize common epitopes or specific epitopes for detecting HPV infection. The purified recombinant HPV proteins were tested to confirm their binding to the HPV antibody from the HPV infected clinical samples. Thus, such purified recombinant HPV proteins are suitable for use as immunogen to raise antiserum and generate antibodies that can recognize natural HPV viral proteins in vivo.

2. Anti-HPV Polyclonal Antibody Production

Recombinant HPV E6, E7 or L1 proteins expressed in *E coli* were purified, concentrated, and dialyzed with PBS to be used as immunogens. Immunization was followed by standard protocol. Titer of each serum obtained was tested by ELISA assays followed by periodical boosting and bleeding. Production bleed from optimal titer was collected; processed serum was used to do immunoglobulin (Ig) purification via protein A columns or affinity columns. Purified IgG was used as anti-HPV antibodies for HPV immunoassays.

Monoclonal antibodies, polyclonal antibodies, and antiserum were obtained, purified, and tested herein to be able to detect HPV infection regardless of the pathogenesis of HPV infection, cell lesions, inflammatory, or cancer disease development. Other researchers have tried to develop anti-HPV monoclonal antibodies but have failed because they failed to generate sufficient HPV proteins for monoclonal antibodies production; they failed to generate monoclonal antibodies with high specificity because the immunigens were not immunogenic, or the generated antibodies were not able to recognize native forms of HPV proteins present in clinical samples with early stage HPV infection. Some antibodies raised against mutant peptides were only able to recognize late stage cervical cancer, but there was uncertainty whether the antibodies would recognize wild type HPV native proteins or any early stage HPV infection. In addition, late stage HPV detection is too late for disease intervention and treatment.

The clinical utility of the antibodies described herein was validated by HPV immunoassays, such as ELISA assays, immunocytochemistry assays, immunohistochemistry assays, using appropriate clinical samples. The novel monoclonal antibodies and antiserum, obtained from methods of this invention are able to interact and bind HPV viral proteins present in clinical samples, which have been confirmed to contain early stage cell lesions such as cervical intraepithelial neoplasia (CIN) as well as late stage HPV associated cervical cancer. The monoclonal antibodies and antiserum as described herein provide powerful tools to detect and screen HPV related pathogenesis and cervical cancer development in both early stages and late stages and thus provides an avenue to intervene disease progression and a chance to provide early treatment.

3. HPV Monoclonal Antibody Development

Recombinant HPV E6, E7 or L1 proteins expressed in *E coli* were purified, concentrated, and dialyzed with PBS to be used as immunogen. Immunization of mice was followed by standard procedure. Titer of the obtained serum was tested by ELISA followed by periodical boosting and bleeding. When the titer of the serum of the mice reaches optimal, fusion of the spleen cells of the mice with tumor cells was done by standard procedure. Clones of fused cells, e.g., hybridoma cells, were further cultured.

1). Hybridoma screening: To obtain anti-HPV antibody producing hybridoma cells with pan and specific binding capability to various HPV proteins as described in this invention, hybridoma clones were screened with various proteins, including, not only the original immunogens but also additional HPV proteins as positive screening, and unrelated proteins as negative screening. For example, two or more purified HPV recombinant proteins were used to screen against each hybridoma clone to screen and obtain monoclonal antibody-producing hybridoma cell lines and to test and understand the specificity of each antibody-producing hybridoma cell line obtained.

As an example of hybridoma screening, antibody-producing hybridoma cells were screened with two or more purified recombinant human papillomavirus proteins such that the monoclonal antibody is capable of reacting with the two or more purified recombinant human papillomavirus proteins. The two or more purified recombinant human papillomavirus proteins include, but are not limited to, HPV 16 E6 protein, HPV 16 E7 protein, HPV 16 L1 protein, HPV 18 E6 protein, HPV18 E7 protein, HPV 18 L1 protein, and other HPV early proteins and late proteins from various HPV types.

The antibody-producing hybridoma cells were screened with positive reactivity to all of the two or more purified recombinant human papillomavirus proteins and negative reactivity to non-HPV proteins, including BSA, his$_6$ tags, GST proteins, maltose binding proteins (MBP), other tags or proteins used in recombinant protein, and other readily available non-HPV proteins. As such, the monoclonal antibodies generated form such hybridoma screening are capable of binding to all of the two or more HPV viral proteins (e.g., the HPV viral proteins present in clinical samples), which correspond to the two or more purified recombinant human papillomavirus proteins.

Examples of the two or more purified recombinant human papillomavirus proteins are HPV early proteins such that the monoclonal antibody is capable of reacting with the two or more human papillomavirus early proteins. For example, one hybridoma cell line screened and obtained can produce a monoclonal antibody recognizing a common epitope on both HPV16 E6 and HPV16 E7 proteins. Another hybridoma cell line screened and obtained can produce a monoclonal antibody recognizing a common epitope on both HPV18 E6 and HPV18 E7 proteins.

Another example of the two or more purified recombinant human papillomavirus proteins includes a purified recombinant human papillomavirus early protein and a purified recombinant human papillomavirus late protein such that the monoclonal antibody produced is capable of reacting with a common epitope on the purified recombinant human papillomavirus early protein and the purified recombinant human papillomavirus late protein. The purified recombinant human papillomavirus early protein may be HPV 16 E6 protein, HPV 16 E7 protein, HPV 18 E6 protein, HPV18 E7 protein, and other HPV recombinant early proteins, and the purified recombinant human papillomavirus late protein may be HPV 16 L1 protein, HPV 18 L1 protein, and other HPV recombinant late proteins. For example, hybridoma cell lines screened and obtained can produce a monoclonal antibody recognizing a common epitope on HPV16 E6, HPV16 E7, and HPV16 L1 proteins; or a monoclonal antibody recognizing a common epitope on HPV16 E6 and HPV18 E6 proteins; or monoclonal antibody recognizing a common epitope on HPV16 E7 and HPV18 E7 proteins; or monoclonal antibody recognizing a common epitope on HPV16 E6, HPV16 E7, HPV16 L1, HPV18 E6, and HPV18 E7 proteins. More examples are provided in the drawings of this invention.

The antibody-producing hybridoma cells were also screened with a first purified recombinant human papillomavirus protein from a first HPV type and a second purified recombinant human papillomavirus protein from a second HPV type such that the monoclonal antibody is capable of reacting with a common epitope on human papillomavirus proteins from two or more different HPV types. The first and the second HPV types can be HPV 16, HPV 18, and other HPV types. The two or more different HPV types can be, for example, high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56. As an example, the first and the second purified recombinant human papillomavirus proteins may be recombinant HPV 16 E6 protein, recombinant HPV 16 E7 protein, recombinant HPV 16 L1 protein, recombinant HPV 18 E6 protein, recombinant HPV18 E7 protein, and recombinant HPV 18 L1 protein.

As another example of hybridoma screening, antibody-producing hybridoma cells were screened with positive reactivity to some of the two or more purified recombinant human papillomavirus proteins and negative reactivity to some of the two or more recombinant human papillomavirus proteins and/or non-HPV proteins. As such, the monoclonal antibodies generated form such hybridoma screening are capable of binding to some HPV viral proteins but not other HPV viral proteins.

For example, a monoclonal antibody was obtained by screening antibody-producing hybridoma cells with a first purified recombinant human papillomavirus protein from a first HPV type and a second purified recombinant human papillomavirus protein from a second HPV type such that the monoclonal antibody is capable of reacting with a specific epitope on only one of the first and the second purified recombinant human papillomavirus proteins and not the other purified recombinant human papillomavirus protein. Specific monoclonal antibodies obtained include a monoclonal antibody capable of binding to only HPV 16 E6 protein but not any other HPV proteins, a monoclonal antibody capable of binding to only HPV 16 E7 protein but not any other HPV proteins, a monoclonal antibody capable of binding to only HPV 16 L1 protein but not any other HPV proteins, a monoclonal antibody capable of binding to only HPV 18 E6 protein but not any other HPV proteins, and a monoclonal antibody capable of binding to only HPV 18 E7 protein but not any other HPV proteins.

2). Hybridoma cell line stocks: Hybridoma cell line clones with desired positive reactivity and desired negative reactivity as judged by an immunoassays (e.g., ELISA, EIA and other assays) were selected and cloned down to a single cell. Each single cell clone was then grown up by tissue culture. When the cell numbers reach millions of cells per ml, the cells were frozen down and kept at −80° C. or in liquid nitrogen as storage stocks.

3). Ascites production: Each hybridoma cell line was grown in tissue culture and injected into mice for ascites production. Ascites were collected and processed for immunoglobin purification by protein G columns. Purified immunoglobin from each hybridoma cell line was isotyped and used for HPV immunoassays.

4. The HPV Immunocytochemical (ICC) Assays

Sample preparation: Clinical cervical samples can be prepared for performing the ICC immunoassay by a conventional pap smear sample-obtaining technique which collects cervical cells from cervical scrape and directly smears on one or more slides. Alternatively, a cytology sample-preparation technique which collects cervical sample in a liquid based solution can be used for sample preparation. These cervical scrapes or cervical cells in the liquid-based solution were divided into two parts, one for cytological papanicolaou staining, the other for immunocytochemical staining using the various anti-HPV antibodies as described herein.

For Pap smears, each sample was scored from 0-17 after papanicolaou staining: a score of one (1) to three (3) is considered as normal, and four (4) and above as abnormal. The abnormal cells include a different stage of squamous cells in development of dysplasia or lesions. Examples include, low grade of squamous intraepithelial lesion (LSIL), high grade of squamous intraepithelial lesion (HSIL), cervical intraepithelial neoplasia with mild cell abnormalities (CIN1), cervical intraepithelial neoplasia with lesions appearing more aggressive (CIN2), and cervical intraepithelial neoplasia with aggressive form of dysplasia. Invasive cancers may include squamous cell carcinoma (SCC) adenocarcinoma (ADC), and others. For samples with abnormal cells that can not be determined, they may be scored as atypical squamous cells of undetermined significance (ASCUS), unusual or atypical cells in pap smear that may be inconsequential, or as atypical glands of undetermined significance (AGUS). For these abnormal cells identified by pap smear scores, further ICC assays by staining with anti-HPV antibodies may provide additional information for the status of HPV infection, cell lesions stages, disease progression, and/or confirm the expression of HPV oncoproteins. Therefore, ICC staining assay with anti-HPV antibody is very useful to detect abnormal cells at either LSIL or HSIL lesion stages, and/or those underdetermined abnormal cells (e.g., ASCUS, or AGUS). The results of ICC immunoassays can also be compared to the scores of the papanicolaou staining.

As an example of an ICC immunoassay, cells from cervical scrapes were directly smeared on the slides for immunostaining. As another example, cervical cells are collected into a liquid-based solution, centrifuged, washed, followed by immunostained with anti-HPV antibody. Cervical scrapes collected by liquid-based solution were processed according to the manufacture's instruction. The cervical cells were then processed by cytospin or thin prep techniques into a monolayer on a slide.

The thin layer of cells on the slide were then fixed and stained by the various anti-HPV antibodies of the invention. The anti-HPV antibodies may be tagged directly with a detection agent or may be detected by a secondary antibody tagged with a detection agent. Cells stained by the anti-HPV antibody were visualized under microscope.

In one embodiment, a kit for performing an ICC assay is provided. The kit may include an pre-antibody blocking solution, post-antibody blocking solution, an anti-HPV antibody as the primary antibody, an anti-mouse or anti-rabbit immunoglobulins conjugated with HRP or biotin, or other agents as secondary antibody, and a solution containing appropriate agents used as substrate for the secondary antibody to be detected.

The anti-HPV antibodies may also be directly tagged with HRP or biotin, or other agents to be detected following appropriate agents used as substrate. The pre-antibody blocking solution may contain certain proteins or BSA, or serum or other agents to block the cells from nonspecific binding of antibody. The post blocking solution may contain similar solution as the pre-antibody blocking solution with less proteins or serum to be used along with primary antibody incubation. The solution containing HPV antibodies may be in concentrated form, or may be in diluted form as ready to use reagent. The solution containing secondary antibodies may be in concentrated form, or may be in diluted form as ready to use reagent. The solution containing appropriate agents used as substrate may include DAB (3.3'-diaminobenzidine) as one component, or two components, or AEC (3-Amino-9-Ethylcarbazole) substrate as one component, or two components, or other substrates.

Once the human cells from cervical scrapes are processed and fixed into a monolayer or thin layer of cells on the slide, the Immunocytochemistry (ICC) assay is performed by blocking the slides with pre-antibody blocking solution for a period of time prior to incubating with the HPV antibodies. The slides were then washed 3 to 5 times with PBS or H2O, or another solution to remove any unbound HPV antibody. Then the slides were incubated with the secondary antibody, for example, anti-mouse IgG HRP, followed by appropriate substrate for detection. As an example, DAB is oxidized in the presence of peroxidase and hydrogen peroxide resulting in the deposition of a brown, alcohol-insoluble precipitate at the site of enzymatic activity. The precipitate may range in color from a light golden brown to dark golden brown depending upon the amount of enzyme present. The golden brown precipitate viewed under a microscope indicates the specific binding of HPV antibodies with HPV proteins present in the cells. The assay can be performed at room temperature or higher temperatures to accelerate the binding reaction. This HPV ICC assay can be performed manually, or operated by ICC automation, and thus provides a powerful tool to screen for HPV infection and detect HPV oncoproteins in situ localized in the epithelium cells from cervical scrapes.

To demonstrate the HPV ICC assay can be applied to different stages of dysplasia cells, samples from early, intermediate, or late stage of neoplasia are all tested. These samples include, but are not limited to, early stages like LSIL, or CIN1, or ASCUS, or intermediate stages like CIN2, CIN3, or HSIL, or late stages like SCC or ADE or others. To demonstrate the ICC assay described herein can be used to stain for various stages in samples from various sources, different stage of samples in different liquid based solutions were also prepared to perform ICC assay in this invention.

Figure 1B:
FIG. 1B shows the staining results of the same clinical sample as shown in FIG. 1A using an anti-HPV E7 mouse monoclonal antibody in an ICC assay according to another embodiment of the invention.
Figure 1A:
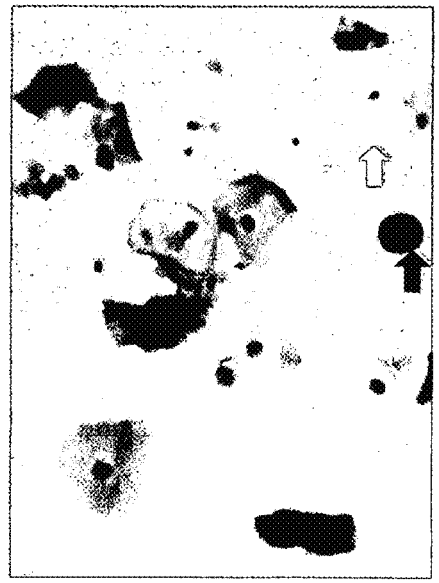
FIG. 1A shows the staining results of a clinical sample, diagnosed as ASCUS, in a liquid based solution using an anti-HPV E6 mouse monoclonal antibody in an ICC assay according to one embodiment of the invention.

To demonstrate HPV ICC assays are useful to identify abnormal cells underdetermined by standard cytological papanicolaou staining, for example, ASCUS (Atypical Squamous Cells of Undetermined Significance, atypical squamous cells of undetermined significance (ASCUS), unusual or atypical cells in pap smear that may be inconsequential or atypical glands of undetermined significance (AGUS), the HPV ICC assays are performed to test for ASCUS and AGUS samples. As shown in FIG. 1A, the results of ICC assay demonstrate that certain cervical scrape cells diagnosed as ASCUS by papanicolaou staining can be ICC stained positively using an anti-E6 monoclonal antibody. FIG. 1B shows the results of ICC assay from the same sample shown in FIG. 1A to demonstrate certain cervical scrape cells (diagnosed as ASCUS by papanicolaou staining) can be ICC stained positively using an anti-E7 monoclonal antibody. As shown in FIG. 1A and FIG. 1B, the abnormal cell with high N/C (nuclear/cytoplasm) ratio (indicated by black arrow) was stained positively while the normal cells (big, irregular cell shape with small nuclear) stain negatively as indicated by the white arrow. Both FIG. 1A and FIG. 1B demonstrate HPV E6 and HPV E7 proteins can be detected in the abnormal cells from samples with pap smear ASCUS. These results indicate that this ASCUS sample containing HPV infected cells with E6 and E7 oncogenic proteins expressed, thus can be detected in situ using the mouse monoclonal anti-HPV E6 and the mouse anti-HPV E7 monoclonal antibody respectively, by the ICC assay described in this invention.

Figure 2B:
FIG. 2B shows the staining results of another clinical sample, diagnosed as CIN2, in a liquid based solution using an anti-HPV E6 mouse monoclonal antibody in an ICC assay according to another embodiment of the invention.
Figure 2A:
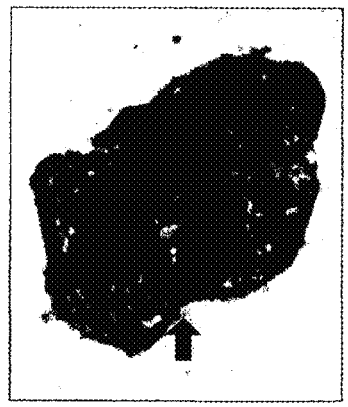
FIG. 2A shows the staining results of a clinical sample, diagnosed as CIN2, in a liquid based solution using an anti-HPV E7 mouse monoclonal antibody in an ICC assay according to one embodiment of the invention.

To demonstrate the HPV ICC assay can detect HSIL cells, FIG. 2A shows cervical scrape cells diagnosed as CIN2 by papanicolaou staining. These cells were prepared in another liquid-based solution and are ICC-stained positively using an anti-E7 monoclonal antibody. As shown in FIG. 2A, the CIN2, HSIL abnormal cells are stained positively to the nucleus and cytoplasm. These cells are in the form of connecting each other with high nuclear to cytoplasm (N/C) ratio as indicated by the black arrow. These results demonstrate that HPV E7 protein present in situ can be detected in the abnormal cells from an intermediate stage of neoplasm, in various liquid-based solutions using the mouse monoclonal anti-HPV E7 described herein.

As an another example, FIG. 2B shows another CIN2 sample of cervical scrape cells prepared in another liquid-based solution that are ICC stained positively using an anti-E6 monoclonal antibody. As shown in FIG. 2B, the CIN2, HSIL abnormal cells was ICC-stained positively to the nucleus and cytoplasm. These cells are in the form of connecting each other with high N/C (nuclear/cytoplasm) ratio (indicated as black arrow) These results demonstrate that HPV E6 protein present in situ can be detected in the abnormal cells from an intermediate stage of neoplasm, in various liquid based solution using the mouse monoclonal anti-HPV E6 described herein.

Figure 3B:
FIG. 3B shows the staining results of another clinical sample, also diagnosed as CIN3, stained with the same anti-HPV E6 mouse monoclonal antibody as the one used in FIG. 3A.
Figure 3D:
FIG. 3D shows another ICC staining results on the same clinical sample as used in Figure and stained with the same anti-HPV E6 mouse monoclonal antibody.
Figure 3A:
FIG. 3A shows the staining results of a clinical sample, diagnosed as CIN3, in a liquid based solution using an anti-HPV E6 mouse monoclonal antibody in an ICC assay according to another embodiment of the invention.
Figure 3C:
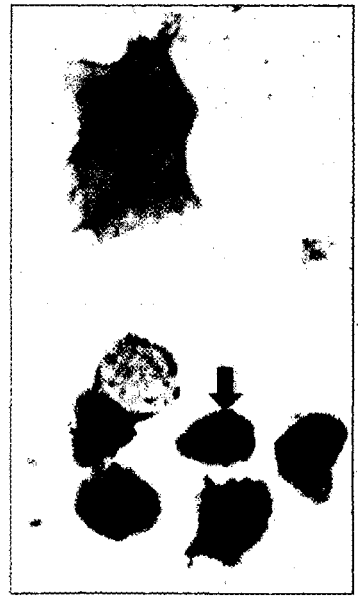
FIG. 3C shows another ICC staining results on the same clinical sample as used in FIG. 3B stained with the same anti-HPV E6 mouse monoclonal antibody.
Figure 3:
FIG. 3E shows another ICC staining results on the same CIN3 sample as used in FIG. 3B but stained with an anti-HPV E7 mouse monoclonal antibody according to another embodiment of the invention.
FIG. 3F shows another ICC staining results of the same CIN3 sample as shown in FIG. 3E stained with the same anti-HPV E7 mouse monoclonal antibody.
FIG. 3G shows the staining results on the same CIN3 sample as shown in FIG. 3B but stained with an anti-p16 mouse monoclonal antibody in an ICC assay.
Figure 3:

To demonstrate the ICC assay described herein can identify intermediate to late stages of cervical intraneoplasm (CIN) cells in liquid-based solution, CIN3 cervical scrape samples in different liquid-based solutions were also prepared to perform the ICC assay described in this invention. FIG. 3A shows certain cervical scrape cells (diagnosed as CIN3 by papanicolaou staining) can be ICC stained positively using an anti-E6 monoclonal antibody. FIG. 3B-3D shows another CIN3 using the same anti-HPV E6 mouse monoclonal antibody. As shown in FIG. 3, the CIN3, HSIL abnormal cells that are in the form of connecting each other with high N/C (nuclear/cytoplasm) ratio (indicated as black arrow) was stained positively to the nucleus and cytoplasm. These results demonstrate that HPV E6 protein can be detected in situ in abnormal cells from an intermediate/late stage of neoplasm, in various liquid-based solution using the mouse monoclonal anti-HPV E6 described herein. These results demonstrate that HPV E6 protein present in situ can be detected in the abnormal cells from CIN3 in liquid-based solution using the mouse monoclonal anti-HPV E6 described herein.

FIG. 3E shows the results of ICC staining with the same CIN3 sample shown in FIG. 3B using an anti-HPV E7 mouse monoclonal antibody. FIG. 3F shows another ICC staining image of the same CIN3 tissue as used in FIG. 3E using the same anti-HPV E7 mouse monoclonal antibody. As shown in the CIN3 lesions of FIGS. 3A-3F, HSIL abnormal cells that are in the form of connecting each other with high N/C (nuclear/cytoplasm) ratio (indicated as black arrow) were stained positively in the nucleus and cytoplasm. These results demonstrate that HPV E7 protein present in situ can be detected in the abnormal cells from an intermediate stage of neoplasm, in various liquid-based solutions using the mouse monoclonal anti-HPV E7 described here. These results demonstrate that HPV E7 protein present in situ can be detected in the abnormal cells from CIN3 in liquid-based solution using the mouse monoclonal anti-HPV E7 described herein.

Figure 3G:
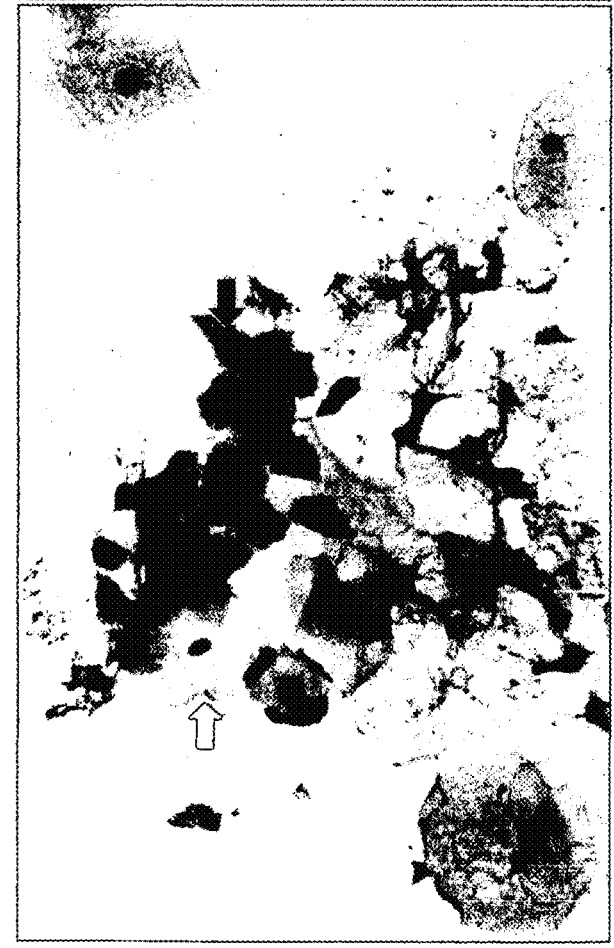

To confirm p16 is also overexpressed in the late stage of neoplasm, the same CIN3 samples were used to do ICC staining using an anti-p16 mouse monoclonal antibody. FIG. 3G shows the results of ICC staining from the same CIN3 sample shown in FIG. 3B-3F using an anti-p16 mouse monoclonal antibody. As Figures shown, the CIN3, HSIL abnormal cells that are in the form of connecting each other with high N/C (nuclear/cytoplasm) ratio (indicated as black arrow) was stained positively to the nucleus and cytoplasm. These results demonstrate that p16 protein present in situ can be detected in abnormal cells from an intermediate to late stage of neoplasm. These results demonstrate that HPV E6, HPV E7, and p16 protein present in situ can be detected in the abnormal cells from CIN3 in liquid-based solution using the mouse monoclonal antibodies described herein.

Figure 4:
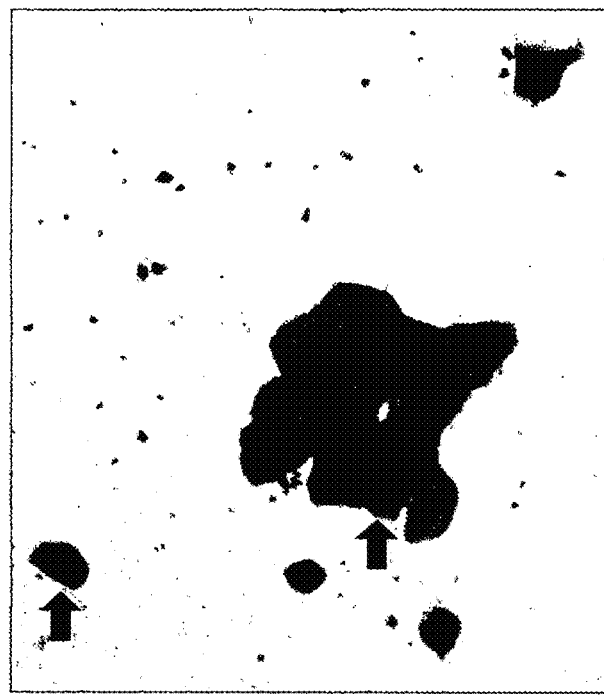
FIG. 4 shows the staining results of a clinical sample diagnosed as adenocarcinoma stained with an anti-HPV E6 mouse monoclonal antibody in an ICC assay according to another embodiment of the invention.

As another example to demonstrate the ICC assay described herein can be applied to detect cervical cancer cells in liquid-based solution, different carcinoma of cervical scrape samples in different liquid-based solutions were also prepared to perform the ICC assay described in this invention. FIG. 4 shows cervical cancer cells (diagnosed as adenocarcinoma by papanicolaou staining) can be ICC-stained positively using an anti-E6 monoclonal antibody. In FIG. 4, the abnormal cell with high N/C (nuclear/cytoplasm) ratio (indicated by black arrow) was stained positively. HSIL abnormal cells that are in the form of connecting each other were also stained positively. These results demonstrate that HPV E6 protein present in situ can be detected in adenocarcinoma cervical cells in liquid-based solution using the mouse monoclonal anti-HPV E6 described herein.

To demonstrate the ICC assay described herein can also be applied to detect another type of cervical cancer cells in liquid-based solution, FIG. 5A shows another type of cervical cancer cells, SCC (diagnosed as squamous cell carcinoma by papanicolaou staining), that are ICC-stained positively using an anti-E6 monoclonal antibody. FIG. 5B shows the results of ICC staining of the same SCC sample using an anti-HPV E7 mouse monoclonal antibody. FIG. 5C shows the results of ICC staining of the same SCC sample using an anti-p16 mouse monoclonal antibody. As the figures show, the HSIL SCC cells were stained positively to the nucleus and cytoplasm. These results demonstrate that HPV E6 and HPV E7 protein present in situ can be detected from various types of cervical cancer cells in liquid-based solution using the mouse monoclonal anti-HPV E6 or anti-HPV E7 antibodies described. To confirm p16 is also overexpressed in the late stage of neoplasm, the same SCC sample was used to do ICC staining using an anti-p16 mouse monoclonal antibody. FIG. 5C shows the results of ICC staining of the same SCC sample shown in FIG. 5A-5B using an anti-p16 mouse monoclonal antibody, indicating that p16 protein present in situ can be detected in the late stage of neoplasm. These results demonstrate that HPV E6, HPV E7, and p16 protein can be detected in situ in the abnormal cells from different types of cervical cancers in liquid-based solution using the mouse monoclonal antibodies described herein.

To confirm the ICC staining results described herein arises from the specific binding of the HPV antibody with the HPV proteins present in situ of the cervical scrape cells, normal cervical cells from liquid-based solution were also obtained to test on the ICC assay. FIG. 6A shows all cervical scrape cells (diagnosed as normal by papanicolaou staining) prepared in liquid-based solutions that are stained negatively by ICC using an anti-E6 monoclonal antibody. The same samples were also stained by ICC using an anti-HPV E7 monoclonal antibody as shown in FIG. 6B. These results demonstrate that neither HPV E6 protein, nor HPV E7 protein is present in situ from the normal cervical scrape cells, thus the ICC assay shows negative staining results using the mouse monoclonal anti-HPV E6 or the mouse monoclonal anti-HPV E7 antibody. Therefore, the results indicate that the ICC assay described in this invention is a specific staining method for detection of HPV proteins using the HPV specific antibodies described herein.

In addition, pap smear normal samples were also tested by ICC and stained negatively (32 out of 32) using anti-HPV antibody. Among the 32 samples, 12 samples were stained with anti-HPV E6 antibody, 16 samples were stained with anti HPV E7 antibody, and 4 samples were stained with anti-HPV L1 antibody. These data indicate that the ICC staining assay described in this invention is very specific. Compared to HPV DNA test results on the same samples, 19% (6 out of 32) of the pap smear normal samples are positive on HPV DNA test. The high-grade HPV DNA test used in this study was hc2, the only FDA approved HPV DNA test. For those HPV DNA positive but pap smear normal and HPV ICC negative samples, it is possible the HPV DNA assay is false positive, or there is DNA from the HPV infection but no expression of HPV oncogenic proteins. Therefore, the HPV ICC assay described herein has a greater clinical relevance for screening of cervical cancer compared to the HPV DNA test.

To demonstrate the ICC staining at the cellular level, FIG. 7A shows cytoplasmic staining of cervical scrape cells from liquid-based solution using a mouse monoclonal anti-HPV-E6 antibody. FIG. 7B shows nuclear staining of the same sample from FIG. 7A staining by a mouse monoclonal anti-HPV-E7. FIG. 7C shows representative images of cytoplasmic staining from another sample using a mouse monoclonal anti-HPV-E7 antibody. As shown in the figures, the abnormal cell with high N/C (nuclear/cytoplasm) ratio (indicated by black arrow) was stained positively while the normal cells (big, irregular cell shape with small nucleus) stain negatively as indicated by the white arrow. These results indicate that HPV E6 and HPV E7 proteins can be detected in cytoplasm and/or nuclear using the mouse monoclonal anti-HPV E6 and the mouse monoclonal anti-HPV E7 antibody described herein.

To demonstrate HPV E6 E7 oncoproteins can be expressed in certain LSIL (Low grade of Squamous Intraepithelial Lesion) or CIN 1 (Cervical Intraepithelial Neoplasia, mild cell abnormalities), FIG. 8A-8C shows the results of ICC staining of a clinical sample diagnosed as CIN1 in a liquid-based solution using an anti-HPV E6 mouse monoclonal antibody. FIG. 8B-8C shows another image of the same ICC staining results shown in FIG. 8A using the same anti-HPV E6 mouse monoclonal antibody. FIG. 8D shows the results of ICC staining from the same CIN1 sample shown in FIG. 8A using an anti-HPV E7 mouse monoclonal antibody. FIG. 8E shows another image of the same ICC staining results shown in FIG. 8D using the same anti-HPV E7 mouse monoclonal antibody. As Figures shown, the abnormal, LSIL, CIN1 cells that are in the form of connecting each other or with high N/C (nuclear/cytoplasm) ratio (indicated by the black arrow) was stained positively to the nucleus and cytoplasm. These results demonstrate that HPV E6 and HPV E7 protein present in situ can be detected in the early stage of neoplasia in liquid-based solution using the mouse monoclonal anti-HPV E6 or anti-HPV E7 antibodies described herein. To confirm if p16 is expressed in the early stage of neoplasia, the same CIN1 sample was used to do ICC staining using an anti-p16 mouse monoclonal antibody. FIG. 8F shows the results of ICC staining from the same CIN1 sample shown in FIG. 8A-8E using an anti-p16 mouse monoclonal antibody, indicating that p16 protein cannot be detected in the early neoplasia of this CIN1 sample. These results demonstrate that HPV E6, HPV E7 proteins present in situ can be detected in the abnormal cells from early stage of neoplasia using the mouse anti-HPV E6, or anti-HPV E7 monoclonal antibodies described in this invention, but p16 is not detectable by the anti-p16 mouse monoclonal antibody using the ICC assay described herein.

An immunocytochemical (ICC) assay not only detects HPV infection, but also detects HPV oncogenic proteins in situ. Therefore, ICC assay alone, or in combination with various specific and common anti-HPV antibodies can be a powerful tool for HPV detection in situ, as compared to a standard HPV DNA test or pap smear assay.

TABLE 1

ICC staining results using a mouse anti-HPVE6 monoclonal antibody on various cervical scrape samples in a liquid-based solution.

| Pap smear | normal | ASCUS | ASC-H | CIN1 | CIN2/3 | SCC |
|---|---|---|---|---|---|---|
| ICC positive, using an anti-HPV E6 antibody | 4 | 3 | 4 | 11 | 17 | 4 |
| ICC negative, using an anti-HPV E6 antibody | 25 | 6 | 4 | 6 | 0 | 1 |
| total | 29 | 9 | 8 | 17 | 17 | 5 |
| positive rate | 14% | 33% | 38% | 65% | 100% | 80% |

Table 1 shows the results of an ICC assay using a mouse anti-HPVE6 monoclonal antibody on various cervical scrape samples in a liquid-based solution. The results in Table 1 demonstrate that HPV E6 protein can be detected in situ in single cells fixed on a slide by immunocytochemical (ICC) assay using a mouse monoclonal anti-HPV E6 antibody. The in situ presence of HPV E6 proteins can be detected in various stages of cervical scrape samples in various liquid-based solutions. The same cervical scrape samples were also processed by standard papinouli staining to compare the ICC staining results with the pap smear results. As shown in Table 1, HPV E6 proteins are present in the cervical scrape normal, ASCUS, ASC-H, CIN1, CIN2/3 samples with increasing positivity rate, respectively.

There is about 100% positive rate for samples diagnosed with pap smear CIN2/3, while only 14% of samples diagnosed with pap smear normal stained positively by ICC using the same anti-HPVE6 antibody. For ASCUS or ASC-H samples, about 33% to 50% of these samples are stained positively by the same anti-HPV E6 antibody as used for the CIN1, CIN2/3 samples shown in Table 1, indicating expression of oncogenic proteins in these ASCUS or ASC-H sample subjects to be followed up for further cancer progression. For samples with pap smear diagnosed as ASCUS and ICC staining (anti-HPV E6) as negative, it may have less risk to develop progressive lesion.

TABLE 2

Summary of the ICC staining results using a mouse monoclonal anti-HPVE6 antibody on CIN2+ cervical scrape samples in a liquid based solution.

| Pap smear | normal | CIN2+ | | |
|---|---|---|---|---|
| ICC positive, using an anti-HPV E6 antibody | 4 | 21 | 84% | PPV |

TABLE 2-continued

Summary of the ICC staining results using a mouse monoclonal anti-HPVE6 antibody on CIN2+ cervical scrape samples in a liquid based solution.

| Pap smear | normal | CIN2+ | | |
|---|---|---|---|---|
| ICC negative, using an anti-HPV E6 antibody | 25 | 1 | 96% | NPV |
| Sensitivity | | 95% | | |
| specificity | 86% | | | |

Table 2 shows summary of the ICC staining results from Table 1. The ICC staining method using the anti-HPV E6 antibody described in this invention provides ICC assay sensitivity of 95% for CIN2+ with specificity of 83%. This data suggests this assay can be useful to detect HPV proteins for screening of cervical cancer from the general population along with routine pap smear staining.

TABLE 3

ICC staining results using a mouse monoclonal anti-HPVE7 antibody on various cervical scrape samples in a liquid-based solution.

| Pap smear | normal | ASCUS | ASC-H | CIN1 | CIN2/3 | SCC |
|---|---|---|---|---|---|---|
| ICC positive, using an anti-HPV E7 antibody | 3 | 4 | 3 | 11 | 16 | 4 |
| ICC negative, using an anti-HPV E7 antibody | 25 | 6 | 5 | 6 | 1 | 1 |
| total | 28 | 10 | 8 | 17 | 17 | 5 |
| positive rate | 11% | 40% | 38% | 65% | 94% | 80% |

As another example of the HPV detecting ICC assay, Table 3 and Table 4 show results of ICC staining using anti-HPV E7 antibody. HPV anti-E7 gives comparable ICC results as what is shown for HPV anti-E6. HPV E7 proteins are present in the cervical scrape normal, ASCUS, ASC-H, CIN1, CIN2/3 samples with increasing positivity rate, respectively. There is about 94% positive rate for samples diagnosed with pap smear CIN2/3, while only 11% of samples diagnosed with pap smear normal stained positively by ICC using the same anti-HPVE7 antibody. For ASCUS or ASC-H samples, about 40% of these samples are stained positively by the same anti-HPV E7 antibody as used for the CIN1, CIN2/3 samples shown in Table 3, indicating expression of oncogenic proteins in these ASCUS or ASC-H sample subjects to be followed up for further cancer progression. For samples with pap smear diagnosed as ASCUS and ICC staining (anti-HPV E7) as negative, there may be a lower risk to develop a progressive lesion.

Table 4 shows summary of the ICC staining results from Table 3. The ICC staining method using the anti-HPV E7 antibody described in this invention provides ICC assay sensitivity of 91% for CIN2+ with specificity of 89%. This data suggests this assay can be useful to detect HPV proteins for screening of cervical cancer from the general population along with routine pap smear staining.

TABLE 4

Summary of the ICC staining results using a mouse monoclonal anti-HPVE7 antibody on CIN2+ cervical scrape samples in a liquid based solution.

| Pap Smear | Normal | CIN2+ | | |
|---|---|---|---|---|
| ICC positive, using an anti-HPV E7 antibody | 3 | 20 | 87% | PPV |
| ICC positive, using an anti-HPV E7 antibody | 25 | 2 | 93% | NPV |
| Sensitivity | | 91% | | |
| specificity | 89% | | | |

TABLE 5

ICC staining results for pap smear normal samples using various anti-HPV antibodies compared to HPV DNA test

| | Pap smear normal | |
|---|---|---|
| | ICC HPV positive | ICC HPV negative |
| high-grade HPV DNA positive | 0 | 6 |
| high-grade HPV DNA negative | 0 | 26 |

To test if the HPV ICC assay described in this invention is suitable for early stage of cervical cancer screening, pap smear normal samples are used to compare the HPV ICC assay with HPV DNA test. All pap smear normal samples tested (32 out of 32) stained negatively using anti-HPV antibody. Among the 32 samples, 12 samples were stained with anti-HPV E6 antibody, 16 samples were stained with anti HPV E7 antibody, and 4 samples were stained with anti-HPV L1 antibody. These data indicate that the ICC staining assay described in this invention is very specific. Comparing to HPV DNA test results on the same samples, 19% (6 out of 32) of the pap smear normal samples are positive on HPV DNA test. The high-grade HPV DNA test used in this study was hc2, the only FDA approved HPV DNA test. For those HPV DNA positive but pap smear normal and HPV ICC negative samples, it is possible the HPV DNA assay is false positive, or there is DNA detection from the HPV infection but no expression of HPV oncogenic proteins. These data indicate that the HPV ICC assay described herein provides better positive predictive value compared to HPV DNA test. Thus, the HPV ICC assay has a greater clinical relevance for screening of cervical cancer.

5. HPV Flow Cytometry Assay

As another example of an immunoassay for the detection of HPV proteins, a HPV flow cytometry assay is performed. Cells from cervical scrapes collected in liquid-based solution following the manufacturer's guideline were centrifuged, washed, and immunostained following a similar ICC staining procedure. Instead of applying cells onto a slide, the cells were kept in solution from staining through analysis by flow cytometry. To perform HPV flow assays, the cervical cells in solution were fixed, blocked and incubated with anti-HPV antibodies followed by the appropriate secondary antibody and substrate agents used for detection by flow cytometry. The advantage of this HPV flow cytometry assay is that it is high throughput with no requirement for a highly trained cytologist to view the slides.

In one embodiment, a kit for performing an ICC flow cytometry assay is provided. The kit may include a pre-antibody blocking solution, post-antibody blocking solution, an anti-HPV antibody as the primary antibody, an anti-mouse or anti-rabbit immunoglobulins conjugated with flourecent or biotin, or other agents as secondary antibody, a solution containing appropriate agents used as substrate for the secondary antibody to be detected by flow cytometry.

As an example, indirect labelling requires two incubation steps, the first with a primary antibody followed by a compatible secondary antibody. The secondary antibodies are conjugated with a fluorescent dye (FITC, PE, Cy5, etc.). The anti-HPV antibodies may also be directly tagged with fluorescent, or biotin, or other agents to be detected following appropriate agents used as substrate. The pre-antibody blocking solution may contain certain proteins or BSA, or serum or other agents to block the cells from nonspecific binding of antibody. The post-blocking solution may contain a similar solution as the pre-antibody blocking solution with less proteins or serum to be used along with primary antibody incubation. The solution containing HPV antibodies may be in concentrated form, or may be in diluted form as a ready to use reagent. The solution containing secondary antibodies may be in concentrated form, or may be in diluted form as a ready to use reagent.

As an example, the HPV E6, E7, or L1 protein can be detected by the specific antibody followed by the $2^{nd}$ antibody labeled with fluorescent dye (FITC, PE, Cy5, etc.). The cells analyzed by flow cytometry can be gated by size or other parameters to look at the cell population with or without staining. The stain intensity from cell population with smaller cell size can be compared to the cell population with bigger cell size as a control of normal cells in the assay. This assay provides specific staining for individual cells. The number of cells stained or unstained can be counted, and the intensity of staining can also be quantitated by analysis. This assay can be high throughput, requires no microscope, nor cytologist to score the staining results. The powerful computer software from the flow cytometry provides all data for analysis with no bias or trained personnel in cytology required. This assay should apply well in the clinical setting as screening test or as a companion test for the detection of HPV associated proteins.

As another example, after the cells are stained, it is better to store the cell suspension immediately at 4° C. in the dark and analyze the cells on the flow cytometer as soon as possible. If there is a period of longer than an hour before flow analysis, it is necessary to fix the cells. This can preserve them for at least several days. This will stabilize the light scatter and inactivate most biohazardous agents. The fixation for different antigens will require optimization for different assays. Format 1. Paraformaldehyde 0.01% to 1% for 10-15 minutes only, 100 µl per sample. Format 2: Acetone or methanol: Add 1 ml ice cold acetone to each sample. Mix gently. Place at −20° C. for 5 to 10 minutes. Centrifuge, wash twice in PBS 1% BSA For intracellular staining, cells can be fixed first to ensure stability of soluble antigens or antigens with a short half life. This should retain the target protein in the original cellular location. Detection of intracellular antigens requires a cell permeabilization step prior to staining. Antibodies should be prepared in permeabilization buffer to ensure the cells remain permeable. When gating on cell populations, the light-scatter profiles of the cells on the flow cytometer will change considerably after permeabilization. Antigens in cytomplasmic organelles and granules will require a fixation and permeabilization method depending on the antigen. The epitope needs to remain accessible.

Fixation could be critical for the quality of staining assay. There are several methods available for fixation: (1) Formaldehyde followed by detergent: Fixation in 0.01% formaldehyde for 10-15 minutes (this will stabilize proteins), followed by disruption of membrane by detergent. Detergents: Triton or NP-40 (0.1 to 1% in PBS). These will also partially dissolve the nuclear membrane and are therefore very suitable for nuclear antigen staining. It should be noted that loss of cell membrane and cytoplasm will result in decreased light scattering and also in reduced non-specific fluorescence. Tween 20, Saponin, Digitonin and Leucoperm are mild membrane solubilizers. Use at 0.5% in PBS. These give large enough pores for antibodies to go through without dissolving the plasma membrane. Suitable for antigens in the cytoplasm or the cytoplasmic face of the plasma membrane. Also suitable for soluble nuclear antigens. (2) Formaldehyde (0.01%) followed by methanol. Methanol followed by detergent. Add 1 ml ice cold methanol to each sample. Mix gently. Place at −20° C. for 10 minutes. Centrifuge, wash twice in PBS 1% BSA. Acetone fixation and permeabilization: Add 1 ml ice cold acetone to each sample. Mix gently. Place at −20° C. for 5 to 10 minutes. Centrifuge, wash twice in PBS 1% BSA The one or more immunological assays using antibodies and purified recombinant proteins derived from HPV early and/or late genes as obtained herein serve as reliable indicators of whether HPV infection has occurred. In addition, HPV associated malignancy or pre-malignant cell transformation can be assayed. One of the most useful aspects of the invention is in diagnosing cervical carcinoma, both squamous cell carcinoma and adenocarcinoma as well as any epithelial cell abnormality associated with oncogenic HPV infection including koilocytosis; hyperkerotosis; precancerous conditions encompassing intraepithelial neoplasias or intraepithelial lesion; high-grade dysplasias; and invasive or malignant cancers.

In one embodiment, the early gene that can be used herein may include papillomavirus E6 genes, papillomavirus E7 genes, among others. In another embodiment, the late gene that can be used herein may include papillomavirus L1 genes, papillomavirus L2 genes, among others.

One aspect of the invention provides recombinant proteins, such as a recombinant hybrid protein containing a full length sequence of HPV oncogenic proteins, e.g., full-length E6, E7, and/or L1 polypeptide sequence, which have been found very difficult to obtain and purify due to undesirable aggregation during protein purification, protein instability, low levels of expression, and low immunogenic responses of purified proteins. For example, many early E6 oncoproteins contain many cysteine amino acids and thus the correct topography of the E6 oncoproteins requires the formation of many disulfide bonds properly. In addition, it was known that certain immunological assays using small peptides of early E6 and E7 proteins result in extremely low assay specificity and sensitivity and thus are unsuitable to commercialize for in vitro diagnostics.

In high grade CIN lesions, E6 and E7 are strongly expressed in host basal epithelial cells and interfere substantially with cell cycle control of these replication competent host cells. Expression of HPV oncoproteins interfers with G1-S-Phase regulation in host cells. The HPV E6 and E7 proteins target a plethora of cellular interactions, such as the inactivation of pRB by E7 and the degradation of p53 by E6. High levels of HPV E7 proteins inactivate pRB and leads to disruption of E2F-Rb binding. Usually binding of pRB to E2F blocks E2F driven cell cycle activation. In replicating cells, E2F is regulated by phosphorylation of RB. Rb phosphorylation is normally mediated by cyclin dependent kinases (CDK4, CDK6) that are controlled by several kinase inhibitors (INKs).

As a result of the loss of Rb/E2F repression and the strong activation by free E2F, the expression of a host cell protein, p16INK4a, is strongly overexpressed. In addition, S-phase genes are continuously activated since the p16INK4a mediated repression of Cdk4/6 has no downstream effect on pRb host cell protein. Since E7-dependent E2F release is not mediated by phosphorylation of pRb, the counter-regulatory p16INK4a expression has no effect on the activated cell cycle. Under physiological conditions p16INK4a is expressed when cells undergo a genomic stress situation such as substantial shortening of telomeres in ageing tissues. Also, apoptosis is abrogated by HPV E6 mediated degradation of p53. The overexpression of the cyclin dependent kinase (CDK) inhibitor, p16INK4a, is a direct consequence of deregulated HPV oncogene expression.

In addition, host cell proteins important for proliferation and host cell genome replication may be overexpressed as a result of HPV infection. These host cell proteins include, ki67 (MIB-1), MYC cellular oncogene, Cyclin proteins (e.g., cyclin A, B, E, etc.), CDKN2A/p16INK4a, telomerase (e.g., TERC), replication complex proteins (e.g., MCM5, CDC6, topoisomerase II alpha (TOP2A), MCM2, minchromosome maintenance proteins 2, 4, and 5, etc.).

As an example, the immunological assays for detection of HPV proteins, such as E6, E7, L1, etc., or immune response thereof due to HPV infection can be performed in high throughput ELISA screening assays, rapid immunological screening assays, and additional multiplexed protein chip assays, and combinations thereof. Embodiments of the invention provides various polyclonal and monoclonal antibodies for HPV proteins to be used in one or more assays, including an antibody, antigen, or immunocomplex assays developed to detect HPV viral proteins encoded by early genes (e.g., E6 and E7) and late genes (e.g., L1). In addition, the developed antibody, antigen, or immunocomplex assays for E6, E7, L1, protein or their antibodies thereof in one format, for example, a microplate format, can be adapted into a one-step immunochromatographic assay for the direct measurement of E6, E7, L1 proteins or antibodies induced by HPV infection. The one or more immunological assays as provided herein aims to employ user friendly procedures with simple instrumentation or no additional instrumentation and to be performed in a short period of time. Comparison of the results of the various immunological assays and nucleic acid hybridization assays with cytological and histological data for the human subjects as well as demographic information serve to validate the correlation and accuracy in diagnosing HPV infection and/or cervical cancer.

Another example of a method of screening a human subject infected with a human papillomavirus may include obtaining a clinical sample from the human subject, conducting a nucleic acid hybridization assay on the clinical sample, detecting the presence of a papillomavirus genome in the clinical sample from the human subject, conducting one or more immunological assays on the clinical sample, detecting the presence of an antibody to an early papillomavirus viral protein or the presence of the early papillomavirus viral protein in the clinical sample using a first recombinant protein of the early papillomavirus viral protein, and detecting the presence of an antibody to a late papillomavirus viral protein or the presence of the papillomavirus late viral protein in the clinical sample using a second recombinant protein of the late papillomavirus viral protein.

The one or more diagnostic immunological assays as described therein may also include obtaining polyclonal antibodies, monoclonal antibodies, and/or antiserum specific against the one or more recombinant proteins as obtained and described herein, taking a clinical sample likely to contain HPV associated proteins and/or antigens, reacting it with the obtained polyclonal antibodies, monoclonal antibodies, and/or antiserum specific for the one or more recombinant proteins, and assaying for the presence of any antibody-antigen complexes by suitable detection systems. Suitable detection system may employ various colormetric, chemiluminescent, flourescent substrates, etc., specific for a secondary antibody used in each immunological assay.

Early diagnosis of HPV infection is important for successful prevention and treatment of cervical cancer. Strategies to prevent cervical cancer require improved HPV testing/screening to cover a broad range of the world population in addition to follow-ups with those subjects with past or present HPV infection and/or pre-cancerous lesions. It is known that HPV infections must be present in women for 12-15 years before invasive cancer develops. It is thus important to be able to assay biomarkers for HPV infection as described herein to pre-screen women early, such that it will be possible to treat HPV infection early and prevent cervical cancer development, rather than having to rely on chemotherapy or radiation to treat cancer malignancy.

The cell culture containing various recombinant papillomavirus proteins in various expression vectors as described herein were then scaled up to 1 liter or 10 liter, or 100 liters or higher to obtain high quantity of soluable recombinant protein for purification. The soluble fraction was passed through various chromatography columns with appropriate system to bind to the tag expressed along with the HPV recombinant proteins. The tag-HPV recombinant proteins were then eluted from the column and concentrated down to 100 ml or 10 ml to 1 ml. The purified soluble recombinant HPV proteins were further concentrated and dialyzed with buffers at neutral pH or PBS buffers to be used as immunogen to generate antiserum against the HPV proteins. The soluble recombinant HPV proteins were thus purified from soluble fractions and folded close to their native folding states as in vivo natural conditions.

One or more immunological assays can be used to test the specificity of the monoclonal antibodies generated by screening the hybridoma cell lines with two or more HPV recombinant proteins. EIA (Enzyme Immuno Assay) and/or Western blots were used as the assay format to test the specificity of the HPV antibodies described herein. Various purified recombinant HPV proteins, including the original screening proteins used for obtaining the anti-HPV antibodies and other proteins not used for screening, were used to coat on the microtiter plate to test the specificity of the obtained anti-HPV antibodies on EIA. Proteins in cell lysate from cervical cancer cell lines (with or without HPV infection) were also used to test the specificity of the anti-HPV antibodies by western blot. To confirm the binding and reactivity of the HPV antibodies with proteins from HPV infected cell lines, western blot is very useful to demonstrate specific protein bands corresponding to the proteins present in the HPV-infected cell lines. The protein bands from Western blots were compared to recombinant HPV proteins at their expected molecular weight positions on SDS-PAGE gels. Cell lysate from cervical cancer cell lines, including Hela cell line (HPV18 positive), SiHa cell line (HPV16 positive) and C33A cell line (non-HPV infected) were used to demonstrate detection of HPV E6, E7, or L1 by the HPV monoclonal antibody on western blot.

To demonstrate a monoclonal antibody capable of binding to two or more HPV viral proteins from different HPV types as described in this invention, a monoclonal antibody capable of reacting with recombinant E6 proteins of HPV 16 and HPV18 was also the obtained. FIG. 9 shows the specificity of a monoclonal antibody that recognizes the common epitode and is capable of binding to recombinant HPV16 E6 and HPV18E6 proteins on EIA. The recombinant protein coated on microtiter plate to be detected by the antibody described herein is in its native form. These data demonstrate that the monoclonal antibody reacts strongly to the native form of recombinant HPV16 E6 and HPV18E6 proteins, but does not react with the native form of either recombinant HPV E7 or recombinant HPV L1 proteins. These data indicate that this antibody recognizes an HPV E6 common epitope and is capable of binding to the native form of recombinant HPV16 E6, and HPV18 E6 proteins.

As another example to demonstrate a monoclonal antibody capable of binding to two or more HPV viral proteins from different HPV types as described in this invention, FIG. 10 shows the specificity of a monoclonal antibody capable of reacting with both recombinant HPV16 E7 and HPV18E7 protein on EIA. The recombinant protein coated on microtiter plate detected by the antibody described herein is in its native form. These data demonstrate the monoclonal antibody described herein reacts strongly to native form of recombinant HPV16 E7 and HPV18 E7 proteins, but nonreactive to native form of recombinant HPV E6 nor HPV L1 proteins. These data indicate that this antibody recognizes an HPV E7 common epitope and is capable of binding to the native form of HPV16 E7 and HPV18 E7 proteins.

FIG. 11A shows the representative image of the dysplasia cells of CIN2 tissues stained by immunohistocytostaining (IHC) using an anti-E6 molonolal antibody. FIG. 11B shows the representative image of the adjacent normal epithelium from the dysplasia tissue of the CIN2 sample of FIG. 11A. FIG. 11C-11D shows the representative image of the dysplasia epithelium of two CIN3 samples stained by IHC using the same anti-E6 monolonal antibody. These data suggest the IHC staining by E6 monoclonal antibody is specific in the nuclear and cytoplasm of dysplasia cells.

As an another example, FIGS. 12A-12D show IHC staining of squamous cell carcinoma demonstrated by mouse monoclonal HPV E7 antibody. Results indicate expression of E7 oncoprotein can be detected in the tumor cells of SCC tissue. Solid Black arrows indicate the specific staining of E7 protein in dysplasia cells, while empty clear arrows indicate the normal cells with no stain. Highly magnified images indicate localization of the E7 proteins expressed in the cytoplasm of tumor cells, but not in the normal epithelium, or stroma cells. These data suggest the IHC staining by E7 monoclonal antibody is specific in the cytoplasm of tumor cells. FIG. 12A shows the representative image of the squamocarcinoma (SCC) tissue from tissue microarray stained by IHC using an anti-E7 monoclonal antibody. FIG. 12B shows the representative image of the normal epithelium (15 mm away from the tumor tissue) of the SCC subject from FIG. 12A. FIG. 12C shows the representative image of another SCC sample from tissue microarray stained by IHC using the same anti-E7 monoclonal antibody. FIG. 12D shows the magnified representative image of the tumor cells stained in cytoplasm from FIG. 12C.

4). The Reactivity of the Purified Anti-HPV Antibodies with HPV Proteins In Situ by Immunocytochemistry (ICC)

Cervical scrapes collected by Liquid based solution were processed according to the manufacture instruction. The cell preparation was divided into two parts, one for conventional pap smear, the other one for immunostaining. Monolayer of cervical cells on slide was processed by cytospin or thin prep techniques. The cells were then fixed and stained followed by immunostaining protocol. Stained cells are visualized under microscope.

As an example, FIG. 13A-13C demonstrate immunocytochemistry assay using anti-HPV antibody. FIG. 13A shows the representative image of cervical cells from a CIN2 cervical scrape sample prepared by thin prep and stained by ICC using a mouse monoclonal anti-HPV E7 antibody. FIG. 13B shows the representative image of cervical cells from a CIN3 cervical scrape sample prepared by thin prep and stained by ICC using a mouse monoclonal anti-E6 antibody. FIG. 13C shows the representative image of cervical cells from an adenocarcinoma (ADC) cervical scrape sample prepared by thin prep and stained by ICC using the same anti-E6 antibody shown in FIG. 13B.

anti-HPV antibodies, IHC score from cytoplasm staining of tumor cells using other anti-HPV antibodies is also shown in Table 6. Results of HPV DNA typing is also shown on the table for its corresponding case.

As shown in Table 6, both nucleus and cytoplasmic staining are found in all the subjects of tumor cells from SCC and ADE stained by the anti-E7 antibody. However, there is more staining (percentage stained) found in the cytoplasm of tumor cells compared to the staining of nuclear of tumor cells. The detection of HPV E7 protein in its adjacent normal epithelium cells was only found in the nucleus, but not found in the cytoplasm of the epithelial cells. The staining of cytoplasm appears most distinguishable in tumor cells compared to its corresponding normal adjacent cells. These data demonstrate expression of HPV E7 proteins was detected in the cytoplasm and nuclear of tumor cells of SCC and ADE tissues. The localization of the E7 proteins expressed in the cytoplasm of tumor cells, but not in the normal epithelium or stroma cells, appears to be tumor specific. HPV E7 proteins present in the nucleus of normal adjacent epithelium and tumor cells detected by the anti-HPV E7 antibody indicate HPV infection with oncoprotein expression. A similar staining pattern was also found when other anti-HPV antibodies were used as shown in

TABLE 6

IHC staining results (stained %) and HPV DNA typing for 12 SCC biopsy samples and 12 ADC biopsy samples (C: Cytoplasmic; N: Nucleus; Dys: dysplasia or tumor cells).

| | | Anti-E7 | | | | Anti-E6 | Another anti-E6 | Anti-L1 |
|---|---|---|---|---|---|---|---|---|
| | | Dys (% stained) | | Normal epith. (% stained) | | Another anti-E7 Dys (%) | Dys (%) | Dys. (%) | Dys. (%) |
| Sample # | HPV type | C | N | C | N | C | C | C | C |
| SCC-1 | 18 | 85 | 85 | 0 | 20 | 12.5 | 10 | 70 | 55 |
| SCC-2 | 16, 52 | 90 | 85 | 0 | 25 | 15 | 15 | 10 | 55 |
| SCC-3 | 16 | 60 | 65 | 0 | 40 | 5 | 0 | 10 | 20 |
| SCC-4 | 16 | 92 | 50 | 0 | 40 | 5 | 0 | 10 | 85 |
| SCC-5 | 16, 52, 58 | 92 | 55 | 0 | 50 | 20 | 5 | 15 | 88 |
| SCC-6 | 18, 52, 58 | 90 | 60 | | | 25 | 18 | 10 | 70 |
| SCC-7 | 16, 52 | 92 | 75 | 0 | 30 | 30 | 5 | 10 | 20 |
| SCC-8 | 16, 58 | 10 | 10 | 0 | 5 | 0 | 0 | 10 | 50 |
| SCC-9 | no DNA | 95 | 60 | 0 | 40 | 25 | 8 | 15 | 8 |
| SCC-10 | 18 | 92 | 65 | 0 | 60 | 45 | 25 | 20 | 65 |
| SCC-11 | 16, 58 | | | 0 | 80 | 5 | | 0 | 0 |
| SCC-12 | 33 | 95 | 90 | 0 | 0 | 30 | 1 | 20 | 55 |
| ADE-1 | 16, 18 | 30 | 20 | 0 | 50 | 15 | 25 | 20 | 82 |
| ADE-2 | no DNA | 62 | 40 | 0 | 30 | 35 | 70 | 35 | 78 |
| ADE-3 | 16 | 20 | 30 | 0 | 20 | 35 | 55 | | 60 |
| ADE-4 | 16, 18 | 80 | 80 | 0 | 0 | 10 | 5 | 0 | 90 |
| ADE-5 | 51, 52 | 95 | 80 | 0 | 50 | 10 | 70 | 15 | 92 |
| ADE-6 | 11, 16, 52 | | | 0 | 40 | 5 | 0 | 0 | 15 |
| ADE-7 | 18 | 50 | 40 | 0 | 60 | 25 | 20 | 20 | 75 |
| ADE-8 | 18 | 85 | 60 | 0 | 40 | 15 | 50 | 15 | 82 |
| ADE-9 | 45 | 82 | 55 | 0 | 30 | 30 | 2 | 20 | 40 |
| ADE-10 | 18 | 15 | 10 | 0 | 40 | 15 | 15 | 5 | 70 |
| ADE-11 | 18, 59 | 70 | 0 | 0 | 50 | 15 | 8 | 5 | 65 |
| ADE-12 | 18 | | | | | | | | 30 |

To analyze the HPV IHC results from each subject of invasive cancer, Table 6 shows data from 24 cases of invasive cancer samples with IHC score for staining of cytoplasm (C), and nucleus (N) using C, or N followed by the % of staining using the anti-HPV E7 antibody. Additional anti-HPV antibodies including another anti-E7 antibody, Anti-HPV E6 antibody like MAb1 and MAb 7 and anti-HPV L1 antibody were also tested on the same tissue microarray. To demonstrate the IHC staining by various anti-HPV antibodies, IHC score from cytoplasm staining of tumor cells using other anti-HPV antibodies is also shown in Table 6. Data indicate that the HPV IHC assay as described herein can detect HPV early gene such as E6, E7, and late gene such as L1 proteins present in the tumor cells of cervical cancer tissues.

Comparing the results of HPV IHC to the HPV DNA typing, the anti-E7 antibody reacts positively with all the HPV types present in the samples tested. For example, the anti-E7 monoclonal antibody as described herein can detect single HPV infection by at least HPV-16, HPV-18, HPV-33, HPV-45, etc, which are cancer-related HPV types (high risk HPV types). The single anti-E7 monoclonal antibody can also detect HPV infection by two or more HPV types, such as the combination of HPV 11, HPV-16, HPV-18, HPV-52, HPV-58, HPV-51, HPV-59, etc., which include high risk, low risk, and non-oncogenic α-papillomaviruses. However, infection by multiple HPV types contains at least one type that is a high-risk HPV type. These data indicate that the anti-E7 antibody described in this invention is non-type specific, and thus provides a powerful tool to detect HPV E7 proteins from most common high-risk HPV types in the cervical cancer.

To analyze the HPV IHC results from each subject of CIN3, Table 7 shows data from 30 cases of CIN 3 samples with IHC score for staining of cell membrane (M), cytoplasm (C), and nucleus (N) using M, C, or N followed by the of staining with the anti-E7 antibody. Additional anti-HPV antibodies including Anti-HPV E6 antibody like MAb1 and MAb 7 and anti-HPV L1 antibody were also tested on the same tissue microarray. To demonstrate the IHC staining by various anti-HPV antibodies, IHC score from cytoplasm staining of tumor cells using other anti-HPV antibodies was also shown in Table 6. Results of HPV DNA typing were also shown on the table for its corresponding case.

As shown in Table 7, nucleus staining is found in the dysplasia cells of all the CIN3 samples tested while only a certain proportion of cases found staining of cytoplasm by the anti-E7 antibody. The results indicate that there is more staining found in the cytoplasm than in the nucleus of dysplasia cells. As shown previously in invasive cancer tissues, HPV E7 protein in its adjacent normal epithelium cells was only found in the nucleus, but not found in the cytoplasm of the epithelial cells. The staining of cytoplasm appears most distinguishable in dysplasia cells compared to its corresponding normal adjacent cells. The localization of the E7 proteins expressed in the cytoplasm of dysplasia cells, but not in the normal epithelium or stroma cells appears HSIL specific. These data demonstrate expression of HPV E7 proteins can be detected in the cytoplasm and nucleus of dysplasia cells of CIN3 tissues. HPV E7 proteins present in the nucleus of normal adjacent epithelium and dysplasia cells detected by the anti-HPV E7 antibody indicate HPV infection with oncoproteins expression. For the cases with high level expression of HPV E7 proteins detected in the cytoplasm of dysplasia cells, it may suggest specific indication of dysplasia progression. A similar staining pattern was also found when other anti-HPV antibodies were used as shown in Table 7. Data indicate that the HPV IHC assay as described herein can detect HPV early genes such as E6, E7, and late genes such as L1 proteins present in the dysplasia cells of CIN3.

Comparing the results of HPV IHC to the HPV DNA typing, the anti-E7 antibody reacts positively with all the HPV types present in the samples tested. For example, the anti-E7 monoclonal antibody as described herein can detect a single HPV infection by at least HPV-16, HPV-18, HPV-31, HPV-33, HPV-39, HPV-58, etc, which are cancer-related HPV types (high risk HPV types). The single anti-E7 monoclonal antibody can also detect HPV infection by two or more HPV types, such as the combination of HPV-16, HPV-18, HPV-33, HPV-39, HPV-52, HPV-58, etc., which include most common high-risk HPV. These data indicate that the anti-E7 antibody described in this invention is non-type specific, and thus provides a powerful tool to detect HPV E7 proteins from most common high-risk HPV types in the CIN3 tissues.

TABLE 7

IHC staining results (stained % and score; 0-3) and HPV DNA typing of 30 CIN 3 samples (M: Membrane; C: Cytoplasmic; N: Nucleus; Dys: Dysplasia).

| ID # | HPV type | anti-E7 Dysplasia (% stained) | | | anti-E7 Normal epithelium (% stained) | | | Anti-E6 Dys. (%) Cyto | Another anti-E7 Dys. (%) Cyto | Anti-L1 Dys. (%) Cyto |
|---|---|---|---|---|---|---|---|---|---|---|
| | | M | C | N | M | C | N | | | |
| 31 | 33 | 0 | 80 | 80 | 0 | 0 | 50 | 70 | 40 | 80 |
| 32 | 16 | 0 | 80 | 80 | | | 60 | 0 | 0 | 5 |
| 33 | 16, 58 | | | | 0 | 0 | 60 | | | |
| 34 | 31 | 0 | 50 | 70 | 0 | 0 | 50 | 0 | 0 | 10 |
| 35 | 16, 39 | 0 | 70 | 90 | 0 | 0 | 40 | 0 | 10 | 30 |
| 36 | 31 | 0 | 70 | 60 | 0 | 0 | 50 | 0 | 20 | 20 |
| 37 | 39 | 0 | 0 | 40 | 0 | 0 | 0 | 0 | 0 | 0 |
| 38 | 16 | | | | 0 | 0 | 40 | | | |
| 39 | 16 | 0 | 60 | 70 | 0 | 0 | 40 | 0 | | 0 |
| 40 | 58 | 0 | 90 | 90 | 0 | 0 | 50 | 50 | 0 | 30 |
| 41 | 16 | 0 | 0 | 50 | 0 | 0 | 50 | 0 | 20 | 20 |
| 42 | 16 | 0 | 70 | 70 | 0 | 0 | 30 | 0 | 0 | |
| 43 | 33 | 0 | 0 | 90 | 0 | 0 | 50 | 0 | 0 | 5 |
| 44 | 52 | 0 | 70 | 80 | 0 | 0 | 50 | 70 | 10 | 50 |
| 45 | 51, 52 | 0 | 90 | 90 | 0 | 0 | 30 | 80 | 50 | 10 |
| 46 | 16 | 0 | 0 | 80 | 0 | 0 | 50 | 0 | 0 | 5 |
| 47 | 16 | 0 | 60 | 80 | 0 | 0 | 50 | 30 | 10 | 20 |
| 48 | 16, 58 | 0 | 0 | 80 | 0 | 0 | 50 | 0 | 0 | 10 |
| 49 | 31 | 0 | 80 | 60 | | | 50 | 70 | 40 | 40 |
| 50 | 16 | 0 | 0 | 60 | 0 | 0 | 30 | 0 | 20 | 20 |
| 51 | 6 | | | | 0 | 0 | 20 | | 0 | |
| 52 | 16, 18, 33, 39 | 0 | 0 | 20 | 0 | 0 | 30 | 0 | 0 | 0 |
| 53 | 51, 52, 58 | 0 | 70 | 60 | 0 | 0 | | 60 | 60 | 40 |
| 54 | 16, 45 | 0 | 0 | 70 | 0 | 0 | 50 | 0 | 20 | 20 |
| 55 | 16 | 0 | 0 | 75 | 0 | 0 | 50 | 0 | 0 | 0 |
| 56 | 33, 52 | 0 | 0 | 80 | 0 | 0 | 50 | 0 | 0 | 10 |
| 57 | 16 | 0 | 0 | 50 | 0 | 0 | 40 | 0 | 0 | 0 |
| 58 | 33 | 0 | 0 | 80 | 0 | 0 | | 0 | 20 | 10 |
| 59 | 16 | 0 | 0 | 60 | 0 | 0 | 20 | 0 | 10 | 5 |
| 60 | 16, 52, 58 | 0 | 70 | 80 | 0 | 0 | 50 | 70 | 0 | 20 |

An object of the invention is to develop immune-responsive or antibody-reactive recombinant proteins derived from early genes and/or late genes of various HPV types and strains. It is a further object to provide these recombinant proteins in a chemically pure form. It is a still further object to provide simple, rapid, less expensive and more sensitive assays/tests for diagnosing not only HPV infection, but also most, if not all, HPV-associated neoplasm.

Cloning and production of recombinant proteins encoded by HPV genes: Recombinant proteins encoded by early HPV genes and late HPV genes are obtained. Recombinant proteins can be obtained by itself or as hybrid proteins fused transcriptionally or translational to a portion of a full length DNA fragment for a HPV gene of interest. The DNA sequence of the HPV gene of interest may be derived from high risk HPV types, low risk HPV types, oncogenic HPV strains within a HPV type, etc. An oncogenic HPV strain is an HPV strain that is known to cause cervical cancer as determined by the National Cancer Institute (NCI, 2001). Oncogenic HPV proteins are early viral proteins encoded by an oncogenic HPV type or strain. The sequences of various HPV viral genes and proteins are also found as database entries at NCBI's Gene Bank database, as follows: HPV16-E6: GI:9627100; HPV18-E6: GI:9626069; HPV31-E6: GI:9627109; HPV35-E6: GI:9627127; HPV30-E6: GI:9627320; HPV39-E6: GI:9627165; HPV45-E6: GI:9627356; HPV51-E6: GI:9627155; HPV52-E6:

GI:9627370; HPV56-E6: GI:9627383; HPV59-E6: GI:9627962; HPV58-E6: GI:9626489; HPV33-E6: GI:9627118; HPV66-E6: GI:9628582; HPV68b-E6: GI:184383; HPV69-E6: GI:9634605; HPV26-E6: GI:396956; HPV53-E6: GI:9627377; HPV73: GI:1491692; HPV82: GI:9634614, HPV34 GI:396989; HPV67 GI:3228267; and HPV70 GI:1173493.

Cloning and production of various recombinant proteins encoded by HPV-16, early E6 gene: Cloning of an exemplary oncogenic E6 early gene from an exemplary HPV type, HPV-16, is described herein. A 474 base pair (b.p.) DNA fragment (SEQ ID NO. 1) containing the 157 amino acid coding region (SEQ ID NO. 2) of the HPV-16 E6 gene was obtained by polymerase chain reaction (PCR) amplification. Primers were used for cloning, for example, a pair of forward and reverse primers, 5' cgcGGATCCcaccaaaagagaactgcaatgtttc 3' (SEQ ID NO. 3) and 5' cccAAGCTTttacagctgggtttctctacgtg 3' (SEQ ID NO. 4), respectively. The DNA sequence of the isolated DNA fragment was confirmed by comparing with the sequence from Gene Bank database. All cloning procedures are carried out according to the protocols described in "Molecular Cloning", A Laboratory Manual, eds. Sambrook, Fritsch and Maniatis, Cold Spring Harbor Laboratory Press, 1989. In addition, E6 DNA fragments from different strains of HPV-16 can also be cloned from different clinical samples or sources.

The obtained 474 base pair (b.p.) DNA fragment was sub-cloned into a histidine tag expression vector, pQE30, in order to express a his-tagged recombinant HPV-16 E6 protein. The resulting plasmid DNA is designated, pQE30/HPV16-E6 for the expression of His-tagged-HPV16-E6 recombinant protein. The DNA sequence and the amino acid sequences of the resulting his-tagged recombinant HPV-16 E6 protein are shown as SEQ ID NO. 5 (a 510 base pair (b.p.) DNA fragment) and SEQ ID NO. 6 (a 169 amino acid fusion protein), respectively.

Cloning and production of recombinant proteins encoded by HPV-16 early E7 gene: Cloning of an exemplary oncogenic E7 early gene from an exemplary HPV type, HPV-16, is described herein. A 294 base pair (b.p.) DNA fragment (SEQ ID NO. 7) containing the 99 amino acid coding region (SEQ ID NO. 8) of the HPV-16 E7 gene was obtained by polymerase chain reaction (PCR) amplification. Primers were used for cloning, for example, a pair of forward and reverse primers, 5' cgcGGATCCcatggagatacacctacattgc 3' (SEQ ID NO. 9) and 5' ccgGAATTCttatggtttctgagaacagatgg 3' (SEQ ID NO. 10), respectively. The DNA sequence of the isolated DNA fragment was confirmed by comparing with the sequence from Gene Bank database. In addition, E7 DNA fragments from different strains of HPV-16 can also be cloned from different clinical samples or sources.

The obtained 294 base pair (b.p.) DNA fragment was sub-cloned into a GST expression vector in order to express a recombinant HPV-16 E7 GST fusion protein. The DNA sequence and the amino acid sequences of the resulting recombinant HPV-16 E7 GST protein are shown as SEQ ID NO. 11 (a 972 base pair (b.p.) DNA fragment) and SEQ ID NO. 6 (a 323 amino acid fusion protein), respectively. The molecular weight of the resulting recombinant HPV-16 E7 GST protein is about 37.2 KD. The recombinant HPV-16 E7 GST proteins were obtained and purified to a final concentration of about 1 mg/L. Other expression systems can also be used to express E7 recombinant proteins from various HPV types and strains. Recombinant E7 fusion proteins or recombinant E7 baculovirus proteins were used to detect the presence of E7 antibody on clinical samples and were also be used as immunogens for production of polyclonal antiserum and monoclonal antibodies.

Methods of producing the monoclonal antibody are provided herein to obtain monoclonal antibodies recognizing one or more common epitopes of HPV proteins among various HPV proteins or HPV types. In addition, some of the monoclonal antibodies obtained herein are HPV type-specific, while some of the monoclonal antibodies obtained herein are non-HPV type-specific. The non-HPV type-specific antibodies recognize most of the prevalent HPV types present in clinical samples. As a result, these monoclonal antibodies are suitable to be used in an assay to detect HPV infection in one or more clinical samples.

To analyze the HPV IHC results from each subject of CIN2, Table 8 shows data from 30 cases of CIN 2 samples with IHC scores for staining of cell membrane (M), cytoplasm (C), and nucleus (N) using M, C, or N followed by the % of staining with the anti-E7 antibody. Additional anti-HPV antibodies including Anti-HPV E6 antibody like MAb1 and MAb 7 and anti-HPV L1 antibody were also tested on the same tissue microarray. To demonstrate the IHC staining by various anti-HPV antibodies, IHC score from cytoplasm staining of dysplasia cells using other anti-HPV antibodies is also shown in Table 8. Results of HPV DNA typing are also shown in the table for its corresponding case.

TABLE 8

IHC staining results (stained % and score; 0-3) and HPV DNA typing for 30 biopsy samples (CIN2). (M: membrane; C: cytoplasmic; N: nucleus; Dys: dysplasia)

| | | Anti-E7 | | | | | | Anti-E6 Dys. (%) | another anti-E7 Dys. (%) | Anti-L1 Dys. (%) |
|---|---|---|---|---|---|---|---|---|---|---|
| | | Dysplasia (% stained) | | | Normal epithelium (% stained) | | | | | |
| ID # | HPV type | M | C | N | M | C | N | Cyto | Cyto | Cyto |
| 1 | 6 | 0 | 80 | 80 | 0 | 0 | 30 | 70 | 40 | 80 |
| 2 | 31 | 0 | 0 | 90 | | | | 0 | 40 | 0 |
| 3 | 52 | 0 | 25 | 50 | 0 | 0 | 70 | 0 | 20 | 20 |
| 4 | 16 | 0 | 0 | 40 | 0 | 0 | 30 | 0 | 5 | 0 |
| 5 | 58 | 0 | 0 | 50 | 0 | 0 | 10 | 0 | 0 | 0 |
| 6 | 52 | 0 | 80 | 70 | 0 | 0 | 50 | 0 | 5 | 0 |
| 7 | 53 | 0 | 0 | 80 | 0 | 0 | 30 | 0 | 10 | 10 |
| 8 | 52 | 0 | 50 | 90 | 0 | 0 | 20 | 60 | 10 | 20 |
| 9 | 31 | 0 | 80 | 80 | 0 | 0 | 50 | 70 | 20 | 40 |
| 10 | 16 | 0 | 50 | 80 | 0 | 0 | 50 | 60 | 20 | 10 |
| 11 | no DNA | 0 | 0 | 50 | 0 | 0 | 70 | 0 | 0 | 10 |
| 12 | 33 | 0 | 60 | 60 | 0 | 0 | 50 | 0 | 10 | 30 |
| 13 | no DNA | 0 | 70 | 80 | 0 | 0 | 70 | 0 | 20 | 10 |
| 14 | 52 | 0 | 0 | 70 | 0 | 0 | 70 | 0 | 30 | 20 |
| 15 | no DNA | 0 | 0 | 70 | 0 | 0 | 50 | 0 | 20 | 5 |
| 16 | 52 | 0 | 0 | 10 | 0 | 0 | 30 | 0 | 0 | 5 |
| 17 | 52 | 0 | 0 | 60 | 0 | 0 | 80 | 0 | 0 | 5 |
| 18 | 16 | 0 | 50 | 60 | 0 | 0 | 30 | 50 | 10 | 20 |
| 19 | 16 | 0 | 50 | 70 | | | | 0 | 10 | 20 |
| 20 | 52, 44 | 0 | 50 | 80 | 0 | 0 | 40 | 0 | 30 | 30 |
| 21 | 16 | 0 | 0 | 50 | 0 | 0 | 50 | 0 | 20 | 20 |
| 22 | 16, 18, 6 | 0 | 0 | 40 | 0 | 0 | 0 | 0 | 10 | 0 |
| 23 | 16, 31 | 0 | 0 | 30 | 0 | 0 | 60 | 0 | 0 | |
| 24 | 6 | 0 | 0 | 80 | 0 | 0 | 50 | 0 | 10 | 5 |
| 25 | 16 | 0 | 0 | 10 | 0 | 0 | 60 | 0 | 0 | 0 |
| 26 | 58 | 0 | 0 | 40 | 0 | 0 | 40 | 0 | 10 | 5 |
| 27 | 16, 39, 52 | | | | 0 | 0 | 70 | | 0 | |
| 28 | 6 | 0 | 0 | 50 | 0 | 0 | 70 | 0 | 10 | 5 |
| 29 | 16 | 0 | 0 | 70 | 0 | 0 | 5 | 0 | 10 | 20 |
| 30 | 66, 68, | 0 | 0 | 30 | 0 | 0 | 60 | 0 | 10 | 0 |

As shown in Table 8, nucleus staining is found in the dysplasia cells of all the CIN2 samples tested while only a certain proportion of cases found staining of cytoplasm by the anti-E6 or anti-E7 antibody. The results indicate there is more staining of nucleus than cytoplasm of dysplasia cells found in CIN2 samples. As shown previously in SCC, ADC, and CIN3, HPV E7 protein in its adjacent normal epithelium cells was only found in the nucleus, but not found in the cytoplasm of the epithelial cells. The staining of cytoplasm in CIN2 using anti-E6 antibody appears most distinguishable in dysplasia cells compared to its corresponding normal adjacent cells. The localization of the E6 proteins expressed in the cytoplasm of dysplasia cells, but not in the normal epithelium or stroma cells appears HSIL specific. These data demonstrate expression of HPV E6 proteins can be detected in the cytoplasm and nucleus of dysplasia cells of CIN2 tissues. For the cases with high level expression of HPV E6 proteins detected in the cytoplasm of dysplasia cells, it may suggest dysplasia progression. A similar staining pattern was also found when other anti-HPV antibodies were used as shown in Table 8. The HPV IHC assay as described herein can be used to detect HPV early genes such as E6, E7, and late genes such as L1 proteins present in the dysplasia cells of CIN2.

Comparing the results of HPV IHC to the HPV DNA typing, the anti-E7 antibody reacts positively with all the HPV types present in the samples tested. For example, the anti-E7 monoclonal antibody as described herein can detect a single HPV infection by at least, HPV-16, HPV-18, HPV-31, HPV-52, HPV-58, etc, which are cancer-related HPV types (high risk HPV types) and HPV6, HPV 53 which are not high-risk HPV types. The single anti-E7 monoclonal antibody can also detect HPV infection by two or more HPV types, such as the combination of HPV6, HPV-16, HPV-18, HPV-31, HPV-39, HPV-44, HPV-52, HPV-58, HPV-66, HPV-68, etc., which include most common high-risk HPV as well as low risk HPV types. These data indicate that the anti-E7 antibody described in this invention is non-type specific, able to detect HPV E7 proteins from common high-risk HPV types as well as low risk types in the CIN2 tissues. It is possible that formation of dysplasia cells is resulted from expression of oncoproteins, rather than genotyping of HPV types. It shows regression may occur for those infections by high-risk types with no detection of oncoproteins in cytoplasm. Thus, the HPV IHC assay described herein provides additional clinical information, not only for detection of HPV infection, but also for indication of dysplasia progression.

The invention claimed is:

1. A method of detecting papillomavirus infection in a human subject and determining a risk of the human subject developing a cancerous lesion, comprising:
receiving a sample obtained from the human subject, the sample comprising a mixed population of normal cells and cells susceptible to infection by a papillomavirus,
contacting in solution the sample with a staining reagent comprising an anti-HPV monoclonal antibody generated against a purified recombinant papillomavirus protein, wherein
the monoclonal antibody specifically binds to two or more native HPV proteins from different HPV types, wherein
the two or more native HPV proteins are native E7 proteins from different HPV types or native E6 proteins from different HPV types, and
the monoclonal antibody is capable of binding in situ to the native HPV proteins in a clinical sample; and
the contact in solution between the sample and the staining reagent results in a staining on the cells susceptible to infection by a papillomavirus, wherein the staining is caused by a binding between the anti-HPV monoclonal antibody in the staining reagent and the native HPV proteins in the sample, and
the staining is indicative of the presence of a papillomavirus protein in the sample thereby indicating papillomavirus infection in the human subject; and
detecting and quantifying the staining in each individual cell in the sample; and
determining a score for the sample based on the quantification of the staining wherein the score indicates a risk of the human subject developing a cancerous lesion.

2. The method of claim 1, wherein the one or more purified recombinant papillomavirus protein is selected from the group consisting of recombinant E6 protein from HPV-16, recombinant E7 protein from HPV-16, recombinant E6 protein from HPV-18, and recombinant E7 protein from HPV-18.

3. The method of claim 1, wherein the native HPV proteins are native E6 protein from HPV 16 and native E6 protein from HPV 18.

4. The method of claim 1, wherein the papillomavirus protein is selected from the group consisting of papillomavirus E6 protein and papillomavirus E7 protein.

5. The method of claim 1, wherein the papillomavirus protein has a papillomavirus type selected from the group consisting of high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56.

6. The method of claim 1, further comprising determining an intensity of staining and determining a disease stage wherein the disease stage is based on the staining pattern or the intensity of staining and wherein the disease stage is selected from the group consisting of early stage HPV infection, late stage HPV infection, early stage cervical lesion, late stage cervical lesion, low grade of squamous intraepithelial lesion (LSIL), high grade of squamous intraepithelial lesion (HSIL), atypical squamous cells of undetermined significance (ASCUS), cervical intraneoplasm stage 1, 2, 3 (CIN1, CIN2, CIN3, respectively), invasive cervical cancer, adenocarcinoma (ADC), and squamous cell carcinoma (SCC).

7. The method of claim 1, further comprising
performing a cytological Papanicolaou smear assay on the sample and
comparing results of the cytological Papanicolaou smear assay with the staining by the staining reagent.

8. The method of claim 1, wherein the staining reagent further comprises a fluorescent agent or a colorimetric agent.

9. The method of claim 1, wherein the sample comprises a component selected from the group consisting of cervical cells, cervical tissues, cervical swabs, body fluids, serum, blood, tumors, cell cultures, and biopsies.

10. The method of claim 1, further comprising determining the presence of cervical cancer in the human subject based on the determined score.

11. The method of claim 1, wherein the cells are dispersed in a collection liquid.

12. The method of claim 1, wherein the purified recombinant papillomavirus protein has native or near-native conformation.

13. The method of claim 1, wherein the antibody is capable of specifically binding to a papillomavirus protein epitope present in a population of morphologically identifiable cells.

14. The method of claim 1, wherein the risk is assessed to be high if there is positive staining that exceeds a predetermined threshold.

15. The method of claim 1, wherein the native HPV E7 proteins are native E7 protein from HPV 16 and native E7 protein from HPV 18.

* * * * *